US011053303B2

(12) United States Patent
Lebert et al.

(10) Patent No.: US 11,053,303 B2
(45) Date of Patent: Jul. 6, 2021

(54) ANTIBODY-LIKE PEPTIDES FOR QUANTIFYING THERAPEUTIC ANTIBODIES

(71) Applicant: Promise Advanced Proteomics, Grenoble (FR)

(72) Inventors: Dorothée Lebert, Le Gua (FR); Guillaume Picard, Mont-Saxonnex (FR)

(73) Assignee: PROMISE PROTEOMICS, Grenoble (FR)

( * ) Notice: Subject to any disclaimer, the term of this patent is extended or adjusted under 35 U.S.C. 154(b) by 137 days.

(21) Appl. No.: 16/132,819

(22) Filed: Sep. 17, 2018

(65) Prior Publication Data
US 2019/0085056 A1 Mar. 21, 2019

(30) Foreign Application Priority Data
Sep. 19, 2017 (EP) .................................... 17306215

(51) Int. Cl.
| | | |
|---|---|---|
| *C07K 16/00* | (2006.01) | |
| *C07K 16/18* | (2006.01) | |
| *C07K 16/06* | (2006.01) | |
| *G01N 33/68* | (2006.01) | |

(52) U.S. Cl.
CPC .......... *C07K 16/065* (2013.01); *C07K 16/00* (2013.01); *C07K 16/18* (2013.01); *G01N 33/683* (2013.01); *G01N 33/6848* (2013.01); *G01N 33/6857* (2013.01); *G01N 2560/00* (2013.01)

(58) Field of Classification Search
CPC ...... C07K 16/065; C07K 16/00; C07K 16/18; G01N 33/683; G01N 33/6848; G01N 33/6857
USPC ....................................................... 530/387.3
See application file for complete search history.

(56) References Cited

U.S. PATENT DOCUMENTS

2017/0174774 A1* 6/2017 Coric ................. C07K 16/3053

FOREIGN PATENT DOCUMENTS

| WO | WO 2015/049763 | 4/2015 |
| WO | WO 2017/011342 | 1/2017 |
| WO | WO 2017/050825 | 3/2017 |
| WO | WO 2017/077081 | 5/2017 |

OTHER PUBLICATIONS

Peng et al. (Chromatographia, Vieweg Uno Teubner Verlag, DE, vol. 78, No. 7, Feb. 28, 2015, pp. 521-531).*
Lebert et al. (Bioanalysis, Future Science, 2015, 7(10): 1237-1251).*
Ewles et al., *LC-MS/MS Strategies for Quantification of Therapeutic Antibodies to Support Clinical and Preclinical Studies and Preclinical Studies*, 8(24) Bioanalysis (Nov. 16, 2015).

* cited by examiner

*Primary Examiner* — Yan Xiao
(74) *Attorney, Agent, or Firm* — Buchanan Ingersoll & Rooney PC

(57) ABSTRACT

The present invention relates to a labeled chimeric non-therapeutic antibodylike protein comprising, in a hypervariable region thereof, an enzyme cleavable peptide sequence derived from a hypervariable region of a reference therapeutic antibody.

15 Claims, 9 Drawing Sheets

Specification includes a Sequence Listing.

ANTIBODY-LIKE PEPTIDES FOR QUANTIFYING THERAPEUTIC ANTIBODIES

CROSS-REFERENCE TO RELATED APPLICATIONS

This application claims priority to European Patent Application 17306215.9, filed on Sep. 19, 2017, which is incorporated herein by reference in its entirety for all purposes.

FIELD OF THE INVENTION

The invention relates to the field of antibody quantification. In particular, it relates to methods for the quantification of therapeutic antibodies.

BACKGROUND OF THE INVENTION

The analysis of biological samples, generated from in vivo studies of therapeutic antibodies, is of interest in the biopharmaceutical industry.

Monoclonal antibodies (mAbs) are an upcoming group of therapeutic compounds used to treat various types of diseases. Monoclonal antibodies (mAbs) constitute a therapeutic class which knows the strongest current rate of development in the field of pharmaceutical biotechnology. There are to date more than 50 mAbs marketed in various fields such as oncology, immunology, ophthalmology and cardiology. Monoclonal antibodies have provided important medical results in the treatment of several major diseases including autoimmune, cardiovascular and infectious diseases, cancer and inflammation, clinical trials.

Antibody-based therapy, in particular for cancer, has become established over the past 15 years and is now one of the most successful and important strategies for treating patients with hematological malignancies and solid tumors. The use of monoclonal antibodies for cancer therapy has achieved considerable success in recent years. Notably, antibody-drug conjugates are powerful new treatment options for lymphomas and solid tumours, and immunomodulatory antibodies have also recently achieved remarkable clinical success. The development of therapeutic antibodies requires a deep understanding of cancer serology, protein-engineering techniques, mechanisms of action and resistance, and the interplay between the immune system and cancer cells.

Given the polypeptide nature of therapeutic mAbs, their high degree of homology with the endogenous human IgGs and the low concentrations at which they are expected in the plasma environment, the determination of concentrations of therapeutic monoclonal antibodies in biological samples such as human plasma and human serum-derived samples is difficult. To establish the pharmacokinetic (PK) properties of mAbs in human samples, many clinical studies are required. Samples of these studies are most often analyzed using immunoassays. Although immunoassays are very fast and sensitive, there are also some limitations.

The conventional ELISA approach has been used for over 25 years and has several limitations. The ELISA methods require high quality custom reagents that can take several months to generate and the assay optimization can take an additional number of months. Thus, ELISA has a long assay development time which is a limitation in both the early discovery stage and the development stage of protein-based drugs. Suitable ELISA reagents and assay conditions may not be possible in some cases due to the highly custom binding requirements for each protein therapeutic. Another limitation of ELISA is that reagents may bind non-specifically to plasma/serum proteins and matrix interference is a common phenomenon.

Protein quantification by mass spectrometry on the other hand is highly specific and therefore matrix interference is rare compared to ELISA. Mass spectrometry methods of protein quantification, LC-MS/MS in particular, do not require custom reagents and generally yields faster assay development. In addition, mass spectrometry is less subject to matrix interferences and provides generic assay conditions which are highly specific and can be multiplexed and automated. The high specificity of mass spectrometry measures analyte concentration using intrinsic physical chemical properties of the analyte, i.e. mass and fragmentation pattern. The robust format allows ready lab-to-lab transfer, a significant advantage for approved antibody therapies. A general methodology for quantifying proteins by mass spectrometry is trypsin digestion of the intact protein. The resulting peptides are analyzed by mass spectrometry by introducing corresponding stable isotope labeled internal standards at a fixed concentration.

Liquid chromatography-tandem mass spectrometry is a powerful tool for protein analysis and quantitation in very complex matrices like plasma/serum samples. Since peptides resulting from the digestion of the protein of interest and other plasma/serum proteins may have the same or similar nominal mass, the second dimension of MS fragmentation often provides a unique fragment of a peptide of interest.

As it can be readily understood, methods for monitoring concentrations of one or more therapeutic antibodies in a biological sample shall be highly specific, sensitive, accurate and reproducible, so as to define the appropriate dosing adjustments that should be beneficial to a patient.

Methods for the quantification of proteins by mass spectrometry have been reported in the Art. In a non-limitative manner, those methods may differ by:
   (i) the preparation method of the sample to be analyzed;
   (ii) the type of mass spectrometry;
   (iii) the type of standards; and/or
   (iv) the type of protein(s) that must be quantified.

WO 2008/145763 teaches methods for absolute quantification of polypeptide by mass spectrometry using PSAQ™ standards. PSAQ™ standards are full-length stable isotope labeled protein standards similar to the protein analyte, produced using cell-free expression systems.

Lebert et al. ("*Absolute and multiplex quantification of antibodies in serum using PSAQ™ standards and LC-MS/MS*"; Bioanalysis; 2015) teaches multiplex assays for the quantification of antibodies by mass spectrometry, using a Protein Standard Absolute Quantification (PSAQ™) standard, in rodent serum samples.

WO 2006/128492 A1 and Beynon et al. («Multiplexed absolute quantification in proteomics using artificial QCAT proteins of concatenated signature peptides»; Nature Methods; 2005) teach the use, as an internal standard, of an artificial protein consisting of a concatemer of Q peptides (QCAT protein), for absolute quantification of the proteome by mass spectrometry. Q peptides are characterized as naturally occurring tryptic peptides in the parent protein, in a strict 1:1 stochiometry.

Stable-Isotope Labeled Universal Monoclonal Antibody (SILU™Mab) standards, commercialized by SIGMA-ALDRICH, are used in methods for the quantification of antibodies by mass spectrometry. SILUMabs are purified stable isotope-labeled IgG monoclonal antibodies, having a Fc region containing peptides sequences from human IgG constant regions. After trypsin-digestion, the SILU™Mab standards are reported to generate tryptic peptide sequences having sequence homology with sequences of human IgG antibodies and thus are suited for quantification of humanized antibodies in animal serum samples.

Yet, there is still a need for improved and/or alternative tools & methods for the quantification of therapeutic antibodies, that would allow an accurate quantification of these antibodies in samples collected from patients subjected to antibody treatments, which quantification methods shall be useful irrespective of the kind of therapeutic antibodies that has been administered to those patients and moreover, non-sensitive to the potential presence of other therapeutic antibodies previously administered.

Thus there is a need for improved and/or alternative methods for the quantification of therapeutic antibodies, which are both suitable for multiplex quantification, and applicable to human samples in an accurate, sensitive and reproducible manner.

In particular, there is a need for methods for quantification of polypeptides which are compatible with sample prefractionation steps and/or the proteolysis step that is generally required before MS analysis.

Also, there is a need for all-in-one simple methods allowing to quantify therapeutic antibodies in samples of treated patients, which methods would not require that the medical practitioners select a specific kit or method according to the specific therapeutic antibody that is expected to be contained in the patient samples.

The invention has for purpose to meet those needs.

SUMMARY OF THE INVENTION

This invention relates to a non-therapeutic antibody-like protein comprising, in a hypervariable region thereof, an enzyme-cleavable peptide sequence derived from a hypervariable region of a reference therapeutic antibody.

In most preferred embodiments, the said non-therapeutic antibody-like protein that is described throughout the present specification consists of a labeled non-therapeutic antibody-like protein.

The said non-therapeutic antibody, because it comprises, in a hypervariable region thereof, a polypeptide originating from a hypervariable region of a reference therapeutic antibody, may also be termed a "chimeric" antibody herein.

Then, this invention relates to a chimeric non-therapeutic antibody comprising, in a hypervariable region thereof, an enzyme-cleavable peptide sequence derived from a hypervariable region of a reference therapeutic antibody.

As it will be described throughout the present specification, the said chimeric non-therapeutic antibody has been conceived to be employed as an internal standard molecule for its use in a method of quantifying therapeutic antibodies, and more particularly for its use in a method for quantifying therapeutic antibodies by mass spectrometry. This chimeric non-therapeutic antibody may also be termed a chimeric non-therapeutic quantitation antibody herein.

Further, as it is above-described, a chimeric non-therapeutic antibody according to the invention, because it comprises, in a hypervariable region thereof, at least an exogenous sequence originating from a hypervariable region of a reference therapeutic antibody to be quantified, the said chimeric non-therapeutic antibody does not consist of a conventional antibody comprising all the hypervariable regions of an antibody directed to a specific antigen. This is why a chimeric non-therapeutic quantitation antibody as described herein may also be termed "chimeric antibody-like protein" herein, the said chimeric antibody-like protein being structurally similar to a reference therapeutic antibody to be quantified.

This invention concerns a chimeric antibody-like protein structurally similar to a reference therapeutic antibody, comprising in a hypervariable region of the said chimeric non-therapeutic antibody-like protein, an enzyme-cleavable peptide sequence derived from a hypervariable region of the said reference therapeutic antibody.

This invention relates to a chimeric non-therapeutic antibody-like protein structurally similar to a reference therapeutic antibody, comprising in a hypervariable region of the said chimeric non-therapeutic antibody-like protein, an enzyme-cleavable peptide sequence derived from a hypervariable region of the said reference therapeutic antibody.

In most preferred embodiments, the chimeric non-therapeutic antibody-like protein described herein is labeled, so as to allow mass discrimination between (i) an enzyme-cleaved labeled peptide derived from a hypervariable region of a therapeutic antibody comprised therein and (ii) the same enzyme-cleaved peptide originating from the said therapeutic antibody to be quantified, when performing a therapeutic antibody quantitation method using mass spectrometry.

This invention also relates to a composition comprising a chimeric non-therapeutic antibody-like protein as defined above.

This invention further concerns a method for quantifying one or more therapeutic antibodies in a sample of an individual comprising the steps of:

a) adding, to a test sample which contains at least one therapeutic antibody, a known amount of a labeled form of a chimeric non-therapeutic antibody-like protein as defined above, whereby a pre-proteolysis sample is provided, b) subjecting the pre-proteolysis sample to an enzyme proteolysis, so as to provide a proteolysis sample comprising (i) proteolysis labeled peptide(s) derived from the labeled chimeric non-therapeutic antibody-like protein and (ii) proteolysis peptide(s) derived from the therapeutic antibody contained in the test sample, c) determining, by mass spectrometric analysis, the ratio between (i) one or more selected proteolysis labeled peptides derived from the labeled chimeric non-therapeutic antibody-like protein and (ii) one or more corresponding proteolysis peptides derived from the said therapeutic antibody, d) calculating from the ratio determined at step c) the amount of the said therapeutic antibody in the test sample.

This invention further relates to a kit for quantifying therapeutic antibodies comprising at least:

a therapeutic antibody, either in a purified form or in a diluted form in a protein-containing solution, a labeled form of a chimeric non-therapeutic antibody as defined above, either in a purified form or in a diluted form in a protein-containing solution.

This invention further relates to a kit for quantifying therapeutic antibodies comprising:

a labeled form of a chimeric non-therapeutic antibody as defined above; and calibration samples suited for performing a calibration curve.

The present invention also concerns the use of at least one polypeptide derived from a hypervariable region of a therapeutic antibody, or of a nucleic acid coding for the said polypeptide, for the preparation of a chimeric non-therapeutic antibody-like protein as defined above.

According to some embodiments, the invention relates to an isolated nucleic acid coding for a polypeptide comprising a sequence selected from the group consisting of: SEQ ID No1 to 12 and SEQ ID No113 to 119.

DETAILED DESCRIPTION OF THE INVENTION

Figure 1:
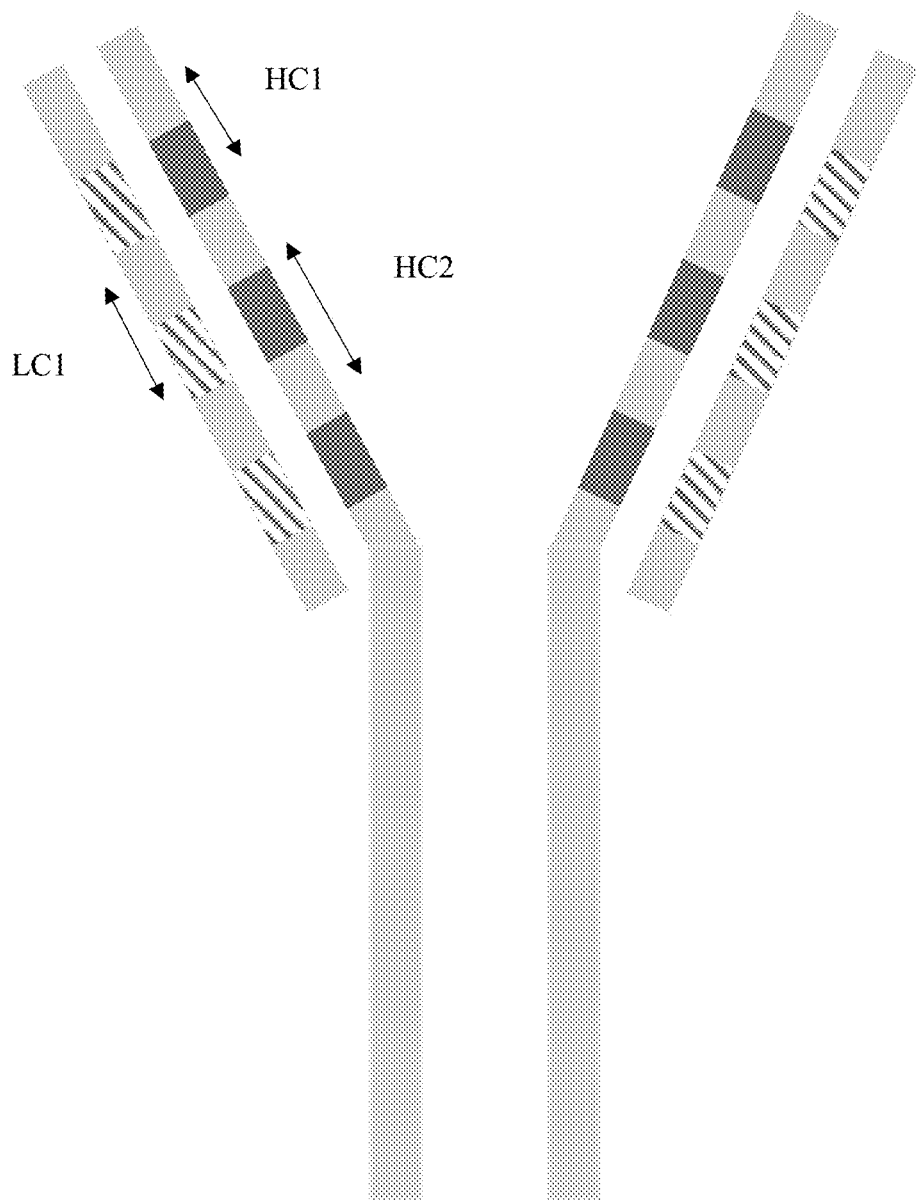
FIG. 1: schematical representation of an antibody-like protein. In this example, the antibody-like protein comprises a variable region which, upon proteolysis treatment with trypsin, generates a light chain proteotypic tryptic peptide (LC1), a first heavy chain proteotypic peptide (HC1) and a second heavy chain proteotypic peptide (HC2). Each therapeutic antibody contains several proteotypic peptides. A proteotypic peptide is the unique and minimal sequence needed to identify the therapeutic antibody from a LC-MS/MS analysis, in a mixture containing other human IgG. Thus, it is admitted that a proteotypic peptide contains at least one amino acid from a CDR of a given set of therapeutic antibodies.

Methods for quantifying therapeutic antibodies by mass spectrometry (MS) generally require submitting the test sample to a proteolysis step before MS analysis.

The intensity of the peaks obtained from the proteolysis peptide fragments may then be compared to standard (generally isotope-labeled) peptide fragments in order to obtain an absolute quantification within the test sample The inventors are of the opinion that said proteolysis step may lead to severe biases, due in part to the poor accessibility to proteases of such therapeutic antibodies.

The inventors have now found that those specific methods of quantification could be improved by adding to said test sample, and before the proteolysis step, a novel type of internal standard that is versatile and that allows an accurate quantification of a therapeutic antibody of interest, without requiring the use of the therapeutic antibody itself, and especially without requiring the use of a labeled form of the said therapeutic antibody.

The inventors have conceived a novel type of an internal standard to be used in methods for quantifying therapeutic antibodies, the said internal standard consisting of a chimeric non-therapeutic antibody-like protein comprising, in a hypervariable region thereof, an enzyme-cleavable peptide sequence derived from a hypervariable region of a therapeutic antibody to be quantified, which therapeutic antibody may also be termed a "reference" therapeutic antibody in the present specification.

Thus, the present invention relates to a chimeric non-therapeutic antibody-like protein comprising, in a hypervariable region thereof, an enzyme cleavable peptide sequence derived from a hypervariable region of a reference therapeutic antibody.

Most preferred embodiments of a chimeric non-therapeutic antibody-like protein described throughout the present specification consist of a labeled chimeric non-therapeutic antibody-like protein.

The said chimeric non-therapeutic antibody-like protein is structurally similar to a reference therapeutic antibody to be quantified and comprises, in a hypervariable region thereof, an enzyme-cleavable peptide sequence derived from a hypervariable region of the said reference therapeutic antibody.

Most preferred embodiments encompass a labeled form of the chimeric non-therapeutic antibody-like protein described throughout the present specification.

The inventors have thus conceived an antibody-like protein having the general structural features of an antibody, and especially having the general structural features of a reference therapeutic antibody to be quantified, the said antibody-like protein comprising, in a hypervariable region thereof, an enzyme-cleavable peptide derived from a hypervariable region of the said reference therapeutic antibody. The said antibody-like proteins are also termed "chimeric non-therapeutic antibody" herein.

The said chimeric antibody-like protein comprises, in a hypervariable region thereof, all or part of a hypervariable region of a reference therapeutic antibody to be quantified and the said exogenous hypervariable region or part of hypervariable region comprises an enzyme-cleavable peptide sequence, i.e. at least one enzyme-cleavable peptide sequence.

The polypeptide derived from the said reference therapeutic antibody (polypeptide also termed "TADP" for "Therapeutic Antibody Derived Polypeptide" throughout the present specification) which is contained in a hypervariable region of a chimeric antibody-like protein, comprises an enzyme-cleavable peptide that may be quantified subsequently to a step of proteolysis, when performing a therapeutic antibody quantitation method.

Surprisingly, the accuracy of the quantification of a reference therapeutic antibody with such a chimeric antibody-like protein is at least comparable to the quantification with labelled therapeutic antibodies. Indeed, the accessibility of such enzyme-cleavable peptide-containing exogenous hypervariable(s) regions to proteases was prima facie expected to vary in such chimeric antibody-like proteins. Yet, FIGS. 3 and 4 provide evidence that the use of chimeric antibody-like proteins as internal standards for the quantification of Cetuximab and Bevacizumab, in human serum, led to differences of less than 5% in terms of accuracy, when compared to the use of labelled forms of therapeutic Cetuximab and Bevacizumab.

As used herein, a "therapeutic antibody" refers to an antibody that is approved for administration and suitable for use as a medicament. Therapeutic antibodies are generally defined herein by their international nonproprietary name (INN) which is the official generic and nonproprietary name given to a pharmaceutical drug or active ingredient. Many (but not all) therapeutic antibodies are monoclonal antibodies, in particular of the IgG type.

As used herein, an "enzyme-cleavable peptide sequence" defines a peptide sequence which generates one or more quantifiable proteolytic peptides, when the said antibody-like protein is subjected to enzyme (protease) proteolysis. For instance, an enzyme-cleavable peptide sequence encompasses a trypsin-cleavable peptide sequence.

As used herein a "chimeric antibody-like protein structurally similar to a (one or more) reference therapeutic antibodies" refers to a polypeptide of the antibody type which is distinct from the said reference therapeutic antibodies, but which shares with the said therapeutic antibodies a minimal set of structural and functional characteristics:
the chimeric antibody-like protein comprises, in a hypervariable region thereof, at least one polypeptide sequence that is identical to a polypeptide sequence comprising part or all of a hypervariable region of a reference therapeutic antibody; which polypeptide sequence may be termed TADP (for Therapeutic Antibody-Derived Polypeptide) herein, and
the said TADP polypeptide sequence which is present in both (i) the chimeric antibody-like protein and (ii) in a reference therapeutic antibody to be quantified, has a similar sensitivity to enzymes within the said chimeric antibody-like protein as within the said reference therapeutic antibody, possibly because the chimeric antibody-like protein has a conformational folding that is similar to the conformational folding of the therapeutic antibody to be quantified, at least in the hypervariable region comprising the said common TADP polypeptide sequence.

As already specified, a TADP polypeptide comprises an enzyme-cleavable peptide sequence, which enzyme-cleavable peptide sequence is aimed at being quantified, in the course of performing a method of quantification of a therapeutic antibody. As it will be described in further detail in the present specification, a TADP (or "TADP polypeptide") comprises at least one enzyme-cleavable peptide sequence. However, in some embodiments, a TADP polypeptide comprises a plurality of enzyme-cleavable peptide sequences, such as a TADP polypeptide comprises 2 to 10 enzyme-cleavable peptide sequences, of which some or all enzyme-cleavable peptide sequences may be quantified in the course of performing a method of quantification of a therapeutic antibody.

A chimeric non-therapeutic antibody-like protein as described herein is thus characterized in that a polypeptide (a TADP polypeptide), of a given amino acid sequence, comprised in a hypervariable region of the said chimeric antibody-like protein, is derived from a polypeptide, of the same given amino acid sequence, which is comprised in an hypervariable region derived from a reference therapeutic antibody to be quantified.

Because, in most embodiments, a chimeric antibody-like protein described herein comprises more than one hypervariable region, the said chimeric antibody-like protein may comprise more than one TADP, each TADP being comprised in a hypervariable region thereof, and each TADP comprising at least one enzyme-cleavable peptide sequence.

Thus, a chimeric antibody-like protein as described herein comprises at least one Therapeutic Antibody-Derived Polypeptide (TADP), each TADP comprising an enzyme-cleavable peptide sequence. Each enzyme-cleavable peptide sequence comprised in a given TADP may also be termed Therapeutic Antibody-Derived Polypeptide Fragment (TADP-F) herein. Thus, after subjecting the chimeric antibody-like protein to a step of enzyme proteolysis, at least one TADP-derived TADP-F is generated, which TADP-F has the amino acid sequence of an enzyme-cleavable peptide sequence initially comprised in the said TADP.

This invention relates to a chimeric antibody-like protein, which may be also be termed a chimeric non-therapeutic antibody-like protein, which has a structure similar to a reference therapeutic antibody to be quantified, and which comprises at least one hypervariable region, and wherein
the said chimeric antibody-like protein comprises, in a hypervariable region thereof, a polypeptide consisting of part or all of a hypervariable region of the said reference therapeutic antibody, and
the said polypeptide consisting of part or all of a hypervariable region of the said reference therapeutic antibody comprises at least one enzyme-cleavable peptide sequence, such as at least one trypsin-cleavable peptide sequence.

For the sake of clarity, a chimeric antibody-like protein as described herein:
(i) in some embodiments, comprises, in a hypervariable region thereof, one TADP, and thus one or more than one TADP-F, derived from a hypervariable region of a given reference therapeutic antibody or
(ii) in some other embodiments, comprises, in a hypervariable region thereof, more than one TADP, and thus more than one TADP-F, derived from a hypervariable region of a given reference therapeutic antibody or
(iii) in some further embodiments, comprises, in distinct hypervariable regions thereof, more than one TADP, wherein each TADP comprised therein is derived from a hypervariable region of a given reference therapeutic antibody, and wherein two distinct TADPs comprised therein may be derived from a hypervariable region of two distinct reference therapeutic antibodies.

Thus, embodiments of a chimeric antibody-like protein as described herein encompass:
  a chimeric antibody-like protein comprising one TADP-F (i.e. an enzyme-cleavable peptide sequence comprised in a TADP);
  a chimeric antibody-like protein comprising more than one TADP-F, each TADP-F being comprised in a single TADP derived from a given reference therapeutic antibody,
  a chimeric antibody-like protein comprising more than one TADP-F, wherein at least two TADP-Fs are comprised in distinct TADPs derived from the same reference therapeutic antibody;
  a chimeric antibody like protein comprising more than one TADP-F, wherein at least two distinct TADP-Fs are comprised in two distinct TADPs derived from two distinct reference therapeutic antibodies, and
  a chimeric antibody-like protein comprising more than two TADP-Fs, wherein two distinct TADP-Fs are comprised in TADPs derived from the same reference therapeutic antibody, and the remaining TADP-Fs are comprised in TADPs derived from one or more distinct reference therapeutic antibodies.

Each TADP comprised in a chimeric antibody-like protein described herein generates, when the said chimeric antibody-like protein is subjected to enzyme proteolysis, one or more quantifiable proteolytic peptides, i.e. one or more quantifiable TADP-Fs.

According to some embodiments, each TADP comprised in an antibody-like protein described herein generates, when the said antibody-like protein is subjected to trypsin proteolysis, one or more tryptic peptides, i.e. one or more TADP-Fs, that are quantifiable, notably by mass spectrometry.

Thus, when (i) a reference therapeutic antibody comprising a given TADP encompassing all or part of a hypervariable region thereof and (ii) an antibody-like protein comprising the said given TADP encompassing all or part of a hypervariable region thereof, are both subjected to an enzyme proteolysis in the same proteolysis conditions, proteolytic peptides having an identical amino acid sequence are generated from the two TADP-containing molecules, respectively. As it is readily understood, a set of proteolysis peptides thus generated comprise therapeutic antibody-specific proteolysis peptides originating from both (i) the chimeric antibody-like protein and (ii) the reference therapeutic antibody.

Further, when using a chimeric antibody-like protein that is labelled, notably with a stable isotope, then (i) a proteolytic peptide generated from the said chimeric antibody-like protein may be easily discriminated from (ii) a proteolytic peptide having the same amino acid sequence and derived from the reference therapeutic antibody, for instance by mass spectrometry analysis, as it is shown in the examples herein.

Chimeric antibody-like proteins of the invention possess antigen binding properties that are distinct from the antigen binding properties of the reference therapeutic antibody, which distinct antigen binding properties are caused by the absence, in the said chimeric antibody-like antibody, of one or more hypervariable regions derived from the said reference therapeutic antibody. Illustratively, a chimeric antibody-like protein, generally does not bind the same epitope(s) and/or antigen(s) with the same specificity or the same affinity as that found in the reference therapeutic antibody. In most cases, a chimeric antibody-like protein as described herein, when compared to a corresponding reference antibody, has dramatically reduced binding properties or has even lost its ability to bind to the antigen against which a corresponding reference therapeutic antibody is directed.

Accordingly, the chimeric antibody-like protein cannot be used for therapeutic purposes because it is not identical to the reference therapeutic antibody. The chimeric antibody-like protein is thus usable for in vitro diagnostic, but is not suitable for administration as a medicament.

Accordingly, the inventors provide, as an internal standard, a chimeric antibody-like protein, that may also be termed a chimeric non-therapeutic antibody-like protein, which is structurally similar to a reference therapeutic antibody, the said chimeric antibody-like antibody protein comprising, in a hypervariable region thereof, an enzyme-cleavable peptide sequence of a hypervariable region derived from the said reference therapeutic antibody.

As already specified previously, the said "enzyme-cleavable peptide sequence comprised in a hypervariable region derived from the said reference therapeutic antibody" may also be termed TADP-F (for "Therapeutic Antibody-Derived Polypeptide Fragment") herein. Similarly, the corresponding enzyme-cleaved peptide sequence resulting from enzyme proteolysis may also be termed TADP-F herein.

Because the chimeric antibody-like protein is structurally similar to a reference therapeutic antibody, it is readily understood that the said chimeric antibody-like protein is a folded protein, and most preferably possesses the same conformational folding as that of the reference therapeutic antibody. In particular, the chimeric antibody-like peptide possesses variable regions, and thus hypervariable regions, which are folded in immunoglobulin domains.

As used herein, the "immunoglobulin domain" or "immunoglobulin-like domain", both terms having the same meaning herein, refers to a family of protein domains which exhibits considerable structural homology, and which consists of a 2-layer sandwich of about 7-9 antiparallel β-strands arranged in two β-sheets with a Greek key topology, consisting of about 70 to 110 amino acids. Immunoglobulin domains may additionally be defined as constant or variable domains. The variable domains are characterized by the presence of hypervariable loops, changes in the residues of which provide the wide antigen-binding capacity of the immune system. Constant domains do not express such hypervariability as they are not primarily involved in antigen-related interactions. As used herein, "immunoglobulin domain" is thus intended to include all such variable and constant domains, even though the ones which are primarily considered herein are variable domains.

Despite the presence or absence of hypervariable loops, immunoglobulin-like domains all exhibit common structural motifs. For example, they will each generally have about 100 amino acids, in particular about 80 amino acids, and will have a similar overall structure including antiparallel β sheets, usually stabilized by a conserved disulfide bond. The structural similarity is important as it renders the present invention applicable to all such immunoglobulin domains.

In preferred embodiments of a chimeric antibody-like protein described herein, a TADP comprised therein comprises, or in some embodiments consists of, a hypervariable region derived from a reference therapeutic antibody.

In those preferred embodiments, the introduction of hypervariable region(s) of therapeutic antibodies into the primary structure of the said antibody-like protein, while maintaining the accessibility of said hypervariable region(s) to proteases, confers the following advantages over other available internal standards in the market:

it can be reliably used as an internal standard even in the presence of a proteolysis step prior to MS analysis, due to its similarity of structure with the quantified therapeutic antibodies;

it provides higher protein sequence coverage and modularity, because of the presence of polypeptide sequences derived from hypervariable(s) regions, and also because the antibody-like protein is not required to bind to the original epitope of the quantified antibodies;

it is highly stable: degradation, precipitation or aggregation are extremely limited.

it may be used in a large variety of fields, including proteomics, quality controls in the manufacture of vaccines and other bioproducts, biological and health hazard controls, food and water controls;

it is compatible with multiplex quantification, in particular in human plasma and human serum; and it is easily manufacturable, even in the form of a stable isotope-labeled polypeptide, because therapeutic antibodies are structurally well characterized, and the production of recombinant antibodies is known in the Art.

Thus, the chimeric antibody-like protein described herein differs from QCAT proteins, which are concatemers having no ternary structure, and thus which may increase the reproducibility and/or calibration of the quantification. It also differs from PSAQ™ standards which are identical to the polypeptide (i.e. antibody) to be quantified and produced in acellular expression systems It also differs from SILU™Mab standards, which only comprise peptides derived from the constant region(s) of the antibodies to be quantified.

According to a first embodiment, the invention relates to a chimeric non-therapeutic antibody-like protein structurally similar to a reference therapeutic antibody, comprising, in a hypervariable region thereof, an enzyme-cleavable peptide sequence of a hypervariable region derived from the said reference therapeutic antibody.

In most preferred embodiments; the said chimeric non-therapeutic antibody-like protein is a labeled chimeric non-therapeutic antibody-like protein.

According to a second embodiment, the invention relates to a composition comprising a chimeric non-therapeutic antibody-like protein as defined herein.

According to a third embodiment, the invention relates to a method for quantifying one or more therapeutic antibodies in a sample comprising the steps of:

a) adding to a test sample which contains therapeutic antibodies a known amount of one or more labeled forms of the chimeric non-therapeutic antibody-like protein as defined herein, whereby a pre-proteolysis sample is provided, b) subjecting the pre-proteolysis sample to an enzyme proteolysis, so as to provide a proteolysis sample comprising (i) proteolysis labeled peptides derived from the labeled chimeric non-therapeutic antibody-like protein and (ii) proteolysis peptides derived from the therapeutic antibody contained in the test sample, c) determining by mass spectrometric analysis the ratio between (i) one or more selected proteolysis labeled peptides derived from the said chimeric non-therapeutic antibody-like protein and (ii) one or more corresponding proteolysis peptides derived from the said therapeutic antibody, d) calculating from the ratio determined at step c) the amount of the said therapeutic antibody in the test sample.

This invention further relates to a kit for quantifying therapeutic antibodies, comprising at least one chimeric non therapeutic antibody-like protein as described in the present specification.

In most preferred embodiments of the said kit, the said chimeric non therapeutic antibody-like protein is in a labelled form, and especially in a stable isotope labelled form.

In some embodiments of a kit, the chimeric non therapeutic antibody-like protein is in a purified form, either as comprised in a purified form in a liquid form such as in a liquid saline solution, or in a solid form such as in a lyophilized form.

In some other embodiments of a kit, the chimeric non therapeutic antibody-like protein is present as diluted in a protein-containing material, the thus diluted chimeric non therapeutic antibody-like protein being either in a liquid form or in a solid form such as in a lyophilized form.

In further embodiments of a kit according to the invention, the said kit also comprises a therapeutic antibody to be quantified (i.e; a reference therapeutic antibody), which serves in the said kit as a calibration standard molecule.

In some of these embodiments, the said reference therapeutic antibody is in a labelled form, and especially in a stable isotope labelled form.

In some other embodiments, the said reference therapeutic antibody is in an unlabelled form.

In some of these further embodiments, the therapeutic antibody comprised in a kit is in a purified form, either in a liquid solution or in a solid form such as in a lyophilized form. In some other of these further embodiments, the therapeutic antibody comprised in a kit is present as diluted in a protein-containing material, either in a liquid form or in a solid form such as in a lyophilized form.

In embodiments wherein the chimeric non therapeutic antibody-like protein or the therapeutic antibody is present in a form diluted in a protein-containing material, the said protein-containing material preferably mimics the protein composition of a biological sample containing the reference therapeutic antibody that will be quantified, such as a serum sample, which includes human and non-human serum samples, and especially a human serum sample.

In some of these embodiments, the chimeric non therapeutic antibody-like protein or the therapeutic antibody is diluted in human serum. Human serum is commercially available, such as in the form of pooled human serum, such as marketed by the Innovative Research company (Novi, Mich., USA) under the reference N° 888-660-6866.

In some other of these embodiments, the chimeric non therapeutic antibody-like protein or the therapeutic antibody is diluted in a serum-like protein matrix, such as in a protein matrix human serum albumin and human immunoglobulins, e.g. human IgGs. Illustrative embodiments of such a human serum-like protein matrix may comprise 60 µg/ml human serum albumin and 15 µg/ml human IgGs.

As it will be readily understood in the light of the description of the method for quantifying one or more therapeutic antibodies in the present specification, the therapeutic antibody that is contained in some embodiments of a kit according to the invention is useful as a calibration molecule that is present in a kit at a known concentration.

In some preferred of these embodiments of a kit, the said kit contains a serial of a reference therapeutic antibody-containing calibration samples. Illustratively, such preferred embodiments of a kit may contain the following serial of calibration samples: (i) control sample without reference therapeutic antibody, (ii) 5 µg/ml reference therapeutic antibody, (iii) 20 µg/ml reference therapeutic antibody, (iv) 50 µg/ml reference therapeutic antibody and (v) 100 µg/ml reference therapeutic antibody.

In some of these preferred embodiments of a kit, the control sample consists of human serum or of a human serum-like protein matrix described above.

In some of these preferred embodiments, the reference therapeutic antibody is under a labelled form, and especially under a form of the said therapeutic antibody labelled with a stable isotope.

In some preferred embodiments of a quantification kit according to the invention, the said kit comprises (i) a stable isotope-labelled chimeric non therapeutic antibody-like protein in a purified form and (i) a reference therapeutic antibody diluted in human serum or in a serum-like protein matrix, which encompasses a serial of samples of a reference therapeutic antibody of increasing known concentrations.

Thus, the present invention relates to a kit for quantifying a reference therapeutic antibody comprising at least:

the reference therapeutic antibody, either in a purified form or in a diluted form comprised in a protein-containing material, and a labeled form of a chimeric non-therapeutic antibody-like protein as defined above, either in a purified form or in a diluted form comprised in a protein-containing material.

In still further embodiments of a kit as described herein, the said kit may also comprise one or more control samples aimed at ensuring the highest accuracy and the highest reproducibility of the quantification measures of a therapeutic antibody in a sample, which control samples comprise both (i) a known concentration of a labelled chimeric non therapeutic antibody-like protein as described herein and (ii) a known concentration of a reference therapeutic antibody. In some of these still further embodiments, the said kit comprises a serial of such control samples comprising increasing concentrations of the therapeutic antibody to be quantified, and most preferably the same known concentration of the labelled chimeric non therapeutic antibody-like protein.

Illustratively, such still further embodiments of a kit described herein may comprise two of such control samples, (i) a first control sample comprising, preferably in human serum or in a human serum-like protein matrix, 20 µg/ml of a labelled chimeric non therapeutic antibody-like protein and 20 µg/ml of a therapeutic antibody to be quantified and (ii) a first control sample comprising, preferably in human serum or in a human serum-like protein matrix, 20 µg/ml of a labelled chimeric non therapeutic antibody-like protein and 80 µg/ml of a therapeutic antibody to be quantified.

As it is readily understood, according to these still further embodiments, a kit may comprise more than two of these control samples, for example may comprise 3, 4, 5, 6, 7, 8, 9 or 10, or in some embodiments more than 10 of these control samples.

As it is described throughout the present specification, a chimeric non therapeutic antibody-like protein may, in some embodiments, be used for quantifying more than one reference therapeutic antibody, for example may be used for quantifying two distinct therapeutic antibodies. In these embodiments, there may be used a chimeric non therapeutic antibody-like protein comprising, (i) in a first hypervariable region thereof, a polypeptide (i.e. a TADP as also termed herein) comprising an enzyme-cleavable peptide sequence (i.e. a TADP-F as also termed herein) derived from a hypervariable region of a first therapeutic antibody to be quantified and further comprising (ii) in a second hypervariable region thereof, a polypeptide (i.e. a TADP as also termed herein) comprising an enzyme-cleavable peptide sequence (i.e. a TADP-F as also termed herein) derived from a hypervariable region of a second therapeutic antibody to be quantified.

Thus, in some embodiments of a kit according to the invention, such a kit may comprise either (i) a plurality of calibration samples, or serials of calibration samples, wherein each calibration sample comprises, at known amounts, only one of each therapeutic antibody to be quantified, or (ii) a plurality of calibration samples, or a serial of calibration samples, wherein each calibration sample comprises, at known amounts, a combination of a plurality of the therapeutic antibodies to be quantified, such as a combination of all (i.e. two) the therapeutic antibodies to be quantified.

In such embodiments wherein a kit is designed to quantify more than one therapeutic antibody, the said kit may also further comprise control samples comprising a mixture of (i) a known concentration of a labelled chimeric non therapeutic antibody-like protein and (ii) a known amount of a plurality of the therapeutic antibodies to be quantified, such as a known amount of each of the two therapeutic antibodies to be quantified.

An illustrative example of such a kit suitable for quantifying a plurality of therapeutic antibodies encompass a kit suitable for quantifying Nivolumab and Ipilimumab.

In such an illustrative kit, the labelled chimeric non therapeutic antibody-like protein comprises (i) in a first hypervariable region thereof, a first polypeptide (i.e. a first TADP as also termed herein) derived from a hypervariable region of nivolumab and (ii) in a second hypervariable region thereof, a second polypeptide (i.e. a second TADP as also termed herein) derived from a hypervariable region of ipilimumab. Indeed, in some embodiments of a relevant labelled chimeric non therapeutic antibody-like protein, the said antibody-like protein may comprise, in selected respective hypervariable regions thereof, more than one TADP derived from nivolumab and/or more than one TADP derived from Ipilimumab, with one TADP comprised in each selected hypervariable region thereof.

According to a further aspect, this invention relates to a use of a polypeptide derived from a hypervariable region of a therapeutic antibody (i.e. a TADP as also termed herein), which polypeptide comprises an enzyme-cleavable peptide sequence (i.e. a TADP-F as also termed herein) for the preparation of a chimeric non-therapeutic antibody-like protein as described herein.

In some embodiments, wherein the chimeric non-therapeutic antibody-like protein is suitable for quantifying a plurality of therapeutic antibodies, this invention further pertains to a use of a plurality of polypeptides, wherein two of these polypeptides derive from a hypervariable region of two distinct therapeutic antibodies, for the preparation of a chimeric non-therapeutic antibody-like protein as described herein.

According to a further aspect, the invention relates to a use of at least one polypeptide derived from hypervariable(s) region(s) of one or more therapeutic antibodies, for the preparation of a chimeric non-therapeutic antibody-like protein as described herein.

According to a sixth embodiment, the invention relates to a nucleic acid coding for a polypeptide comprising a sequence selected from the group consisting of: SEQ ID No1 to 12 and SEQ ID No113 to 119.

As used herein, the expression "comprises" or "comprising" encompasses also "consists of" or "consisting of".

As used herein, the expression "a" or "at least one" encompasses "one", or "more than one"; which encompasses a "plurality", such as two, or more than two, which may encompass, three, four, five, six or even more than six.

As used herein, the term "antibody" or "immunoglobulin" have the same meaning, and will be used equally in the present invention. The term "antibody" as used herein refers to folded immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments.

In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, trans-placental mobility, complement binding, and binding to Fc receptors (FcR).

The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. The term "antibody" may also include "single-chain" (or "single-domain") antibodies, and "heavy-chain antibodies" (VHH or VNAR antibodies) also referred herein as "non-conventional antibodies" which are found in camelids and sharks.

As used herein, the terms "variable region" and "variable domain" have the same meaning, and will be used equally in the present invention.

As used herein, the terms "hypervariable region", "hypervariable domain" and "Complementarily Determining Regions (CDRs)" have the same meaning, and will be used equally in the present invention. Hypervariable regions are necessarily part of variable regions.

As used herein the term "single domain antibody" has its general meaning in the art and refers to the single heavy chain variable domain of antibodies of the type that can be found in Camelid mammals which are naturally devoid of light chains. Such single domain antibody are also called VHH or "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388.

As used herein, a "human antibody" is intended to include antibodies having variable and constant regions derived from human immunoglobulin sequences. The human antibodies of the present invention may include amino acid residues not encoded by human immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, a "humanized antibody" refers to an antibody having variable region framework and constant regions from a human antibody but retains the CDRs of a previous non-human antibody.

As used herein, a "chimeric antibody" refers to an antibody which comprises a VH domain and a VL domain of a non-human antibody, and a CH domain and a CL domain of a human antibody.

As used herein, a "synthetic antibody" refers to an entirely in vitro engineered molecule which comprises at least fragments of a variable region of an antibody. Synthetic antibodies, in the sense of the invention, may thus also be antigen-binding fragments selected from the group consisting of a Fab, a F(ab)'2, a single domain antibody (sdAb), a ScFv, a Fab-scFv, a ScFv-Fc, a Sc(Fv)2, a diabody, a di-diabody, a triabody, a tetrabody, a pentabody, an unibody, a minibody, a maxibody, a small modular immunopharmaceutical (SMIP), and fragments which comprise variable regions such as variable light (VL) and variable heavy (HL) chains. Examples of engineered multivalent antibodies which are also considered as antibodies herein are listed in Nuñez-Prado et al. ("*The coming of age of engineered multivalent antibodies*"; Drug Discovery Today; Vol. 0, N°0; 2015).

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope.

As used herein, the term "specificity" refers to the ability of an antibody to detectably bind an epitope presented on an antigen while having relatively little detectable reactivity with non-antigen proteins or structures. Specificity can be relatively determined by binding or competitive binding assays, using, e.g., Biacore instruments, a described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules.

As used herein, the term "affinity", as used herein, means the strength of the binding of an antibody to an epitope. The affinity of an antibody is given by the dissociation constant Kd, defined as $[Ab] \times [Ag]/[Ab-Ag]$, where $[Ab-Ag]$ is the molar concentration of the antibody-antigen complex, $[Ab]$ is the molar concentration of the unbound antibody and $[Ag]$ is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

As used herein, the expression "stable isotope-labeled" or "labeled with a stable isotope" polypeptide (i.e. an antibody or an antibody-like protein) refers to a polypeptide whose chemical structure (i.e. primary structure), except for the presence of isotope, is identical to the non-labeled polypeptide.

Therapeutic antibodies may be selected from a group comprising or consisting of: non-human antibodies, human antibodies, humanized antibodies, synthetic antibodies, and chimeric antibodies.

Therapeutic antibodies which are considered by the invention include antibodies suitable for use as a medicament in a human or non-human individual.

Therapeutic antibodies may be selected from the group consisting of therapeutic antibodies used in inflammation, therapeutic antibodies used in oncology and also immunotherapies. Also, therapeutic antibodies may be selected from the group consisting of: anti-TNF antibodies, anti-VEGF antibodies, anti-EGFR antibodies, anti-PD-1 antibodies, anti-HER2 antibodies, anti-CD20 antibodies, anti-IL17 antibodies, and anti-CTLA4 antibodies, anti-PDL1, anti-CD25, anti-α4integrin, anti-IL6R, anti-C5, anti-IL1, anti-TPO, anti-IL12/23, anti-EPCAM/CD3, anti-CD30, anti-CD80/86, anti-anthrax, anti-CCR4, anti-CD6, anti-CD19, anti-α4β7, anti-IL6, anti-VEGFR-2, anti-SLAMF7, anti-GD2, anti-IL17A, anti-PCSK9, anti-IL5, anti-CD22, anti-IL4, anti-PDGFRα, anti-IL17RA and anti-TcdB In particular, therapeutic antibodies may be selected from the group consisting of: Infliximab, Adalimumab, Rituximab, Golimumab, Vedolizumab, Certolizumab, Etanercept, Secukinumab, Cetuximab, Bevacizumab, Nivolumab, Ipilimumab, Atezolizumab, Durvalumab, Avelumab, Trastuzumab, Pertuzumab, Panitumumab and Natalizumab, Pembrolizumab, and preferably Ipilimumab, Nivolumab, Atezolimumab, Durvalumab, Pembrolizumab, Avelumab.

Amino acid sequences of therapeutic antibodies are available to the one skilled in the art and are described in various sequence databases, which include the well-known IMGT database. Illustratively, references the IMGT database of the amino acid sequences of some of the therapeutic antibodies listed in the present specification are given in the Table hereunder.

TABLE

| Therapeutic antibodies aa sequence reference in the IMGT database | |
|---|---|
| Anticorps ou protéine de fusion | Référence IMGT (IMGT/mAbDB ID) |
| Infliximab | 156 |
| Adalimumab | 165 |
| Rituximab | 161 |
| Golimumab | 175 |
| Vedolizumab | 300 |
| Certolizumab | 242 |
| Etanercept | 216 |
| Secukinumab | 326 |

TABLE-continued

| Therapeutic antibodies aa sequence reference in the IMGT database | |
|---|---|
| Anticorps ou protéine de fusion | Référence IMGT (IMGT/mAbDB ID) |
| Cetuximab | 151 |
| Bevacizumab | 24 |
| Pembrolizumab | 472 |
| Nivolumab | 424 |
| Ipilimumab | 180 |
| Atezolizumab | 526 |
| Durvalumab | 528 |
| Avelumab | 512 |
| Trastuzumab | 97 |
| Pertuzumab | 80 |
| Panitumumab | 196 |
| Natalizumab | 75 |

According to an exemplary embodiment, all the antibody-like proteins of the invention are also considered in a labeled form, and more particularly a form labeled with a stable isotope.

The embodiments of the invention will be further defined here below.

Chimeric Antibody-Like Proteins and Compositions Comprising the Same

As already specified elsewhere herein, this invention pertains to a chimeric non-therapeutic antibody-like protein comprising, in a hypervariable region thereof, an enzyme-cleavable peptide sequence of a hypervariable region derived from the said reference therapeutic antibody.

Most preferred embodiments of a chimeric non-therapeutic antibody-like protein are labeled forms thereof.

This invention relates to a chimeric non-therapeutic antibody-like protein structurally similar a reference therapeutic antibody, comprising, in a hypervariable region thereof, an enzyme-cleavable peptide sequence of a hypervariable region derived from the said reference therapeutic antibody.

A chimeric non-therapeutic antibody-like protein of the invention thus differs from a reference therapeutic antibody by at least one hypervariable region.

Thus, compared to the said reference therapeutic antibody, a chimeric non-therapeutic antibody-like protein according to the invention does not bind the same epitope(s) or antigen(s) with the same specificity nor the same affinity.

That is because the recognition of one epitope or antigen by a therapeutic antibody generally requires the spatial integrity of all hypervariable regions of said therapeutic antibody.

Accordingly, because chimeric antibody-like proteins according to the invention generally do not bind to the same epitope(s) or antigen(s), those chimeric antibody-like polypeptides also do not cross-compete with a corresponding reference therapeutic antibody for its binding to a given target antigen or to a given target antigen epitope.

Chimeric antibody-like proteins according to the invention are modulable and compatible both with uniplex and multiplex analysis, the latter consisting in quantifying the level of a plurality of therapeutic antibodies in a same quantification experiment.

Thus, the chimeric antibody-like peptide can be used as an internal standard for quantifying one reference therapeutic antibody, by having hypervariable region(s) comprising one or more polypeptide sequences derived from hypervariables regions of the said reference therapeutic antibody. Accordingly, the chimeric non-therapeutic antibody-like protein is structurally similar to one reference therapeutic antibody, comprising, in a hypervariable region thereof, an enzyme-cleavable peptide sequence of a hypervariable region derived from the said reference therapeutic antibody.

Thus, according to a particular embodiment, the chimeric antibody-like protein has at least one hypervariable region comprising at least one polypeptide sequence (i.e. TADP) derived from hypervariable(s) region(s) of a reference therapeutic antibody.

Alternatively, the chimeric antibody-like peptide can be used as an internal standard for quantifying more than one reference therapeutic antibody. According to one embodiment, the antibody-like protein is thus structurally similar to each therapeutic antibody of a set of reference therapeutic antibodies, and comprises a plurality of enzyme-cleavable peptide sequences, and at least one enzyme-cleavable peptide sequence of a hypervariable region derived from each one of the said plurality of reference therapeutic antibodies.

Thus, the chimeric antibody-like protein can also be used as an internal standard for quantifying a plurality of reference therapeutic antibodies, by having hypervariable regions comprising a plurality of polypeptide sequences derived from hypervariable regions of said plurality of reference therapeutic antibodies.

Thus, according to a particular embodiment, the chimeric antibody-like protein has at least one hypervariable region comprising at least one polypeptide sequence (i.e. TADP) derived from hypervariable(s) region(s) of a plurality of reference therapeutic antibodies.

According to some embodiments, the at least one hypervariable region of said antibody-like protein comprises at least one polypeptide sequence (i.e. TADP) derived from a hypervariable region of each one of a plurality of reference therapeutic antibody.

Most preferably, the polypeptide sequence (i.e. TADP) derived from a hypervariable region consists of a sequence derived from a hypervariable region of the reference therapeutic antibody.

According to such an embodiment, at least one hypervariable region of the said chimeric antibody-like protein comprises at least one polypeptide sequence (i.e. TADP) derived from a hypervariable region of each one of the one or more reference therapeutic antibodies.

Thus, a chimeric antibody-like polypeptide as described herein encompasses notably the following embodiments:
- an antibody-like protein of the type "1×TADP", which comprises only one TADP in a hypervariable region thereof;
- an antibody-like protein of the type "2×TADP", which comprises two TADPs, each TADP being comprised in a hypervariable region thereof, and wherein either (i) the two TADPs derive from the same reference therapeutic antibody or (ii) the two TADPs derive from distinct reference therapeutic antibodies;
- an antibody-like protein of the type "3×TADP", which comprises three TDAPs each TADP being comprised in a hypervariable region thereof, and wherein (i) the three TADPs derive from the same reference therapeutic antibody, or (ii) two TADPs derive from the a first reference therapeutic antibody and the remaining TADP derives from a second reference therapeutic antibody, or (iii) the three TADPs derive from three distinct reference therapeutic antibodies.

It is readily appreciated that further embodiments of chimeric antibody-like proteins are encompassed herein, notably depending on the antibody format of the reference therapeutic antibody(ies) and in some aspects also according to the antibody format of the chimeric antibody-like protein.

Notably, embodiments of a chimeric antibody-like protein may vary depending of the number of hypervariable regions comprised in the reference therapeutic antibody(ies), and also possibly of the number of hypervariable regions comprised in the antibody-like protein format that has been selected.

Thus, chimeric antibody-like proteins described herein also encompass those of the "×4TADP", "×5TADP", "×6TADP", "7×TADP", "8×TADP", "9×TADP", "10× TADP", "11×TADP" and "12×TADP", depending notably on the number of hypervariable regions comprised in the reference therapeutic antibody(ies).

In most preferred embodiments, a chimeric antibody-like protein as described herein has the same antibody format as the reference therapeutic antibody(ies).

According to the most conventional embodiment, a reference therapeutic antibody has two light chains and two heavy chains, each light chain comprising three hypervariable regions and each heavy chain comprising three hypervariable regions.

According to this most conventional embodiment, a most preferred chimeric antibody-like protein is an antibody having two light chains and two heavy chains, each light chain comprising three hypervariable regions and each heavy chain comprising three hypervariable regions, and wherein the said antibody-like antibody comprises a TADP in one, or alternatively in more than one, hypervariable region thereof.

Indeed, according to such most conventional embodiment, the said antibody-like protein may comprise up to twelve TADP-s, either deriving from the same reference therapeutic antibody or (ii) part of these TADPs derive from distinct reference therapeutic antibodies or (iii) all TADPs derive from distinct reference therapeutic antibodies.

Figure 2A:
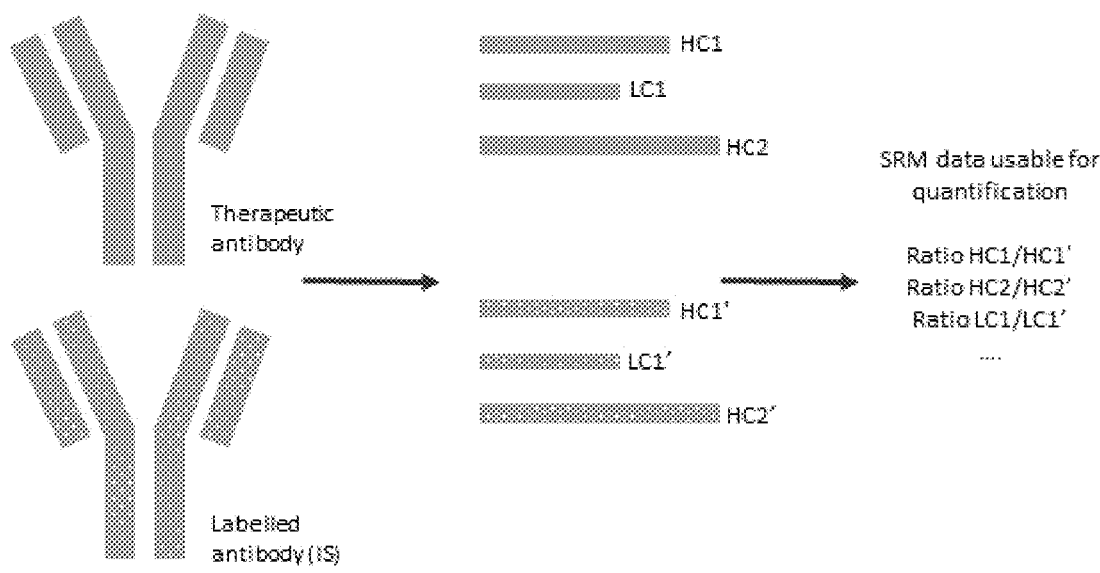
FIG. 2A: Quantification of mAb-Classic approach. In this approach, the antibody to quantify is a therapeutic antibody and the internal antibody standard (IS) used as quantification standard is the labelled version of the therapeutic antibody, having exactly the same amino acid sequences.
Figure 2B:
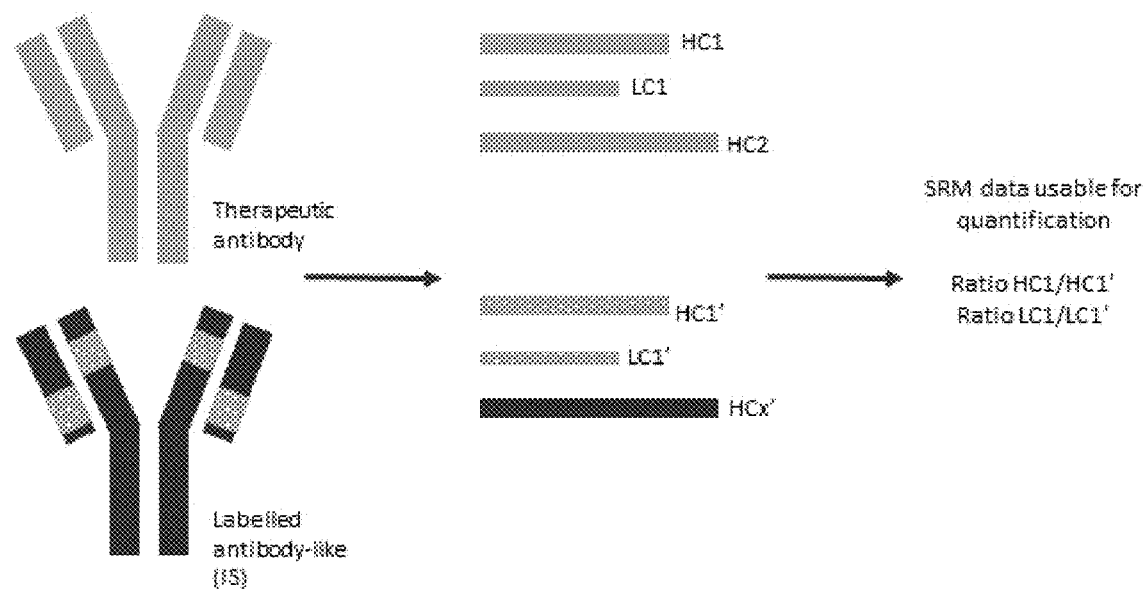
FIG. 2B: Quantification of mAb-Antibody-like approach. In this approach, the antibody to quantify is a therapeutic antibody and the internal antibody standard used as quantification standard is a labelled antibody containing at least one proteotypic peptide of the therapeutic antibody
Figure 2C:
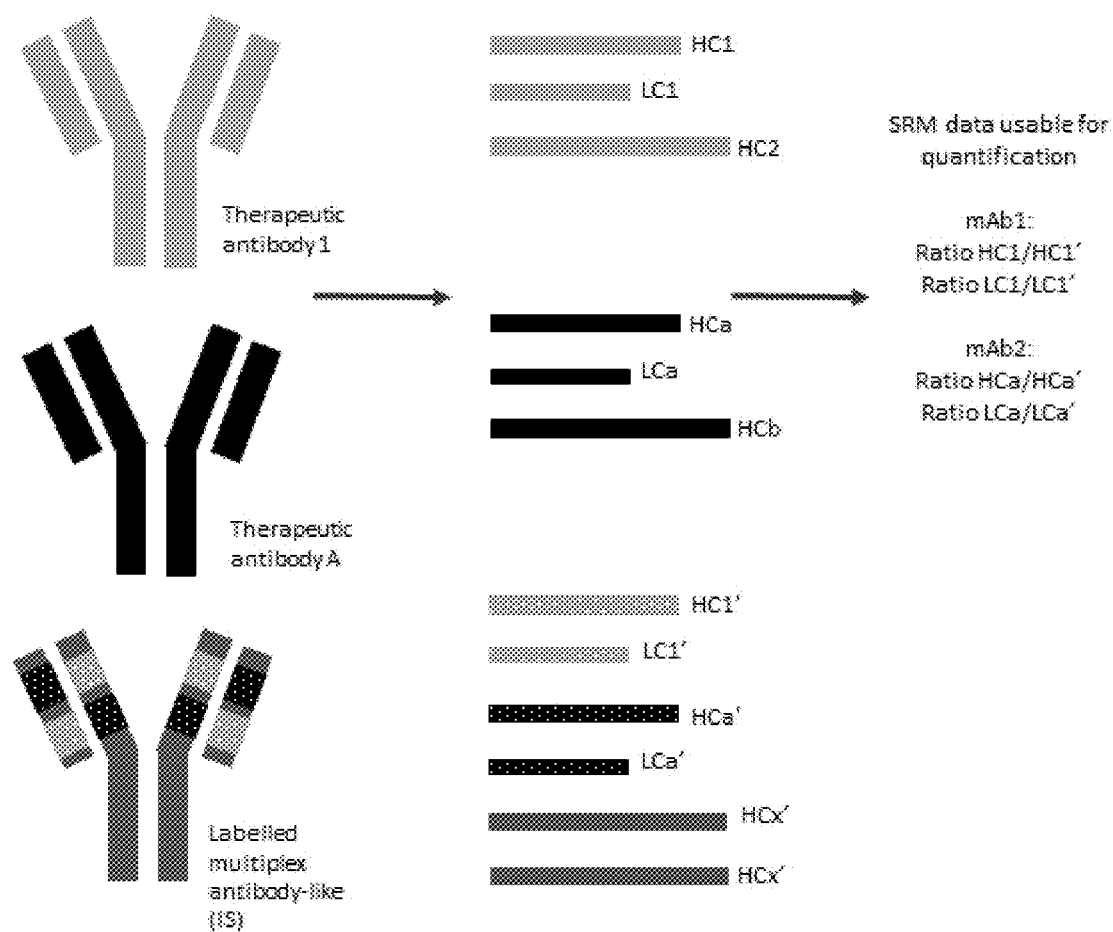
FIG. 2C: Quantification of mAb-Multiplex antibody-like approach. In this approach, at least two therapeutic antibody can be quantified. The internal antibody standard (IS) used as quantification standard is a symmetric labelled antibody containing at least one proteotypic peptide of each therapeutic antibody. This strategy can be adapted to quantify more than 2 different therapeutic antibodies.
Figure 2D:
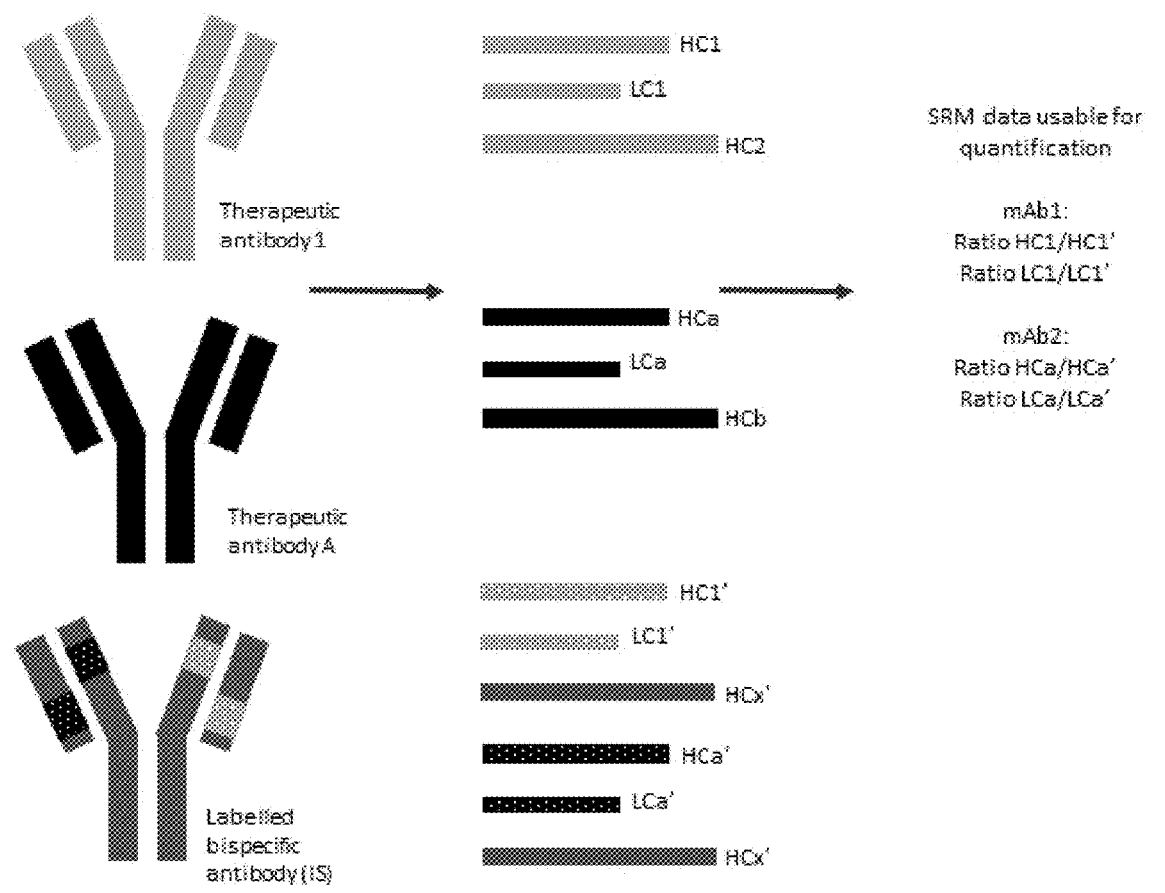
FIG. 2D: Quantification of mAb-Bispecific antibody-like approach. In this approach, two therapeutic antibodies can be quantified simultaneously using a single internal antibody quantification standard. It is a labelled bispecific antibody containing at least one proteotypic peptide of each therapeutic antibody.

A chimeric antibody-like protein according to the invention may thus be as described in FIG. 2B, 2C or 2D.

According to one embodiment, the chimeric non-therapeutic antibody-like protein has at least one hypervariable region comprising more than one polypeptide sequence (i.e. TADP) derived from hypervariable(s) region(s) of a plurality of reference therapeutic antibodies.

According to some embodiments, the said one or more reference therapeutic antibodies are selected from the group consisting of: human antibodies, humanized antibodies, bispecific antibodies, chimeric antibodies, Fab, and single domain antibodies (also called nanobodies).

According to some embodiments, the antibody-like protein is structurally similar to one or more reference therapeutic antibodies selected from the group consisting of: anti-TNF antibodies, anti-VEGF antibodies, anti-EGFR antibodies, anti-PD-1 antibodies, anti-HER2 antibodies, anti-CD20 antibodies, anti-IL17 antibodies, and anti-CTLA4 antibodies, anti-PDL1, anti-CD25, anti-α4integrin, anti-IL6R, anti-C5, anti-IL1, anti-TPO, anti-IL12/23, anti-EPCAM/CD3, anti-CD30, anti-CD80/86, anti-anthrax, anti-CCR4, anti-CD6, anti-CD19, anti-α4β7, anti-IL6, anti-VEGFR-2, anti-SLAMF7, anti-GD2, anti-IL17A, anti-PCSK9, anti-IL5, anti-CD22, anti-IL4, anti-PDGFRα, anti-IL17RA and anti-TcdB.

Each-one of the above-defined reference therapeutic antibodies is thus defined by its specificity towards one antigen (i.e. TNF for anti-TNF antibodies).

Illustratively, the reference therapeutic antibodies, or combinations thereof (including at least two reference therapeutic antibodies) described herein may be selected in a group consisting of: Abagovomab, Abatacept, Abciximab, Abituzumab, Abrilumab, Actoxumab, Adalimumab, Adecatumab, Aducanumab, Aflibercept, Afutuzymab, Alacizumab, Alefacept, Alemtuzumab, Alirocumab, Altumomab, Amatixumab, Anatumomab, Anetumab, Anifromumab, Anrukinzumab, Apolizumab, Arcitumomab, Ascrinvacumab, Aselizumab, Atezolizumab, Atinumab, Altizumab, Atorolimumab, Bapineuzumab, Basiliximab, Bavituximab, Bectumomab, Begelomab, Belatacept, Belimumab, Benralizumab, Bertilimumab, Besilesomab, Bevacizumab, Bezlotoxumab, Biciromab, Bimagrumab, Bimekizumab, Bivatuzumab, Blinatumomab, Blosozumab, Bococizumab, Brentuximab, Briakimumab, Brodalumab, Brolucizumab, Bronticizumab, Canakinumab, Cantuzumab, Caplacizumab, Capromab, Carlumab, Catumaxomab, Cedelizumab, Certolizumab, Cetuximab, Citatuzumab, Cixutumumab, Clazakizumab, Clenoliximab, Clivatuzumab, Codrituzumab, Coltuximab, Conatumumab, Concizumab, Crenezumab, Dacetuzumab, Daclizumab, Dalotuzumab, Dapirolizumab, Daratumumab, Dectrekumab, Demcizumab, Denintuzumab, Denosumab, Derlotixumab, Detumomab, Dinutuximab, Diridavumab, Dorlinomab, Drozitumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Enavatuzumab, Enfortumab, Enlimomab, Enoblituzumab, Enokizumab, Enoticumab, Ensituximab, Epitumomab, Epratuzomab, Erlizumab, Ertumaxomab, Etaracizumab, Etrolizumab, Evinacumab, Evolocumab, Exbivirumab, Fanolesomab, Faralimomab, Farletuzomab, Fasimumab, Felvizumab, Fezkimumab, Ficlatuzumab, Figitumumab, Firivumab, Flanvotumab, Fletikumab, Fontolizumab, Foralumab, Foravirumab, Fresolimumab, Fulramumab, Futuximab, Galiximab, Ganitumab, Gantenerumab, Gavilimomab, Gemtuzumab, Gevokizumab, Girentuximab, Glembatumumab, Golimumab, Gomiliximab, Guselkumab, Ibalizumab, Ibritumomab, Icrucumab, Idarucizumab, Igovomab, Imalumab, Imciromab, Imgatuzumab, Inclacumab, Indatuximab, Indusatumab, Infliximab, Intetumumab, Inolimomab, Inotuzumab, Ipilimumab, Iratumumab, Isatuximab, Itolizumab, Ixekizumab, Keliximab, Labetuzumab, Lambrolizumab, Lampalizumab, Lebrikizumab, Lemalesomab, Lenzilumab, Lerdelimumab, Lexatumumab, Libivirumab, Lifastuzumab, Ligelizumab, Lilotomab, Lintuzumab, Lirilumab, Lodelcizumab, Lokivetmab, Lorvotuzumab, Lucatumumab, Lulizumab, Lumiliximab, Lumretuzumab, Mapatumumab, Margetuximab, Maslimomab, Mavrilimumab, Matuzumab, Mepolizumab, Metelimumab, Milatuzumab, Minetumomab, Mirvetuximab, Mitumomab, Mogamulizumab, Morolimumab, Motavizumab, Moxetumomab, Muromonab-CD3, Nacolomab, Namilumab, Naptumomab, Narnatumab, Natalizumab, Nebacumab, Necitumumab, Nemolizumab, Nerelimomab, Nesvacumab, Nimotuzumab, Nivolumab, Nofetumomab, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab, Oregovomab, Orticumab, Otelixizumab, Oltertuzumab, Oxelumab, Ozanezumab, Ozoralizumab, Pagibaximab, Palivizumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab, Pintumomab, Polatuzumab, Ponezumab, Priliximab, Pritumumab, Quilizumab, Racotumomab, Radretumab, Rafivirumab, Ralpancizumab, Ramucirumab, Ranibizumab, Raxibacumab, Refanezumab, Regavirumab, Reslizumab, Rilonacept, Rilotumumab, Rinucumab, Rituximab, Robatumumab, Roledumab, Romosozumab, Rontalizumab, Rovelizumab, Ruplizumab, Sacituzumab, Samalizumab, Sarilumab, Satumomab, Secukimumab, Seribantumab, Setoxaximab, Sevirumab, Sibrotuzumab, Sifalimumab, Siltuximab, Siplizumab, Sirukumab, Sofituzumab, Solanezumab, Solitomab, Sonepcizumab, Sontuzumab, Stamulumab, Sulesomab, Suvizumab, Tabalumab, Tacatuzumab, Tadocizumab, Talizumab, Tanezumab, Taplitumomab, Tarextumab, Tefibazumab, Telimomab aritox, Tenatumomab, Teneliximab, Teplizumab, Tesidolumab, TGN 1412, Ticlimumab, Tildrakizumab, Tigatuzumab, TNX-650, Tocilizumab, Toralizumab, Tosatoxumab, Tositumomab, Tovetumab, Tralokimumab, Trastuzumab, TRBS07, Tregalizumab, Tremelimumab, Trevogrumab, Tucotuzumab, Tuvirumab, Ublituximab, Ulocuplumab, Urelumab, Urtoxazumab, Ustekimumab, Vandortuzumab, Vantictumab, Vanucizumab, Vapaliximab, Varlimumab, Vatelizumab, Vedolizumab, Veltuzumab, Vepalimomab, Vesencumab, Visilizumab, Volociximab, Vorsetuzumab, Votumumab, Zalutumimab, Zanolimumab, Zatuximab, Ziralimumab, Ziv-Aflibercept, and Zolimomab.

According to some embodiments, the chimeric antibody-like protein is structurally similar to one or more reference therapeutic antibodies selected from the group consisting of: Infliximab, Adalimumab, Rituximab, Golimumab, Vedolizumab, Certolizumab, Etanercept, Secukinumab, Cetuximab, Bevacizumab, Nivolumab, Ipilimumab, Atezolizumab, Durvalumab, Avelumab, Trastuzumab, Pertuzumab, Panitumumab, Natalizumab, Pembrolizumab, and preferably Ipilimumab, Nivolumab, Atezolimumab, Durvalumab, Pembrolizumab, Avelumab.

According to some embodiments, the chimeric antibody-like protein is structurally similar to one or more reference therapeutic antibodies selected from the group consisting of: Cetuximab, Bevacizumab, Trastuzumab, Nivolumab, Infliximab, Secukinumab, Adalimumab, Certolizumab, Golimumab, Rituximab, Ipilimumab; and preferably Cetuximab, Bevacizumab, Nivolumab and Ipilimumab.

In particular, each one of the above-mentioned therapeutic antibodies may be selected from the list so that the antibody-like protein shares structural similarity with all reference therapeutic antibodies.

Any one of the above-described chimeric antibody-like proteins, according to the invention, necessarily comprises at least one hypervariable region comprising at least one polypeptide sequence (i.e. TADP) derived from variable(s) region(s) of said one or more reference therapeutic antibodies.

According to some embodiments, the said antibody-like protein comprises at least one hypervariable region comprising polypeptide sequences (i.e. TADPs) derived from hypervariable(s) region(s) of a plurality of reference therapeutic antibodies.

The combination of at least two therapeutic antibody selected in the list below are particularly considered: muromomab, nebacumab, abciximab, edrecolomab, rituximab, basoliximab, daclizumab, palivizumab, infliximab, trastuzumab, gemtuzumab ozogamicin, alemtuzumab, ibritumomab tiuxetan, adalimumab, tositumomab, omalizumab, efalizumab, cetuximab, bevacizumab, natalizumab, ranibizumab, panitumumab, eculizumab, certolizumab, golimumab, catumaxomab, ustekinumab, canakinumab, ofatumumab, denosumab, brentuximab vedotin, belimumab, ipilimumab, raxibacumab, pertuzumab, magamulizumab, itolizumab, trastuzumab-entansine, obinutuzumab, ramucirumab, siltuximab, vedolizumab, nivolumab, pembrolizumab, blinatumomab, daratumumab, elotuzumab, necitumumab, secukinumab, dinutuximab, evolocumab, alirocumab, idarucizumab, mepolizumab, obiltoxaximab, ixekizumab, reslizumab, atezolizumab, bezlotoximab, daclizumab, brodalumab, ocrelizumab, olaratumomab, sarilumab, dupilumab, inotuzumab ozogamicin, avelumab, durvalumab.

An illustrative chimeric non therapeutic antibody-like protein of interest comprises (i) at least an enzyme-cleavable polypeptide derived from a hypervariable region of nivolumab and (ii) at least an enzyme-cleavable polypeptide derived from a hypervariable region of ipilimumab. Embodiments of such an illustrative antibody-like protein comprise (i) in a first hypervariable region thereof, an enzyme-cleavable polypeptide derived from a hypervariable region of Nivolumab and (ii) in a second hypervariable region thereof, an enzyme-cleavable polypeptide derived from a hypervariable region of Ipilimumab.

For reference, the heavy and light chains including the respective variable regions ($V_H$ and $V_L$) of above-mentioned therapeutic antibodies are defined in the sequence listing under SEQ ID No13 to 34.

Thus, according to said embodiment, the said chimeric antibody-like protein may comprise at least one hypervariable region comprising polypeptide sequences (i.e. TADPs) derived from hypervariable(s) region(s) of a plurality of reference therapeutic antibodies selected from at least the above list.

Still, according to a preferred embodiment, the said chimeric antibody-like protein comprises polypeptide sequences (i.e. TADPs) derived from hypervariable(s) region(s) selected from a list consisting of: Nivolumab, Ipilimumab, Cetuximab, Bevacizumab and Trastuzumab.

Still, according to a preferred embodiment, the said chimeric antibody-like protein comprises polypeptide sequences (i.e. TADPs) derived from hypervariable(s) region(s) selected from Nivolumab and Ipilimumab.

According to one exemplary embodiment, the said chimeric antibody-like protein comprises polypeptide sequences (i.e. TADPs) derived from hypervariable(s) region(s) selected from Cetuximab and Bevacizumab.

According to one exemplary embodiment, the said chimeric antibody-like protein comprises polypeptide sequences (i.e. TADPs) derived from hypervariable(s) region(s) selected from Trastuzumab and Cetuximab.

According to one exemplary embodiment, the said chimeric antibody-like protein comprises polypeptide sequences (i.e. TADPs) derived from hypervariable(s) region(s) selected from Trastuzumab and Bevacizumab.

As it is readily understood, a chimeric non therapeutic antibody-like protein as described herein comprises an antibody structure wherein, in at least one hypervariable region thereof, an exogenous polypeptide derived from a hypervariable region of a reference therapeutic antibody has replaced a polypeptide of approximately the same amino acid length, or of exactly the same amino acid length, initially present in the hypervariable region.

According to some embodiments, the chimeric antibody-like protein is structurally similar to an antibody selected from the group consisting of: a IgG, a IgM, a IgE, a IgA or a IgD antibody; in particular a IgG antibody, which includes an IgG1, IgG2, IgG3 and Ig4 antibody.

According to a preferred embodiment, the chimeric antibody-like protein is structurally similar to an IgG1 or IgG4 antibody.

Yet, even though many reference therapeutic antibodies (such as the ones disclosed above) are conventional antibodies belonging to a IgG, a IgM, a IgE, a IgA or a IgD isotype, and more particularly a IgG isotype (i.e. a IgG1 or IgG4 isotype), the man skilled in the Art will understand from the above that the invention is not restricted only to chimeric non-therapeutic antibody-like proteins structurally similar to said conventional antibodies; but may also extend to chimeric non-therapeutic antibody-like proteins structurally similar to non-conventional antibodies, such as single-domain antibodies or heavy-chain antibodies including VHH and VNAR antibodies.

Accordingly, all the present embodiments can be readily combined to the extent that the chimeric antibody-like protein remains structurally similar to the reference therapeutic antibody, or a combination thereof.

According to some embodiments, the chimeric antibody-like protein has one variable region and one constant region.

According to some embodiments, the chimeric antibody-like protein has at least one variable region and at least one constant region.

When the therapeutic antibodies to be quantified are conventional antibodies, they can be characterized by the presence of two variable regions and two constant regions. Thus, according to some embodiments, the structurally similar chimeric antibody-like protein has two variable regions and two constant regions.

When the therapeutic antibodies to be quantified are non-conventional antibodies, the number of variable and constant regions may differ. For instance, the therapeutic antibodies to be quantified may be selected from the group of synthetic antibodies, such as those consisting of: a ScFv, a dsFv, a diabody, a triabody, a tetrabody, a pentabody, an unibody, a minibody, a maxibody, and the like.

According to some embodiments, the chimeric antibody-like protein has no constant region.

According to some embodiments, the chimeric antibody-like protein is a heterodimer having two different heavy chains.

According to some embodiments, the chimeric antibody-like protein has two different Fab.

According to some embodiments, the chimeric antibody-like protein has either no light chain (i.e. an antibody-like protein structurally similar to a VHH or a VNAR) or no heavy chain.

According to some embodiments, the chimeric antibody-like protein is a homodimer or a heterodimer.

Accordingly, the man skilled in the Art will readily derive from the above lists the combinations of therapeutic antibodies which can be considered for the preparation and identification of a chimeric antibody-like protein according to the invention.

According to some embodiments, the polypeptide sequence(s) (i.e. TADPs) derived from the hypervariable regions of said one or more reference therapeutic antibodies are:

in the hypervariable region of a heavy chain of said antibody-like protein; and/or in the hypervariable region of a light chain of said antibody-like protein.

In particular, the antibody-like protein is characterized by a polypeptide sequence (i.e. TADP) comprised in a hypervariable region which is derived from the respective hypervariable region of the said one or more reference therapeutic antibodies (i.e. the therapeutic antibodies disclosed herein, and combinations thereof).

According to one embodiment, the chimeric non-therapeutic antibody-like protein is characterized in that a hypervariable region of the said chimeric antibody-like protein comprises one polypeptide sequence (i.e. TADP) derived from a hypervariable region for each reference therapeutic antibody.

According to one embodiment, the chimeric non-therapeutic antibody-like protein is characterized in that a hypervariable region of the said chimeric antibody-like protein comprises more than one polypeptide sequence (i.e. TADP) derived from a hypervariable region for at least one reference therapeutic antibody According to some particular embodiments, the polypeptide sequence(s) (i.e. TADPs) derived from a hypervariable region of the said one or more reference therapeutic antibodies are in the variable region of a heavy chain of the said chimeric antibody-like protein.

According to some preferred embodiments, the one or more polypeptide sequence(s) (i.e. TADPs) derived from a hypervariable region said one or more reference therapeutic antibodies are in the variable region of each heavy chain of said chimeric antibody-like protein.

According to some embodiments, the chimeric antibody-like protein comprises at least one (which includes one or more than one) variable region of general formula:

(N-ter) FR1-CDR1-FR2-CDR2-FR3-CDR3-FR4 (C-ter);

wherein:

FR1, FR2 and FR3 are Framework Regions 1, 2 and 3;

CDR1, CDR2, and CDR3 are Complementary Determining Regions 1, 2, and 3;

at least one of said CDR1, CDR2 and CDR3 comprises a polypeptide sequence derived from a hypervariable region of said one or more reference therapeutic antibodies; and the variable region(s) of said antibody-like protein and reference therapeutic antibodies is a heavy chain (i.e. a $V_H$) or a light chain (i.e. a $V_L$) variable region.

In particular, the at least one of said CDR1, CDR2 and CDR3 may comprise at least one polypeptide sequence derived from the respective CDR1, CDR2 and CDR3 of said one or more reference therapeutic antibodies (i.e. the therapeutic antibodies disclosed herein, and combinations thereof).

Thus, according to some embodiments, the antibody-like protein comprises at least one variable region of general formula:

(N-ter) FR1-HCDR1-FR2-HCDR2-FR3-HCDR3-FR4 (C-ter); and/or (N-ter) FR1-LCDR1-FR2-LCDR2-FR3-LCDR3-FR4 (C-ter);

wherein:

FR1, FR2 and FR3 are Framework Regions 1, 2 and 3;

HCDR1, HCDR2, HCDR3 are heavy chain Complementary Determining Regions 1, 2, and 3; and LCDR1, LCDR2, LCDR3 are light chain Complementary Determining Regions 1, 2, and 3; and at least one of said HCDR1, HCDR2, HCDR3, LCRD1, LCDR2 and LCDR3 comprises at least one polypeptide sequence derived from hypervariable region(s) of said one or more reference therapeutic antibodies.

As previously stated, the chimeric non-therapeutic antibody-like protein of the invention comprising, in a hypervariable region thereof, an enzyme-cleavable peptide sequence of a hypervariable region derived from the said reference therapeutic antibody.

According to some embodiments, as previously defined, the chimeric antibody-like protein may comprise polypeptide sequences of said one or more reference therapeutic antibodies separated within a same variable region by at least one protease (i.e. trypsin) cleavage site.

Trypsin is a serine protease that specifically cleaves at the carboxylic side of lysine and arginine residues. The stringent specificity of trypsin is essential for protein identification. Trypsin is the most commonly used protease for LC-MS analyses as it generates middle-size peptides (about 8 to 30 amino acids), all carrying at least a Lysine (K) or Arginine (R) residue which confers to the peptide good ionization properties.

Thus, according to some embodiments, the chimeric antibody-like protein comprises at least one (which includes one or more than one) variable region of general formula:

(N-ter)-[PROTEASE]$_a$-Peptide 1-[PROTEASE]$_b$-Peptide 2-[PROTEASE]$_c$-Peptide 3-[PROTEASE]$_d$—(C-ter);

wherein:

[PROTEASE] is a protease (i.e. trypsin) cleavage site;

a, b, c and d are integers having a value of 0 or 1;

at least one of Peptide 1, Peptide 2 and Peptide 3 comprises at least one polypeptide sequence derived from hypervariable region(s) of said one or more reference therapeutic antibodies;

the variable region(s) of said antibody-like protein and reference therapeutic antibodies is a heavy chain (i.e. a $V_H$) or a light chain (i.e. a $V_L$) variable region.

According to said embodiments, the protease cleavage sites are preferably chosen in order to generate, upon contact with said protease, a proteolysis cleavage site comprising the said at least one polypeptide sequence derived from hypervariable region(s) of said one or more reference therapeutic antibodies.

In the context of the invention, the starting and ending residues belonging to each CDR for each antibody can be determined according either to the Kabat nomenclature or the IMGT numbering system, both of which are known in the Art.

For reference, the Kabat nomenclature is set forth in Kabat et al., 1987, in Sequences of Proteins of Immunological Interest, US Department of Health and Human Services, NIH, USA (hereafter "Kabat et al."). The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system. (http://www.bioinf.org.uk/abs/#cdrdef).

Also, for reference, the IMGT unique numbering has been defined to compare the variable domains whatever the antigen receptor, the chain type, or the species (Lefranc M.-P., "Unique database numbering system for immunogenetic analysis" Immunology Today, 18, 509 (1997); Lefranc M.-P., "The IMGT unique numbering for Immunoglobulins, T cell receptors and Ig-like domains" The Immunologist, 7, 132-136 (1999); Lefranc, M.-P., Pommié, C., Ruiz, M., Giudicelli, V., Foulquier, E., Truong, L., Thouvenin-Contet, V. and Lefranc, G., "IMGT unique numbering for immunoglobulin and T cell receptor variable domains and Ig superfamily V-like domains", Dev. Comp. Immunol., 27, 55-77 (2003).). In the IMGT unique numbering, the conserved amino acids always have the same position, for instance cysteine 23, tryptophan 41, hydrophobic amino acid 89, cysteine 104, phenylalanine or tryptophan 118. The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. If the CDR3-IMGT length is less than 13 amino acids, gaps are created from the top of the loop, in the following order 111, 112, 110, 113, 109, 114, etc. If the CDR3-IMGT length is more than 13 amino acids, additional positions are created between positions 111 and 112 at the top of the CDR3-IMGT loop in the following order: 112.1; 111.1; 112.2; 111.2; 112.3; 111.3 . . . . See also: http://www.imgt.org/IMGTScientificChart/Nomenclature/IMGT-FRCDRdefinition.html.

According to some embodiments, the chimeric antibody-like protein comprises at least one antibody-like sequence selected from a group consisting of: SEQ ID No1 to 12, and SEQ ID No113 to 119.

CDR1, CDR2 and CDR3 sequences may be selected from a group consisting of: SEQ ID No77 to 112.

Accordingly, the chimeric antibody-like protein may comprise:

a) a heavy chain in which a hypervariable region comprises at least one sequence selected from the group consisting of:
SEQ ID No77-79, 83-85, 89-91, 95-97, 101-103, 107-109; and/or
b) a light chain in which a hypervariable region comprises:
SEQ ID No80-82, 86-88, 92-94, 98-100, 104-106, 110-112.

According to some embodiments, the chimeric antibody-like protein comprises:

a) a heavy chain in which a variable region comprises at least one sequence selected from the group consisting of:
SEQ ID No13, 15, 17, 19, 21, 23, 25, 27, 29, 31, 33; and/or
b) a light chain in which a variable region comprises:
SEQ ID No14, 16, 18, 20, 22, 24, 26, 28, 30, 32, 34.

According to some embodiments, the chimeric antibody-like protein shares at most 95% of sequence identity with one or more of the reference therapeutic antibodies: which includes at most 94%, 93%, 92%, 91%, 90%, 89%, 88%, 87%, 86%, 85%, 84%, 83%, 82%, 81%, 80%, 87%, 86%, 85%, 84%, 83%, 82%, 81%, 80%, 70%, 60%, 50% and 40% of sequence identity with one or more of the said reference therapeutic antibodies.

Proteolysis peptides derived from a therapeutic antibody to be monitored by mass spectrometry when performing the therapeutic antibody quantification method described herein may be selected according to selection methods that are known from the one skilled in the art.

According to the present antibody quantification method which is performed by starting with a human sample, and especially a human plasma sample or a human plasma sample, the proteolysis peptides shall be selected so as (i) to be discriminant as regards proteolysis peptides susceptible to be generated by subjecting human endogenous proteins to the action of a protease, e;g. trypsin or IdeS, and (ii) to be discriminant as regards proteolysis peptides susceptible to be generated by the action of a protease, e.g. trypsin or IdeS, on other exogenous therapeutic antibodies that are susceptible to be present in the said human sample, e.g. the said human plasma sample or the said human serum sample.

Thus, in order to generate proteolysis peptides having the required properties, the polypeptide fragments of said one or more reference therapeutic antibodies are preferably separated within a same variable domain by at least one protease cleavage site, in particular a trypsin cleavage site.

The polypeptide sequence derived from hypervariable(s) region(s) of said one or more reference therapeutic antibodies can be of a varying length but is generally chosen to be of minimal and maximal lengths compatible with detection and identification of the corresponding proteolysis peptide by mass spectrometry. Those parameters will mostly depend on the nature of the therapeutic antibodies to be quantified (i.e. therapeutic antibodies disclosed in the present specification, and combinations thereof) and the type of mass spectrometry, but they can be readily identified by the man skilled in the Art; also, in silico methods for determining polypeptide sequences derived from hypervariable(s) region(s) of therapeutic antibodies are further disclosed in the part of the description related to methods for the quantification of antibodies.

According to a preferred embodiment, the said enzyme-cleavable peptide sequence consists of a sequence of at least 5 amino acids; which includes 5, 6, 7, 8, 9, 10, 11, 12, 13, 14, 15, 16, 17, 18, 19, 20, 21, 22, 23, 24, 25, 26, 27, 28, 29 and 30 amino acids.

According to another preferred embodiment, the said enzyme-cleavable peptide sequence consists of a sequence of at most 30 amino acids; which includes 30, 29, 28, 27, 26, 25, 24, 23, 22, 21, 20, 19, 18, 17, 16, 15, 14, 13, 12, 11, 10, 9, 8 and 7 amino acids.

According to another preferred embodiment, the said enzyme-cleavable peptide sequence consists of a sequence of at least 7 amino acids and at most 25 amino acids; which includes 7, 8, 9, 10, 11, 12, 13, 14, 15, 16, 17, 18, 19, 20, 21, 22, 23, 24, 25, 26, 27, 28, 29 and 30 amino acids.

According to another preferred embodiment, the said enzyme-cleavable peptide sequence consists of a sequence of at least 8 amino acids and at most 25 amino acids.

The invention also relates to kits and compositions comprising the above-defined antibody-like proteins.

Thus, the invention also relates to a kit for quantifying therapeutic antibodies, such a kit being described in detail elsewhere in the present specification.

Such kits are particularly useful for setting up the calibration curve required prior to sample quantification experiments.

In particular, the invention relates to a kit for quantifying therapeutic antibodies, as described in the present specification, and comprising two or more labeled forms of therapeutic antibodies.

The chimeric antibody-like protein contained in said kit may be in a lyophilized form. The kit may also contain the therapeutic antibody which will be certified for quality, purity and concentration.

Uses & Methods for the Preparation of Antibody-Like Proteins

Uses & Methods for the preparation, engineering and labeling of antibodies are fully applicable to chimeric non-therapeutic antibody-like proteins of the invention.

A chimeric antibody-like protein of the invention can be prepared as a homodimer or as a heterodimer. Heterodimers are advantageous because they may comprise an increased number of distinct signatures; and are thus particular relevant in quantification methods which require to detect a plurality of distinct therapeutic antibodies Methods are known in the Art for producing recombinant bispecific or even multispecific antibodies, which can thus be readily applied to the production of d heterodimeric antibody-like proteins according to the invention.

For antibodies such as conventional (i.e. IgG-type) antibodies, and antibody-like proteins structurally similar to said antibodies, the production of an asymmetric heterodimer can be achieved following the known methods for assembling bispecific molecules.

Yet, the asymmetrical structure of heterodimers (i.e. bispecific or multispecific antibodies) generally requires to produce the said antibody-like protein in a multiple-step process. Bispecific IgG molecules can be assembled from two different heavy and light chains expressed in the same producer cell (i.e. eukaryotic or prokaryotic). However, random assembly of the different chains (heavy and/or light chains) results in a substantial number of nonfunctional molecules in respect to bispecificity, or unwanted constructs in respect to the targeted antibody-like protein.

In a non-limitative manner, the problem of unwanted assembly can be avoided by the use of knobs-into-holes technology, as disclosed in Ridgway et al. ('Knobs-into-holes' engineering of antibody CH3 domains for heavy chain heterodimerization); Protein Eng., 9 (1996), pp. 617-621), in EP 0812357A1 and EP 0979281A1; which consists in solving the problem of heavy-chain mispairing, by introducing either «Knob» or «Hole» mutations into the CH3 domains of each (heavy) chain for directing and stabilizing the assembly.

In another method, described in WO 2011131746, heterodimeric antibody-like proteins of the present invention are prepared by a method comprising the following steps: a) providing a first therapeutic antibody or polypeptide sequence derived from hypervariable(s) region(s) of one or more therapeutic antibodies and comprising an Fc region of an immunoglobulin, said Fc region comprising a first CH3 region; b) providing a second antibody or polypeptide sequence derived from hypervariable(s) region(s) of one or more therapeutic antibodies and comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody or polypeptide sequence derived from hypervariable(s) region(s) of one or more therapeutic antibodies together with said second antibody or polypeptide sequence derived from hypervariable(s) region(s) of one or more therapeutic antibodies under reducing conditions; and d) obtaining said heterodimeric antibody-like protein. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting.

Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety.

Another technology for solving the problem of light chain mispairing is known as the CrossMab technology and is disclosed in WO 2013026833. In particular, this method is efficient for obtaining heterodimeric antibody-like proteins with two different Fabs; a structure that is generally seen for therapeutic «non-naturally occuring» bispecific antibodies. This method requires either (i) to exchange the CL and CH1 regions («cross-over» strategy) or (ii) to connect a Fab light chain and a Fab heavy chain by a peptide linker («linking» strategy). Advantageously, this method allows to generate an antibody-like protein having additional polypeptide sequences derived from reference therapeutic antibodies on both light chains.

Suitable linkers are described herein in connection with specific polypeptides of the invention and may—for example and without limitation-comprise an amino acid sequence, which amino acid sequence preferably has a length of 9 or more amino acids, more preferably at least 17 amino acids, such as about 20 to 40 amino acids. However, the upper limit is not critical but is chosen for reasons of convenience regarding e.g. biopharmaceutical production of such polypeptides. The linker sequence may be a naturally occurring sequence or a non-naturally occurring sequence.

Thus, the invention also relates to a use of at least one polypeptide derived from hypervariable(s) region(s) of one or more therapeutic antibodies, for the preparation of a chimeric non-therapeutic antibody-like protein as defined herein.

The polypeptide derived from hypervariable(s) region(s) preferably comprises an Fc region of an immunoglobulin.

A chimeric non-therapeutic antibody-like protein of the invention can be conjugated with a detectable label to form a labeled antibody-like protein. Suitable detectable labels include, for example, a stable-isotope (such as $^{15}N$), a stable-isotope molecule (for example a stable-isotope amino acid, such as arginine $^{13}C$), a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below. The detectable label can be a stable isotope. Typically the isotope-labeled polypeptide may be labeled with isotopes of hydrogen, nitrogen, oxygen, carbon, or sulfur. Suitable isotopes include, but are not limited to: $^{2}H$, $^{3}H$, $^{13}C$, $^{14}C$ $^{15}N$, $^{17}O$, $^{18}O$, or $^{34}S$. For example the labeled polypeptide may be uniformly labeled with $^{13}C$ and/or $^{15}N$. In one embodiment, all amino acids of a certain type may be labeled. For example [$^{13}C$ and/or $^{15}N$]-lysine and/or [$^{15}N$ and/or $^{13}C$]-arginine residues may be used as labeling precursors when trypsin is used as the proteolytic enzyme in a quantification method according to the invention. In a non-limitative manner, metabolic isotope incorporation may be realized by in vivo expression such as in *Escherichia coli*, in mammalian cells or by using cell-free extracts.

In particular, all the chimeric antibody-like proteins defined herein may be labeled with stable isotopes (also called herein «stable isotope labeled antibody-like proteins») according to the methods known in the Art.

The invention also relates to an isolated nucleic acid coding for a polypeptide comprising a sequence selected from the group consisting of: SEQ ID No1 to 12 and SEQ ID No113 to 119.

The coding nucleic acid may be in the form of an expression vector for a host cell, such as eukaryotic or prokaryotic cells.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibody-like proteins of the present invention. Host cells include cultured cells, e.g. mammalian cultured cells, such as CHO cells, HEK cells, BHK cells, NS0 cells, SP2/0 cells, YO myeloma cells, P3X63 mouse myeloma cells, PER cells, PER.C6 cells or hybridoma cells, bacterial cells, yeast cells, insect cells, and plant cells, to name only a few, but also cells comprised within a transgenic animal, transgenic plant or cultured plant or animal tissue.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode the chimeric antibody-like molecule of the invention or fragments thereof.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

Methods for Quantifying Therapeutic Antibodies

This invention pertains to a therapeutic antibody quantification method, which method makes use of a LC-MS/MS quantification technique.

Generally, for performing the therapeutic antibody quantification method described herein, an antibody-like protein is added to a test sample, before subjecting the resulting sample (also termed a "pre proteolysis sample" to enzyme proteolysis, so as to provide a "proteolysis sample" comprising (i) proteolysis peptides derived from the antibody-like protein and (ii) proteolysis peptides derived from the therapeutic antibody contained in the test sample. At a further step of the method, the amount of the therapeutic antibodies that were initially contained in the test sample is determined by a mass spectrometry method, which includes the calculation of a ratio between (i) one or more selected proteolysis peptides derived from the reference therapeutic antibodies and (ii) one or more corresponding proteolysis peptides derived from the said therapeutic antibodies susceptible to be initially contained in the test sample.

Indeed, for performing the therapeutic antibody quantification method described herein, it is essential that (i) a given proteolysis peptide derived from an antibody-like protein and (ii) the corresponding proteolysis peptide derived from the one or more therapeutic antibodies initially contained in the test sample be distinguished by the respective spectrometry signals that are generated by these peptides, so as to enable the calculation of a ratio between (i) the said proteolysis peptide derived from the said antibody-like protein and (ii) the said corresponding proteolysis peptide derived from the said one or more therapeutic antibodies initially contained in the test sample.

In preferred embodiments of the therapeutic antibody quantification method described herein, these proteolysis peptides may be distinguished by mass spectrometry by using an antibody-like peptide as defined herein consisting of a labeled antibody-like protein, and most preferably a Stable Isotopically Labeled (SIL) antibody-like protein.

As it is readily understood from the present specification, the quantification method described herein is useful both (i) in situations wherein a tested patient has received a therapeutic treatment by administration of a unique therapeutic antibody and (ii) in situations wherein a tested patient has received, simultaneously or sequentially, more than one therapeutic antibody.

As illustrated in the examples herein, the inventors have shown that a precise quantification of therapeutic antibodies in a sample (i.e. a human sample) may be performed through the design of a method wherein the amount of therapeutic antibodies, if present in the said sample, is determined by a mass spectrometry method making use of (i) proteolysis peptide(s) derived from two or more therapeutic antibodies contained in the said human sample and (ii) proteolysis peptide(s) derived from the antibody-like protein after:

(A) calculating a ratio between:
  (i) the spectrometry signal generated by one or more selected therapeutic antibody-derived proteolysis peptide from each of two or more therapeutic antibodies
  and
  (ii) the spectrometry signal generated by one or more proteolysis peptides from each of the labeled forms of antibody-like proteins, and
(B) determining the amount of therapeutic antibodies, if present, in the said human sample by reporting the ratio value calculated at step (A) for each of the one or more proteolysis peptide to a calibration curve of ratio values.

Selecting Proteolysis Peptides Derived from a Therapeutic Antibody

Proteolysis peptides derived from a therapeutic antibody to be monitored by mass spectrometry when performing the therapeutic antibody quantification method described herein may be selected according to selection methods that are known from the one skilled in the art.

When the present antibody quantification method is performed by starting with a human sample, and especially a human plasma sample or a human serum sample, the proteolysis peptides shall be selected so as (i) to be discriminant as regards proteolysis peptides susceptible to be generated by subjecting human endogenous proteins to the action of a protease, e;g. trypsin or IdeS, and (ii) to be discriminant as regards proteolysis peptides susceptible to be generated by the action of a protease, e.g. trypsin or IdeS, on other exogenous therapeutic antibodies that are susceptible to be present in the said human sample, e.g. the said human plasma sample or the said human serum sample.

Usually, 'signature' peptides, which are peptides unique for the specific target protein, are chosen as the surrogate peptides. Selection of the appropriate surrogate peptides should: retain peptides with appropriate length (~8-20 amino acids): being too short may cause the lack of selectivity, and too long may affect the sensitivity (Wu et al., Rapid Commun Mass Spectrom. 2011; Vol. 25:281-90).

A typical procedure is to perform an in silico digestion of the given therapeutic antibody to generate a set of potential surrogate peptides. These peptides are then searched against all existing proteins in the biological matrices using online databases (e.g., Standard Protein BLAST, http://www.ncbi.nlm.nih.gov/BLAST/Blast.cgi?PAGE=Proteins) to confirm that the signature peptides only exist in the target protein. The sensitivity, specificity and chromatographic behavior of these signature peptides are then evaluated using actual digested protein samples in biological matrices, and the best one(s) will be chosen as the surrogate peptide(s) for the said given therapeutic antibody.

The proteolysis peptides are selected based on online in silico prediction tools (Kamiie et al., Pharmaceutical Research, vol. 25(6): 1469-1483, 2008). All potential tryptic peptides were screened by alignment against the human proteome.

As used herein, proteolysis peptides, which may also be termed surrogate peptides herein, are selected on the basis on their uniqueness among the peptides that may be present after subjecting human plasma or human serum to a protease. Accordingly, each selected proteolysis peptide consists of a unique signature of the presence of a given therapeutic antibody in a sample.

For a given therapeutic antibody to be quantified with the quantification method described herein, the selection of one or more proteolysis peptide(s) (i.e. "surrogate peptide(s)") may be performed by comparing (i) a set of the expected proteolysis peptides derived from the said given therapeutic antibody with (ii) a set of the proteolysis peptides that are expected to be derived from the same proteolysis of human plasma or human serum proteins, and especially a set of the proteolysis peptides that are expected to be derived from the same proteolysis of therapeutic antibodies.

In some embodiments, the set of expected proteolysis peptides may be obtained in silico by using the query peptide mass on the online bioinformatics tool www.expasy.ch after entering on the tool (i) the sequence of the said given therapeutic antibody and (ii) the sequences of the proteins that are expected to be contained in human plasma or human serum, and especially the sequences of therapeutic antibodies, such as human IgG. Then, peptides found exclusively in the set of proteolysis peptides derived from the said given therapeutic antibody and which are thus not found in the set of proteolysis peptides derived from the proteins that are expected to be contained in the sample are selected.

The selection of proteolysis peptides (surrogate peptides) derived from the said given therapeutic antibody may also be performed in silico, by performing a similarity research by sequence alignment against a human protein database such as the UniProtKB_HUMAN database, and by using a relevant bioinformatics software, e.g. the bioinformatics tool termed BLAST 2.0 (Basic Local Alignment Search Tool). Selection of the one or more proteolysis peptide(s) derived from the said given therapeutic antibody for LC-MS/MS quantification shall generally take into account of the score resulting from the BLAST which calculates the statistical significance of matches.

Among set of one or more potential proteolytic peptides pre-selected as described above, those potential proteolytic peptides with missed cleavage sites by the protease are excluded. Missed cleavage sites may be predicted by using the software called MC:pred (Lawless et al., OMICS, September 2012, Vol. 16(9).

Methods for quantifying one or more therapeutic antibodies in a sample of an individual can be, for instance, as described in FIGS. 2B, 2C and 2D.

In one approach, the antibody to quantify is a therapeutic antibody and the internal antibody standard used as quantification standard is a labelled antibody containing at least one proteotypic peptide of the therapeutic antibody («Antibody-like approach» set in FIG. 2B).

In one approach, a plurality (at least two) of therapeutic antibodies is quantified simultaneously. The internal antibody standard (IS) used as quantification standard is a labelled multiplex antibody-like protein containing at least one proteotypic peptide of each therapeutic antibody. This strategy can be adapted to quantify more than 2 different therapeutic antibodies («Multiplex antibody-like approach» set in FIG. 2C).

In one variant approach, a plurality (at least two) of therapeutic antibodies is quantified, by using a bispecific antibody. Accordingly, the antibody-like protein contains at least one proteotypic peptide of each therapeutic antibody («Bispecific antibody-like approach» set in FIG. 2D).

Thus, the invention also relates to a method for quantifying one or more therapeutic antibodies in a sample of an individual comprising the steps of:

a) adding to a test sample which contains therapeutic antibodies a known amount of one or more labeled forms of a non-therapeutic antibody-like protein according to the invention, or a composition thereof, whereby a pre-proteolysis sample is provided, b) subjecting the pre-proteolysis sample to an enzyme proteolysis, so as to provide a proteolysis sample comprising (i) proteolysis labeled peptides derived from the labeled antibody-like proteins and (ii) proteolysis peptides derived from the therapeutic antibody contained in the test sample, c) determining by mass spectrometric analysis the ratio between (i) one or more selected proteolysis labeled peptides and (ii) one or more corresponding proteolysis peptides derived from the said therapeutic antibody, d) calculating from the ratio determined at step c) the amount of the said therapeutic antibody in the test sample.

Advantageously, the non-therapeutic antibody-like protein according to the invention renders the above-mentioned therapeutic antibody quantification method compatible with Uniplex and Multiplex analysis, even on human samples (i.e. human serum and human plasma), for clinical purposes.

In some embodiments, the therapeutic antibody quantification method described herein may be performed for two or more (a plurality of) antibodies.

Thus, the quantification method that is described herein allows the quantification of two or more therapeutic antibodies, irrespective of the identity of the said therapeutic antibodies. The therapeutic antibodies to be quantified by the method described herein may be any antibodies of therapeutic interest, e.g. any therapeutic antibody that is the subject of a marketing authorization, at the time of performing the said therapeutic antibody quantification method.

Accordingly, the invention also relates to a method for quantifying a plurality of therapeutic antibodies in a sample of an individual comprising the steps of:

a) adding to a test sample which contains therapeutic antibodies a known amount of one or more labeled forms of a non-therapeutic antibody-like protein according to the invention, or a composition thereof, whereby a pre-proteolysis sample is provided, b) subjecting the pre-proteolysis sample to an enzyme proteolysis, so as to provide a proteolysis sample comprising (i) proteolysis labeled peptides derived from the labeled antibody-like proteins and (ii) proteolysis peptides derived from the therapeutic antibody contained in the test sample, c) determining by mass spectrometric analysis the ratio between (i) one or more selected proteolysis labeled peptides and (ii) one or more corresponding proteolysis peptides derived from the said therapeutic antibody, d) calculating from the ratio determined at step c) the amount of the said therapeutic antibody in the test sample.

Generating a Calibration Curve

The precise quantification of therapeutic antibodies by mass spectrometric analysis is allowed by the use of at least one non-therapeutic antibody-like protein of the invention structurally similar to the therapeutic antibody/antibodies of interest, the presence of which in combination with the said antibody/antibodies of interest in a sample (i.e. a human sample) permits the calculation of ratio values between (i) the spectrometry signal generated by a selected proteolysis surrogate peptide derived from a specific therapeutic antibody and (ii) the spectrometry signal generated by a corresponding selected labeled surrogate peptide generated by enzyme proteolysis treatment of a labeled form the antibody-like protein.

As it will be further detailed in the present specification, the quantification of therapeutic antibodies is performed by reporting the ratio value calculated for each proteolysis peptide considered in the sample tested, or test sample, to a calibration curve of ratio values generated, for each therapeutic antibody of interest, with known amounts of the said therapeutic antibody of interest and fixed and known amounts of a labeled antibody-like protein that is used as an Internal Standard compound.

For generating a calibration curve, a serial or set of calibration samples (CS) are prepared, wherein:

each calibration sample contains a known amount of the selected therapeutic antibody, each calibration sample contains a fixed and known amount of a labeled form of the antibody-like protein used as an Internal Standard compound, and the serial or set of calibration samples are prepared so as to cover an amount range of the therapeutic antibodies encompassing at least the amount range of the therapeutic antibody(ies) which is(are) expected to be contained in a test sample.

For the sake of clarity, each calibration sample comprises the same fixed and known amount of the selected Internal Standard compound.

Illustratively, the amount range of the selected therapeutic antibody which is covered by the serial or set of calibration samples, when expressed as a final concentration in the calibration samples, may range from 0.1 µg/mL to 100 µg/mL. For example, a serial or set of calibration samples may comprise eight calibration samples comprising a therapeutic antibody of interest at respective final concentrations of 0.1 µg/mL, 0.5 µg/mL, 1 µg/mL, 5 µg/mL, 10 µg/mL, 20 µg/mL, 25 µg/mL, 50 µg/mL, 75 µg/mL and 100 µg/mL.

Thus, according to the therapeutic antibody quantification method described herein, a calibration curve may be generated for each of the therapeutic antibody of interest. In other embodiments, a calibration curve may be generated simultaneously for a plurality of therapeutic antibodies Indeed, the amount of therapeutic antibodies that may be found in a test sample, especially in a test sample consisting of a human serum sample originating from a patient treated by therapeutic antibodies, may vary, depending of (i) the amount of therapeutic antibody(ies) which has(have) been administered to the said patient, (ii) the time period when the serum sample has been collected since the starting time period of the treatment, (ii) the time period of collection of the serum sample since the last administration of therapeutic antibodies, and (iv) physiological parameters which may be specific to the said patient, such as the rate of clearance of the said antibodies from the blood.

In some embodiments, the serial or set of calibration samples may further comprise one or more control calibration samples which do not contain the selected therapeutic antibody, or alternatively which do not contain any therapeutic antibody.

Most preferably, a calibration sample is prepared starting from a body fluid sample initially exempt of the selected therapeutic antibody or of the selected Internal Standard compound, and preferably serum or plasma from a non-human mammal or from a human individual, and most preferably human serum or human plasma.

Then, each of the calibration sample is subjected to the same method steps as that which is described for the test samples elsewhere in the present specification, so as to provide a serial or a set of calibration assay samples (CAS).

Then, each calibration assay sample is subjected to spectrometric analysis, and most preferably to a LC-MS/MS analysis, in the same conditions as those described for the test samples elsewhere in the present specification and the values of the spectrometry signals generated by (i) a selected surrogate peptide generated by enzyme proteolysis of the selected therapeutic antibody and (ii) by the corresponding selected labeled peptide (also termed "labeled surrogate peptide") generated by enzyme proteolysis of the selected antibody-like protein.

Then, for each of the calibration assay sample (CAS), a ratio of (i) the spectrometry signal value generated by the selected therapeutic antibody surrogate peptide to (ii) the spectrometry signal value generated by the selected antibody-like protein-derived labeled surrogate peptide is calculated.

As it will be further detailed in the present specification, a spectrometric signal value may consist of the peak area of specific SRM (Selected Reaction Monitoring), or more precisely of the mean of the peak areas of specific SRM, generated by a selected peptide of interest, typically by a selected surrogate tryptic peptide derived from the selected labeled therapeutic antibody used as an Internal Standard described herein.

Thus, it is provided a serial or a set of ratio values, each ratio value being calculated from a calibration assay sample obtained from a starting calibration sample comprising known amounts, e;g. known final concentrations, of the selected therapeutic antibody and a fixed and known amount of the Internal Standard compound.

A calibration curve may then be generated by plotting the serial or set of calculated ratio values versus the corresponding theoretical amounts of the selected therapeutic antibody, e;g. versus the corresponding known final concentrations of the selected therapeutic antibody.

As used herein, a "final" concentration of a selected therapeutic antibody is the concentration of the said therapeutic antibody in an initial Calibration Sample (CS), which CS comprises a known added amount of the said therapeutic antibody.

The individual to be tested may be human or non-human. The sample (i.e. liquid, tissue or biopsy) may be any sample susceptible to contain therapeutic antibodies, such as blood or a blood-derived sample.

Thus, in some embodiments, the sample which is used in the quantification method originates from a whole human blood sample that has been previously collected from an individual. In preferred embodiments, the blood cells, and especially erythrocytes, are removed by centrifugation so as to obtain a plasma sample. In other preferred embodiments, coagulation of the whole blood sample is allowed to occur and a serum sample is obtained.

In further embodiments, the sample which is used in the quantification method may consist of other extracellular fluids such as lymphatic fluid (endolymph or perilymph) and interstitial fluid.

Most preferably, at least for determining the pharmacokinetic profile of therapeutic antibodies in an individual, the said sample is a blood plasma sample or a blood serum sample, or a sample derived from blood plasma or blood serum.

In some embodiments, the initial sample may be subjected to dilution, e.g. in an aqueous medium such as in a saline solution or in a buffer solution, before being used as the assay sample in the therapeutic antibody quantification method according to the invention.

However, in the most preferred embodiments, the initial sample, such as a plasma sample or a serum sample, is used without any pre-treatment and in particular is used as such undiluted.

As it will be described further in the present specification, according to the therapeutic antibody quantification method described herein, the sample to be tested is added with a known amount of antibody-like protein in the sense of the invention.

Enriching the Sample in Therapeutic Antibodies

According to some other aspects of these embodiments of step a), or alternatively step a2), of the therapeutic antibody quantification method, immunocapture may be performed by using a substrate onto which Fc-binding molecules (e.g. protein A molecules or protein G molecules) are immobilized.

Enriching in Therapeutic Antibodies by Depletion in Non-Antibody Protein

In some embodiments, of the therapeutic antibody quantification method described herein, step a), or alternatively step a2), may consist of a step wherein the enrichment in therapeutic antibodies is performed by depletion of a substantial part of the proteins, except the antibody proteins, that are initially contained in the test sample.

However, general enrichment in therapeutic antibodies (such as IgG antibodies) by using a method of precipitation of plasma proteins possesses several drawbacks. Such a method for general precipitation of plasma proteins, although it is simple, fast, inexpensive and allows access to the measurement of total protein fraction, the resulting plasma proteins-enriched mixture is not sufficiently enriched in therapeutic antibodies, which is detrimental to the repeatability of the subsequent step of trypsin proteolysis, and finally be detrimental to the accuracy of the therapeutic (i.e. anti-TNF and/or anti-cancer) antibody quantification method. Consequently, although such a precipitation method may be used for performing the therapeutic antibodies quantification method described herein, such an embodiment of sample preparation is not the most preferred.

According to some aspects of these embodiments, depletion in non-antibody proteins may be performed by using specific resins having affinity for proteins that are known in the art, such as the Cibacron-blue resin, which includes the Cibacron-Blue™ 3 GA agarose commercialized notably by the Company Sigma-Aldrich (MI, USA).

According to some other aspects of these embodiments, depletion in non-antibody proteins may be performed by precipitation of a substantial part of the proteins initially contained in the test sample, except the antibody proteins.

In some embodiments of the quantification method described herein, the sample, optionally comprising the antibody-like protein, is enriched in therapeutic antibodies, such as IgG antibodies.

Various methods for enriching a sample in therapeutic antibodies are known in the art.

In some embodiments, enrichment in therapeutic antibodies may be performed by ammonium sulfate precipitation, by using methods well known in the art, so as to obtain an antibody-enriched composition, such as an IgG-enriched composition.

According to further aspects of these embodiments, depletion in non-antibody proteins may be performed by precipitation of the antibody proteins initially contained in the test sample, such as by performing antibody precipitation with ammonium sulfate, e.g. by using a saturated ammonium sulfate solution (30% v/v).

Protein A/G or Protein L Chromatography

In some embodiments of the quantification method described herein, the sample, optionally comprising the antibody-like protein, is enriched in therapeutic antibodies, in particular IgG antibodies.

In some embodiments, enrichment in therapeutic antibodies may be performed by affinity chromatography, which includes the use of chromatography substrates onto which have been immobilized relevant ligands such as protein A, protein G, protein L or alternatively antibodies binding to the Fc portion of therapeutic antibodies, as well as nucleic acid or peptide aptamers that bind to the Fc portion of therapeutic antibodies.

The step of enrichment in therapeutic antibodies allows separating antibodies from other abundant plasma proteins and thus contributes to improve sensitivity and reproducibility of the antibody quantification method.

Preferably herein, enrichment in therapeutic antibodies by using protein A or protein G chromatography is preferred.

In particular, IgG enrichment by subjecting the sample to protein A or protein G chromatography allows depletion of almost the whole plasma proteins while retaining the whole IgG antibodies initially contained therein, which includes the whole therapeutic antibodies initially contained therein.

Most preferably, enrichment in IgG antibodies is performed by protein A chromatography.

In the embodiments wherein protein A/G chromatography is used, elution of the retained therapeutic antibodies, in particular IgG antibodies, is conventionally performed at an acidic pH, generally at a pH in the range of 2-3, preferably at a pH of 2.8. Then, the fraction containing the most part of the therapeutic antibodies may be collected by elution using a formic acid solution (0.5%-1% v/v) at a pH ranging from 1 to 3. After evaporation of the formic acid, the dry sample may be resuspended in a liquid medium containing ammonium bicarbonate at a pH ranging from 7 to 8, for further processing.

In these embodiments, there is thus provided an antibody-enriched composition, in particular an IgG-enriched composition, containing a known amount of the antibody-like protein and an unknown amount of therapeutic antibodies.
Concentrating the Antibody-Enriched (i.e. IgG Enriched) Composition In some embodiments, and especially in embodiments wherein the antibody-enriched composition is obtained by a step of chromatography wherein sample dilution is susceptible to occur, the said composition is then subjected to a concentration step, so as to provide a concentrated antibody-enriched composition.

In these embodiments, the concentration step may be performed by any method known in the art, including dialysis and filtration, e.g. microfiltration or ultrafiltration.

In preferred embodiments, the concentration step is an ultrafiltration step wherein a filter membrane of a relevant cut-off value is used.

Illustratively, the ultrafiltration step may be performed by using an ultrafiltration membrane having a cut-off value of about 100 kDa.

In the embodiments wherein the concentration step is an ultrafiltration step, a buffer exchange is performed during the ultrafiltration step so as to optimize the conditions of the further steps of the method are conducted. Notably, the buffer exchange that may be performed during the ultrafiltration step allows obtaining a concentrated IgG-enriched composition in which the subsequent step of proteolysis by trypsin will be optimally realized.
Proteolysis Step This step is step b) of the general therapeutic antibody quantification method described herein.

As it is described further herein, the proteolysis step consists of subjecting the pre-proteolysis mixture, containing the labeled antibody-like protein and possibly the non-labeled therapeutic antibodies to be quantified, to an enzyme proteolysis so as to generate, notably, therapeutic antibody-derived proteolysis peptides, namely (i) labeled therapeutic antibody-derived proteolysis peptides generated from the antibody-like protein added at step a) and non-labeled therapeutic antibody-derived proteolysis peptides generated from the non-labeled therapeutic antibodies to be quantified, if these non-labeled therapeutic antibodies are present initially in the test sample.

A plurality of embodiments of a proteolysis step may be performed. In particular, the proteolysis enzymes, which may also be termed proteases herein, may be selected in a vast group of proteases well known in the art. Since the cleavage site(s) of each known protease is part of the technical knowledge of the one skilled in the art, the selection of a specific protease at step b) is correlated to the subsequent monitoring of the expected resulting therapeutic antibodies proteolysis peptides generated therefrom, by mass spectrometric analysis.

In some embodiments of the proteolysis step that are illustrated in the examples herein, the selected protease possesses trypsin activity.

In some other embodiments of the proteolysis step that are illustrated in the examples herein, the selected protease possesses a hinge-targeting activity.
One-Step Trypsin Proteolysis According to these embodiments of the proteolysis step, trypsin is added to the pre-proteolysis mixture, so as to generate (i) tryptic peptides from the therapeutic antibody initially contained in the test sample and (ii) tryptic peptides generated by trypsin proteolysis of the labeled antibody-like protein. The specific tryptic peptides derived from the antibody-like protein may also be termed "surrogate peptides" herein.

As an example, a set of tryptic peptides derived from therapeutic antibodies and comprising at least a part of a hypervariable region from said antibodies (i.e. selected from H-CDR1, H-CDR2, H-CDR3, L-CDR1, L-CDR2, L-CDR3) is provided as SEQ ID No35 to SEQ ID No76 (see sequence listed).

In some embodiments, the one-step trypsin proteolysis is performed by using trypsin as the sole added protease.

In some other embodiments that are illustrated in the examples herein, the one-step trypsin proteolysis is performed by using a combination of trypsin and endoproteinase Lys-C (also termed "EndolysC" herein) as the "protease". According to these embodiments, the combination or mixture of trypsin and endoproteinase Lys-C contains advantageously a weight amount ratio of trypsin to EndolysC ranging from 0.1:1 to 20:1, which encompasses a weight amount ratio from 0.5:1 to 15:1, preferably a weight amount ratio ranging from 1:10:1. As it is well known in the art, trypsin cleaves peptide chains mainly at the carboxyl side of the amino acids lysine and arginine, except when either is followed by proline.

As it is also well known in the art EndolysC cleaves peptide chains at the carboxyl side of lysine amino acid.

The proteolysis step is preferably performed in conditions that are optimal for:
(i) generating all the expected surrogate tryptic peptides, and
(ii) avoiding trypsin autolysis.

It may be used a purified trypsin having a low ability to autolysis.

Illustratively, it may be used a trypsin termed Trypsin Gold® which is marketed by the company Promega (Madison, Wis., United States).

Optimal proteolysis conditions may be reached by using a trypsin/total protein molar ratio ranging from 1/100 to 1/1.

In most preferred embodiments, the proteolysis step is performed in non-denaturing conditions, i.e. in conditions which do not cause protein denaturation. Notably, the proteolysis step is performed in the absence of a protein denaturation agent such as urea or guanidium hydrochloride.

Proteolysis in the presence of trypsin is performed during a period of time that may be optimally adapted by the one skilled in the art.

Advantageously, proteolysis is performed at 37° C. during a period of time ranging from 0.5 hour to 15 hours, preferably from 1 hour to 10 hours, and most preferably ranging from 2 hours to 4 hours. In some embodiments, proteolysis is performed at 37° C. overnight.

The one-step proteolysis step is performed at a pH of 6 or more. Further, the one-step proteolysis step is advantageously performed at a pH of less than 8.5, preferably at a pH of 8 or less, which includes at a pH of 7.5 or less, e.g. at a pH of about 7.

In most preferred embodiments, the one-step proteolysis step is performed under non-denaturing conditions that is under conditions wherein there is no denaturation of the proteins initially contained in the pre-proteolysis sample.

In some embodiments, proteolysis is stopped by acidification of the resulting mixture, for example by adding an appropriate acid such as formic acid, so as to decrease the pH of the said resulting mixture below pH 6.

Two-Step Trypsin Proteolysis

In some embodiments, step b) may be performed by a two-step trypsin proteolysis. In these embodiments, step b) comprises two enzyme proteolysis steps, namely step b1) of enzyme proteolysis under denaturing conditions and step b2) of enzyme proteolysis in non-denaturing conditions, as it is illustrated in the examples herein.

The enzyme(s) which is used at steps b1) and b2) may be the same as those disclosed for performing the "one-step trypsin proteolysis" specified above.

In some embodiments, the enzyme(s) which is(are) used at step b1) is(are) the same as that(those) which is(are) used ate step b2). In some other embodiments, the enzyme(s) which is(are) used at step b1) is(are) distinct from that (those) which is(are) used ate step b2).

According to the two-step proteolysis method, step b1) consists of a pre-digestion step wherein aimed at increasing the sensitivity of the proteins contained in the pre-proteolysis sample, and mainly the trypsin sensitivity of the antibodies (including the therapeutic antibodies) contained in the pre-proteolysis sample.

Step b1) is performed in denaturing conditions, such that in the presence of urea, advantageously at a final concentration ranging from 4 M to 0.1 M, preferably at a final concentration of about 4 M.

In some embodiments, step b1) is performed by using a protease mixture of EndolysC and trypsin in an amount as described of the "one-step trypsin proteolysis" embodiment above.

In some other embodiments, step b1) is performed by using EndolysC as the sole protease. According to these other embodiments, EndolysC is present in the resulting sample at a final concentration ranging from 0.01 μg/mL to 10 μg/mL.

At step b1) proteolysis is performed during a time period of 0.5 h to 6 h; advantageously from 0.75 h to 4 h, preferably from 1 h to 3 h, and may be performed during a time period of about 2 h.

At step b1) proteolysis is preferably performed at 37° C.

At step b1) proteolysis is performed at a pH of 6 or more. Further, the one-step proteolysis step is advantageously performed at a pH of less than 8.5, preferably at a pH of 8 or less, which includes at a pH of 7.5 or less, e.g. at a pH of about 7.

Further, step b2) is performed by using a protease mixture comprising trypsin.

In some embodiments, step b2) is performed by using a protease mixture of EndolysC and trypsin in an amount as described of the "one-step trypsin proteolysis" embodiment above. In some aspects of these embodiments, the protease mixture of EndolysC and trypsin is added at step b1) and there is preferably no addition of further protease or protease mixture at step b2) since the said protease or protease mixture is already present at the appropriate final concentration in the pre-digestion sample obtained at the end of step b1). According to these embodiments, step b1) may performed in conditions wherein EndolysC is active and trypsin is inactive, and wherein trypsin is rendered active at step b2) by bringing changes in the sample physico-chemical conditions such that by adding an appropriate buffer composition at the beginning of step b2). Illustratively, ammonium bicarbonate buffer solution at an appropriate final concentration may be added at the beginning of step b2).

In some other aspects of these embodiments wherein step b1) is performed by using EndolysC, an appropriate amount of trypsin is added at the beginning of step b2), so that the sample used at the beginning of step b2) comprises a protease mixture of EndolysC and trypsin, at the desired ratio and final concentration.

In some other embodiments, step b1) is performed by using trypsin as the sole added protease. According to these other embodiments, there is preferably no further addition of trypsin at step b2).

Advantageously, proteolysis at step b2) is performed at 37° C. during a period of time ranging from 0.5 hour to 15 hours, preferably from 1 hour to 10 hours, and most preferably ranging from 2 hours to 4 hours. In some embodiments, proteolysis is performed at 37° C. overnight.

The one-step proteolysis at step b2) is performed at a pH of 6 or more. Further, the one-step proteolysis step is advantageously performed at a pH of less than 8.5, preferably at a pH of 8 or less, which includes at a pH of 7.5 or less, e.g. at a pH of about 7.

Proteolysis with a Hinge-Targeting Protease

In some embodiments of step b), proteolysis is performed by using a hinge-targeting protease. Hinge-targeting proteases are known proteases effecting a cleavage in an antibody protein in the hinge region so as to generate (i) two Fc regions of the heavy chains and (ii) an F(ab')$_2$ moiety, respectively. Fab moieties may then be obtained from the F(ab')$_2$ moiety, by methods well known form the one skilled in the art, such as by using a reducing agent such as dithiothreitol (DTT).

At step b), the hinge-targeting protease is preferably selected in a group comprising Gelatinase A (MMP-2) (Tamerius et al., 1975, Int J Cancer, Vol. 16:456-464), Stromyelysin (MMP-3) (Tamerius et al., 1975, Int J Cancer, Vol. 16:456-464; Tamerius et al., 1976, J Immunol, Vol. 116:724-730; Reichert et al., 2010, Mabs, Vol. 2:84-100), Matrilysin (MMP-7) (Tamerius et al., 1975, Int J Cancer, Vol. 16:456-464; Tamerius et al., 1976, J Immunol, Vol. 116:724-730; Reichert et al., 2010, Mabs, Vol. 2:84-100), Gelatinase B (MMP-9) (Reichert et al., 2010, Mabs, Vol. 2:84-100), Macrophage metalloelastase (MMP-12) (Tamerius et al., 1976, J Immunol, Vol. 116:724-730; Reichert et al., 2010, Mabs, Vol. 2:84-100), Collagenase-3 (MMP-13) (Tamerius et al., 1976, J Immunol, Vol. 116:724-730), Cathepsin G (Reichert et al., 2010, Mabs, Vol. 2:84-100), Pseudolysin (Strohl et al., 2009, Curr Opinion Biotechnol, Vol. 20:685-691), Mirabilysin, Glutamyl endopeptidase I (GluV8) (Tamerius et al., 1976, J Immunol, Vol. 116:724-730; Reichert et al., 2010, Mabs, Vol. 2:84-100), Streptopain (SpeB) (Brerski et al., 2010, mAbs, Vol. 2:3:212-220), Trepolisin (Brerski et al., 2010, mAbs, Vol. 2:3:212-220) and Immunoglobulin-degrading enzyme from *Streptococcus* (ideS) (Tamerius et al., 1976, J Immunol, Vol. 116:724-730; Reichert et al., 2010, Mabs, Vol. 2:84-100).

Most preferably, these embodiments of step b) are performed by using Immunoglobulin-degrading enzyme from *Streptococcus* (ideS) as the hinge-targeting protease. In these embodiments, it may be used ideS which is immobilized on an appropriate solid support, e.g. an agarose support, such as in the FragIT™ kit commercialized by the Company Genovis (Luna, Sweden) or the Company Sigma-Aldrich (Saint Louis, Mo., United States).

At step b) the pre-proteolysis sample is subjected to proteolysis with an ideS protease at room temperature during a time period ranging from 5 mins to 96 hours, advantageously from 10 mins to 50 hours, which includes a time period ranging from 1 hour to 5 hours.

The resulting proteolysis mixture may be collected by centrifugation and/or protein precipitation, before-suspension, as it is illustrated in the examples herein.

Quantification of Therapeutic Antibodies by Mass Spectrometric Analysis

This step encompasses steps c) and d) of the general therapeutic antibody quantification method described herein.

Step c) is performed by mass spectrometry, according to techniques of protein quantification by mass spectrometry that are known in the art.

Preferably, step c) is performed according to the method of Liquid Chromatography coupled to tandem Mass Spectrometry (LC-MS/MS), as it is shown in the examples herein.

Preferably, it is used a triple quadrupole (QqQ) mass spectrometer equipped with an ESI source operating in positive ion mode and using multiple reaction monitoring (MRM) mode for quantification.

In some embodiments, Liquid Chromatography is performed with a reverse phase chromatography substrate.

Then, in some embodiments, the most abundant state of charge of (i) selected surrogate proteolytic peptides derived from the labeled therapeutic antibodies used as Internal Standard compounds and of (ii) the proteolytic peptides derived from the therapeutic antibodies initially present in the test sample are observed preferably between 200 m/z and 2000 m/z in ESI ionization source and are selected and fragmented.

At the quantification step by mass spectrometry, it is researched the Selected Reaction Monitoring (SRM) transitions specific of
(i) the selected surrogate proteolytic peptide(s) of a therapeutic antibody and of
(ii) the corresponding labeled proteolytic peptide derived from the corresponding labeled antibody-like protein that is used as standard.

In the embodiments wherein the proteolysis step is performed by using trypsin or a trypsin-containing protease composition wherein anti-cancer antibodies are quantified and wherein an antibody-like protein is used as standard, the number of selected proteolysis peptides for which a mass spectrometric signal ratio is determined at step c) may vary according notably to of the number of available proteolysis peptides. The number of selected proteolysis peptides for which a mass spectrometric signal ratio is determined at step c) may vary from 1 to 10 proteolysis peptides, depending from the number of proteolysis peptides which are available, which encompasses 1, 2, 3, 4, 5, 6, 7, 8, 9 and 10 selected proteolysis peptides.

SRM transitions of selected proteolytic peptides from the therapeutic antibodies tested, of proteolytic labeled peptides from the antibody-like proteins used as Internal Standard are preferably established after comparing the fragmentation spectra obtained from pure solutions of each of these peptides, with in silico fragmentation spectra generated with a relevant available software tool, such as the software commercialized under the name Skyline™ by MacCoss Lab Software (USA) and the bioinformatics tool ESP Predictor available from Genepattern (Vincent A. Fusaro, D. R. Mani, Jill P. Mesirov & Steven A. Carr, Nature Biotechnology (2009) 27:190-198), available notably from the Broad Institute (USA)

Preferably, at step d), quantification of therapeutic antibodies is based on the ratio of the mean of the peak areas of specific SRM of a selected therapeutic antibody and the mean of the peak areas of the antibody-like protein.

The present invention is further illustrated, without being limited thereto, by the examples below.

EXAMPLES

Example 1: Quantification with a Labelled Antibody-Like Protein as Standard

I-Material & Methods

Experimental

Reagents & Chemicals
PBS10xpH 7.4 were purchased from Life Technologies (Saint Aubin, France). [$^{13}C_6, ^{15}N_4$] Arginine and [$^{13}C_6, ^{15}N_2$] Lysine were purchased from (Eurisotop, Saint Aubin, France). Pierce™ Protein G Spin Plate for IgG screening was purchased from Thermofisher Scientific (Waltham, Mass., USA). Acetonitrile (LC-MS Chromasolv®), Water (LC-MS Chromasolv®), Ammonium bicarbonate, human serum, were purchased from SIGMA-Aldrich (St Louis, Mich., USA), Formic acid (Aristar®) was purchased from VWR (Radnor, Pa., USA), Sequencing grade modified trypsin was obtained from Promega (Madison, Wis., USA). Commercial Erbitux® was obtained form Myoderm Ltd (Leicestershire, UK), Avastin® was obtained from Grenoble hospital pharmacy.

Expression of Stable-Isotope Labeled Cetuximab, Bevacizumab, Cetuximab-Like and Bevacizumab-Like Standards
Isotopically labeled forms of antibodies were produced in HEK293 cells cultivated in specific medium containing [$^{13}C_6, ^{15}N_4$] Arginine and [$^{13}C_6, ^{15}N_2$] Lysine amino acids according to the method previously described (Lebert et al., Bioanalysis, 2015).

LC-MS/MS
LC-SRM analyses were performed on a 6500QTrap hybrid triple quadrupole/ion trap mass spectrometer (ABSciex, Framingham, Mass., USA) equipped with a TurboV source (AB Sciex) and controlled by Analyst software (version 1.6, AB Sciex). The instrument was linked to an Exion uHPLC system (ABSciex, Framingham, Mass., USA). Chromatography was performed using a two-solvent system combining solvent A (2% acetonitrile, 0.1% formic acid) and solvent B (80% acetonitrile, 0.1% formic acid). Peptides were separated on a Kinetex XB-C18 column, 2.1 mm×100 mm, 1.7 µm, 100 Å (Phenomenex, Le Pecq, France). Peptide separation was achieved using a multistep gradient from 4% to 100% B over 7 min at a flow rate of 120 µl/min. MS data were acquired in positive mode with an ion spray voltage of 5500 V and the interface heater temperature was set to 550° C. Collision exit, declustering and entrance potentials were set to 19, 60 and 12 V, respectively. The appropriate collision energy (CE) was calculated based on the following equations: CE (Volts)=0.44*m/z+4 for doubly-charged precursors and CE (Volts)=0.5*m/z+5 for triply-charged precursors. SRM acquisitions were performed with Q1 and Q3 quadrupoles operating at unit resolution, the target scan time was set to 1 s, respectively.

Data Analysis

LC-SRM data were analyzed using Skyline 3.6 [Maclean et al.; "Skyline: an open source document editor for creating and analyzing targeted proteomics experiments; Bioinformatics, 2010, 966-8] Signals with obvious matrix interferences (experiments in biological matrices) were excluded. For absolute quantification of each mAb, labeled/unlabeled peak area ratios were calculated for each SRM transition after verification of coelution profiles. The ratios obtained for the different SRM transitions were used to calculate the corresponding average peptide ratio. mAb levels in the sample processed were deduced from the ratios obtained for the different peptides and the amounts of isotopically-labeled mAb standards spiked.

Calibration Curves Using the LC-MS/MS Method

Calibration curves were established to assess performance of the standards and of the LC-MS/MS method [FIGS. 3A-3B-4A-4B].

Cetuximab (Erbitux®) Calibration Curve Using Labelled Cetuximab Standard.

20 µl serum samples were spiked with five different concentrations of the light mAb, covering a range from 5 µg/ml to 100 µg/ml. Labelled Cetuximab mAb was spiked into each sample at a final concentration of 40 µg/ml. Samples were processed as described prior to LC-MS/MS analysis.

Cetuximab (Erbitux®) Calibration Curve Using Labelled Cetuximab-Like Standard.

The samples were processed as described above. The labelled standard used was labelled Cetuximab-like, spiked into each sample at a final concentration of 40 µg/ml.

Bevacizumab (Avastin®) Calibration Curve Using Labelled Bevacizumab Standard.

20 µl serum samples were spiked with five different concentrations of the light mAb, covering a range from 5 µg/ml to 100 µg/ml. Labelled Bevacizumab mAb was spiked into each sample at a final concentration of 40 µg/ml. Samples were processed as described prior to LC-MS/MS analysis.

Bevacizumab (Avastin®) Calibration Curve Using Labelled Bevacizumab-Like Standard.

The samples were processed as described above. The labelled standard used was labelled Bevacizumab-like, spiked into each sample at a final concentration of 40 µg/ml.

Quality Controls (QC) and mAb-Containing Serum Samples Constitution

Quality controls samples and serum samples containing Cetuximab or Bevacizumab were constituted as described in Table 1 and Table 2.

TABLE 1

Constitution of Quality Control (QC) samples and Erbitux ® serum samples

| Sample | Dosage with labelled cetuximab standard | | | | Dosage with labelled cetuximab-like standard | | | |
|---|---|---|---|---|---|---|---|---|
| | QC1 | QC2 | S1 | S2 | QC1 | QC2 | S1 | S2 |
| Erbitux ® spiked (µg/ml) | 15 | 30 | 25 | 45 | 15 | 30 | 25 | 45 |
| Labelled mAb standard spiked (µg/ml) | 40 | 40 | 40 | 40 | 40 | 40 | 40 | 40 |
| PBS 1X | Qsp 100 µl final volume | | | | | | | |
| Total sample volume | 100 µl | 100 µl | 100 µl | 100 µl | 100 µl | 100 µl | 100 µl | 100 µl |

TABLE 2

Constitution of QC samples and Avastin ® serum samples

| Sample | Dosage with labelled bevacizumab standard | | | | Dosage with labelled bevacizumab-like standard | | | |
|---|---|---|---|---|---|---|---|---|
| | QC1 | QC2 | S1 | S2 | QC1 | QC2 | S1 | S2 |
| Avastin ® spiked (µg/ml) | 15 | 30 | 25 | 45 | 15 | 30 | 25 | 45 |
| Labelled mAb standard spiked (µg/ml) | 40 | 40 | 40 | 40 | 40 | 40 | 40 | 40 |
| PBS 1X | Qsp 100 µl final volume | | | | | | | |
| Total sample volume | 100 µl | 100 µl | 100 µl | 100 µl | 100 µl | 100 µl | 100 µl | 100 µl |

Sample Processing and Digestion

Each sample was made up to a final volume of 100 µl by adding 1×PBS. Pierce™ Protein G Spin plate were used according to the manufacturer's instructions. Briefly, each plate well was washed twice with 200 µl 1×PBS and PBS was discarded using a vacuum manifold. Each serum sample was incubated for 1 h at room temperature on an orbital shaker and then discarded using vacuum manifold. Protein G resin was washed 3 times with 1×PBS. 200 µl Elution buffer (50% Acetonitrile, 0.5% formic acid) was added twice. Each elution fraction was recovered by centrifugation (swinging rotor, 1000 g, 5 min). Elutions were dried in a speed-vacuum and then resuspended with 60 µl of a solution containing 58 µl of 100 mM ammonium bicarbonate and 2 µl 1M Trizma Base. Proteins were digested for 16 h at 37° C. with Trypsin. Digestion was stopped by adding 1% formic acid.

II-Quantification Performances with an Antibody-Like Labelled Standard.

The Cetuximab-like labelled standard is formed by two identical heavy chains and two identical light chains; wherein the heavy chain consists of SEQ ID No1 which is a $V_H$ Trastuzumab (HER) including H-CDR2 from Cetuximab (ERB); and wherein the light chain consists of the Cetuximab light chain of SEQ ID No14.

The Bevacizumab-like labelled standard is formed by two identical heavy chains and two identical light chains; wherein the heavy chain consists of SEQ ID No119; and wherein the light chain consists of the Trastuzumab light chain of SEQ ID No5 or SEQ ID No18.

Labelled Cetuximab is formed by heavy and light chains which are respectively of SEQ ID No13 and 14.

Labelled Bevacizumab is formed by heavy and light chains which are respectively of SEQ ID No15 and 16.

Figure 3A:
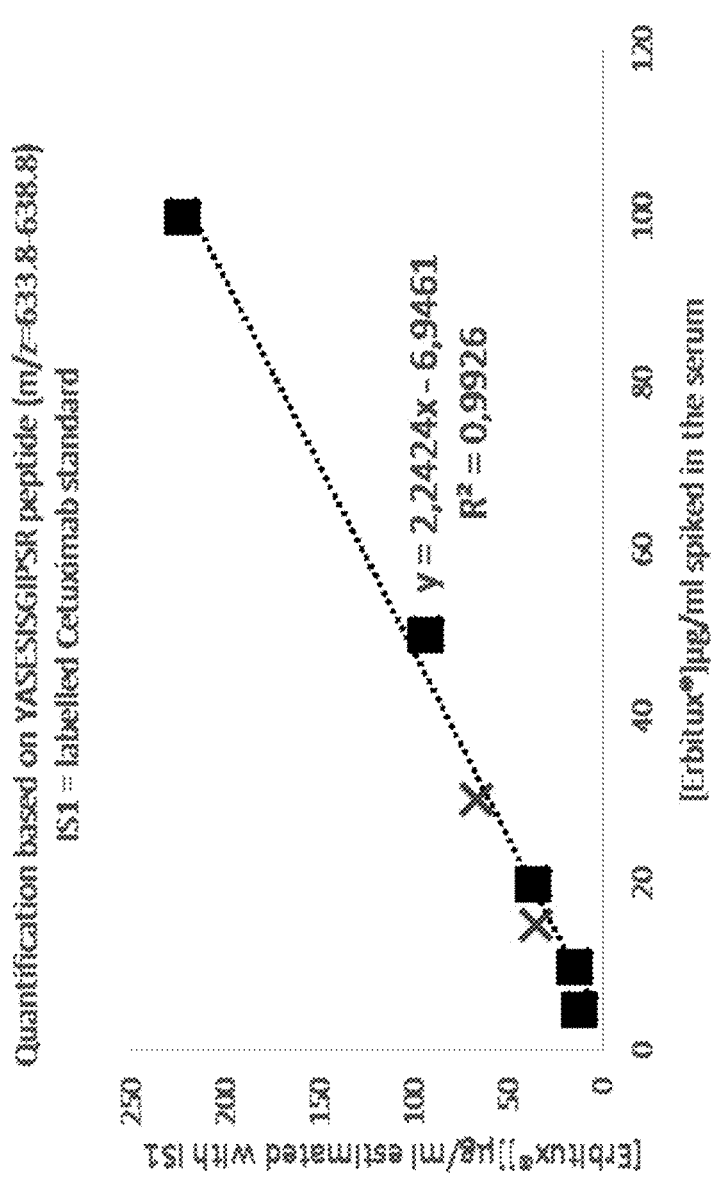
FIG. 3A: Quantification with labelled Cetuximab in human serum. The quantification is based on the YASESIS-GIPSR peptide of SEQ ID No39 (m/z=633.8-638.8) with on x-axis the [Erbitux®] concentration expressed in µg/ml spiked in the serum and on the y-axis the [Erbitux®] concentration estimated with the labelled Cetuximab standard.
Figure 3B:
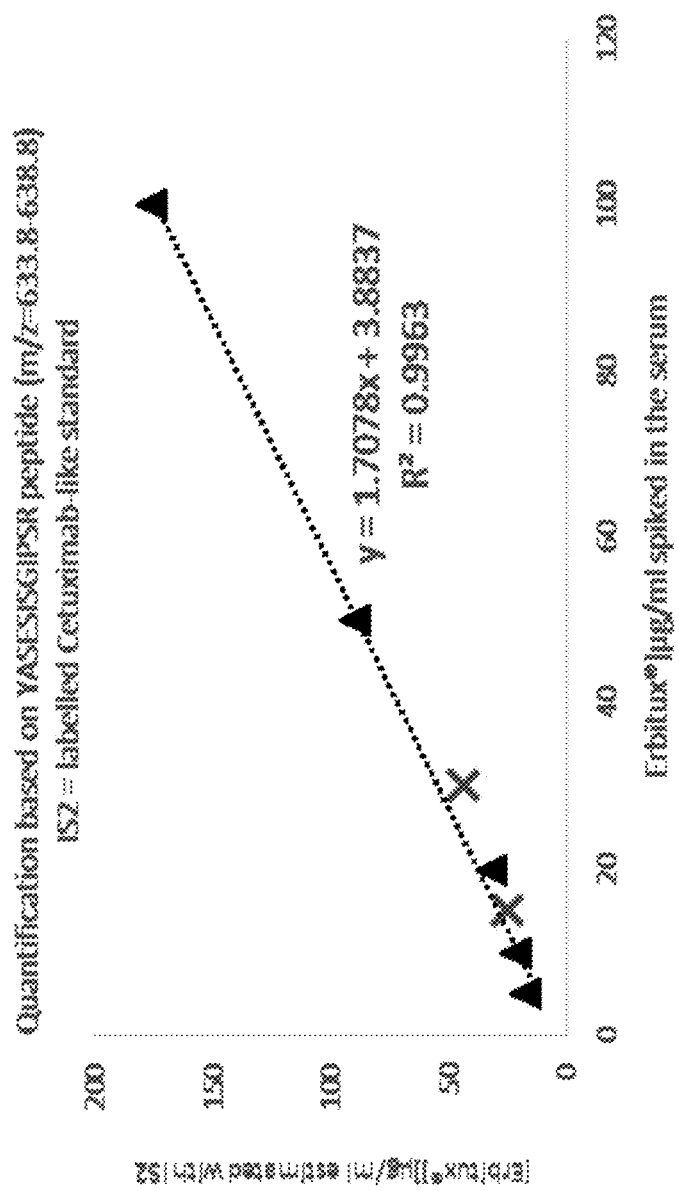
FIG. 3B: Quantification with labelled Cetuximab-like polypeptide. The quantification is based on the YASESIS-GIPSR peptide of SEQ ID No39 (m/z=633.8-638.8) with on x-axis the [Erbitux®] concentration expressed in µg/ml spiked in the serum and on the y-axis the [Erbitux®] concentration estimated with the labelled Cetuximab-like standard.
Figure 4A:
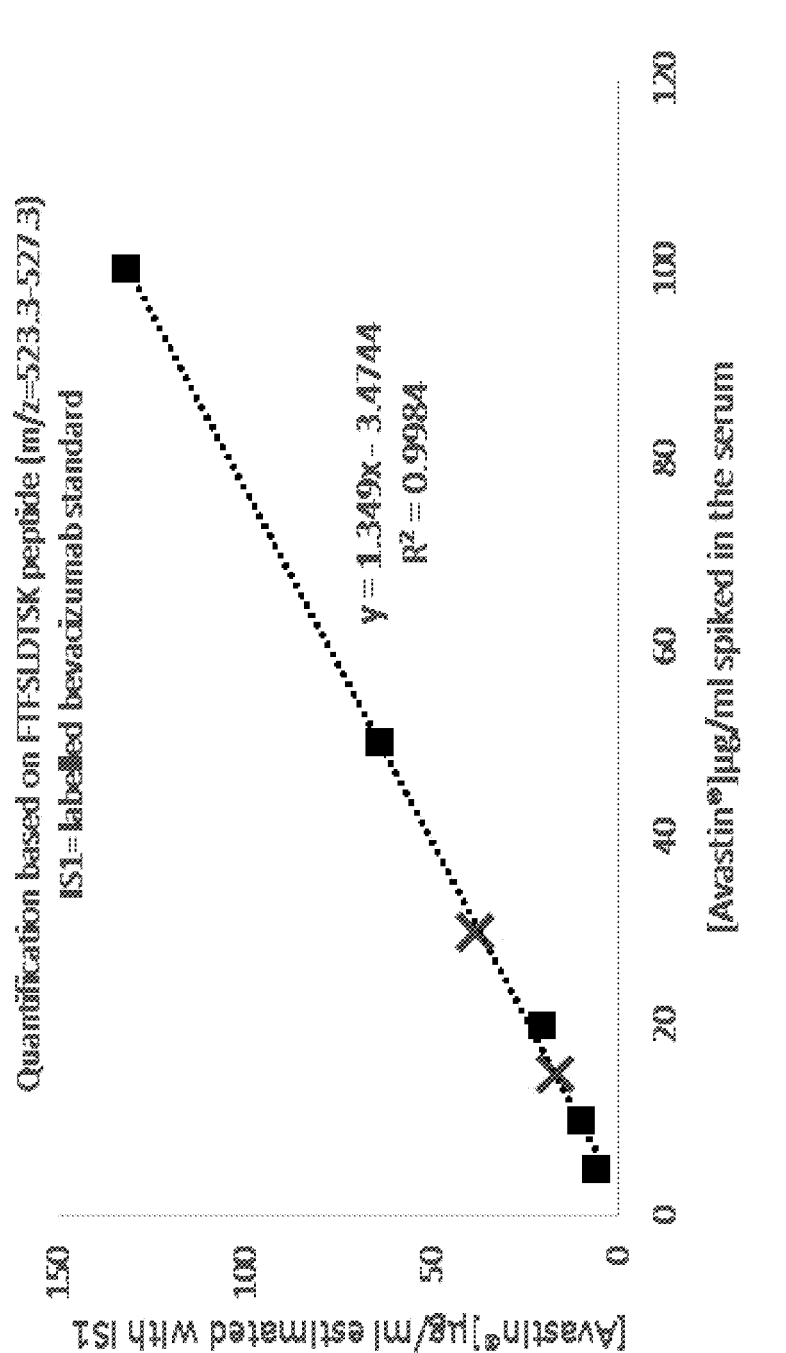
FIG. 4A: Quantification with labelled Bevacizumab in human serum. The quantification is based on the FTFSLDTSK peptide of SEQ ID No43 (m/z=523.3-527.3) with on x-axis the [Avastin®] concentration expressed in µg/ml spiked in the serum and on the y-axis the [Avastin®] concentration estimated with the labelled Bevacizumab standard.
Figure 4B:
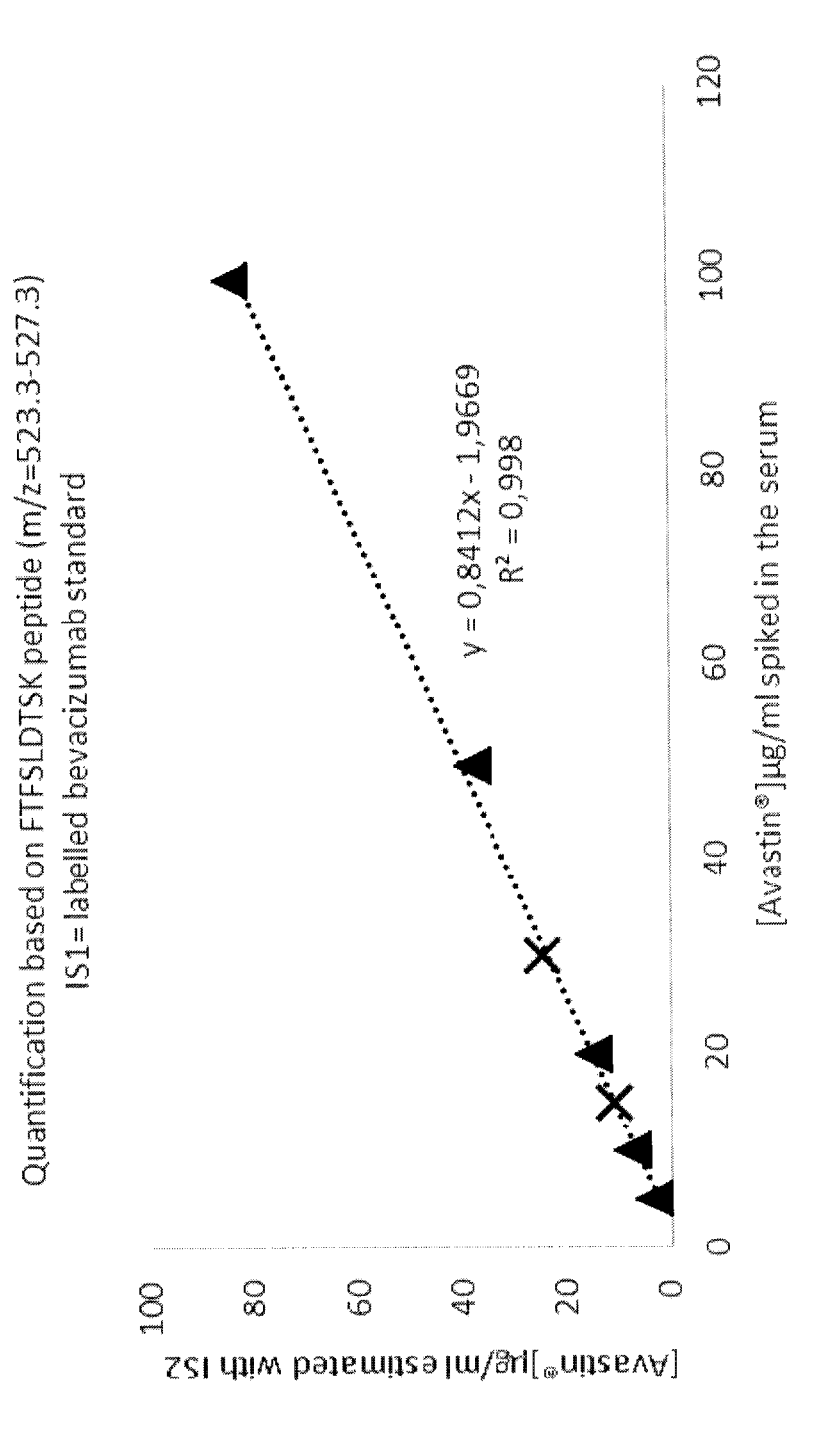
FIG. 4B: Quantification with labelled Bevacizumab-like polypeptide. The quantification is based on the FTFSLDTSK peptide of SEQ ID No43 (m/z=523.3-527.3) with on x-axis the [Avastin®] concentration expressed in µg/ml spiked in the serum and on the y-axis the [Avastin®] concentration estimated with the labelled Bevacizumab-like standard.

As shown in FIGS. 3A-3B and also in FIGS. 4A-4B, both labelled internal standards (100% homologous mAb labelled standard and antibody-like labelled standard) allow to obtain a linear titration curve. The correlation coefficient, $R^2$, for the linear regression was >0.99, for the 4 titration curves. The concentration range of the titration curve performed extended from 0 to 100 µg/ml [FIGS. 3A-3B-4A-4B]. For quantification of Erbitux®, 1 proteotypic tryptic peptide and 3 daughter ions were monitored in both labelled and non-labelled form [FIGS. 3A-3B]. Two quality control samples were performed. For quantification of Avastin®, 1 proteotypic tryptic peptide and 3 daughter ions were monitored in both labelled and non-labelled form [FIGS. 4A-4B]. Two quality control samples were performed.

The concentration estimated for Erbitux® (Cetuximab) spiked in two human serum samples and determined using the labelled Cetuximab and the labelled Cetuximab-like standards were found to be extremely similar. The concentration obtained respectively were 24.1 µg/ml and 24.3 µg/ml for the human serum sample spiked with a theoric 25 µg/ml Erbitux® concentration, they were 43.3 µg/ml and 45.2 µg/ml for the human serum sample spiked with a theoric 45 µg/ml Erbitux® concentration.

| Sample | [Erbitux®] µg/ml theoric | [Erbitux®] µg/ml estimated with labelled Cetuximab (accuracy) | [Erbitux®] µg/ml estimated with labelled Cetuximab-like polypeptide (accuracy) |
|---|---|---|---|
| S1 | 25 | 24.1 (96.5%) | 24.3 (97.3%) |
| S2 | 45 | 43.3 (96.2%) | 45.2 (99.5%) |

The data obtained for Bevacizumab are as shown herebelow.

| Sample | [Avastin®] µg/ml theoric | [Avastin®] µg/ml estimated with labelled Bevacizumab (accuracy) | [Avastin®] µg/ml estimated with labelled Bevacizumab-like polypeptide (accuracy) |
|---|---|---|---|
| S1 | 25 | 26.3 (105.2%) | 27.0 (108%) |
| S2 | 45 | 49.5 (110%) | 51.6 (114%) |

These results provide evidence that an antibody-like protein, as described above, can be used for quantifying one or more therapeutic antibodies in a human serum samples, leading to quantification performances similar to the ones obtained using 100% identical labelled mAb standard(s).

```
                        SEQUENCE LISTING

SEQ  Type     Description

1  Peptide  Antibody-like protein constitutive fragment
              V_H Trastuzumab (HER) including H-CDR2 from Cetuximab (ERB)

2  Peptide  Antibody-like protein constitutive fragment
              V_H Trastuzumab (HER) including H-CDR2 from Bevacizumab (AVA)

3  Peptide  Antibody-like protein constitutive fragment
              Fc fragment from Trastuzumab (HER) with << Knob >> mutation
              (T366W); and one additional Cysteine residue (S354C)

4  Peptide  Antibody-like protein constitutive fragment
              Fc fragment from Trastuzumab (HER) with << Hole >> mutation
              (T366S,
              L368A, and Y407V); and one additional Cysteine residue (Y349C)

5  Peptide  Antibody-like protein constitutive fragment
              Trastuzumab (HER) light chain
```

SEQUENCE LISTING

| SEQ | Type | Description |
| --- | --- | --- |
| 6 | Peptide | Antibody-like protein constitutive fragment Trastuzumab (HER) heavy chain including H-CDR2 from Cetuximab (ERB) and Fc fragment from Trastuzumab (HER) with << Knob >> mutation |
| 7 | Peptide | Antibody-like protein constitutive fragment Trastuzumab (HER) heavy chain including H-CDR2 from Bevacizumab (AVA) and Fc fragment from Trastuzumab (HER) with << Hole >> mutation |
| 8 | Peptide | Antibody-like protein constitutive fragment $V_H$ Trastuzumab (HER) construct including H-CDR2 from Nivolumab |
| 9 | Peptide | Antibody-like protein constitutive fragment $V_L$ Trastuzumab (HER) construct including L-CDR2 from Nivolumab |
| 10 | Peptide | Antibody-like protein constitutive fragment $V_H + C_H$ (heavy chain) Cetuximab construct including H-CDR2 from Bevacizumab |
| 11 | Peptide | Antibody-like protein constitutive fragment $V_H + C_H$ (heavy chain) Trastuzumab construct including H-CDR2 from Bevacizumab |
| 12 | Peptide | Antibody-like protein constitutive fragment $V_L + C_L$ (light chain) Trastuzumab construct including L-CDR2 from Bevacizumab |
| 13 | Peptide | Reference Cetuximab heavy chain |
| 14 | Peptide | Reference Cetuximab light chain |
| 15 | Peptide | Reference Bevacizumab heavy chain |
| 16 | Peptide | Reference Bevacizumab light chain |
| 17 | Peptide | Reference Trastuzumab heavy chain |
| 18 | Peptide | Reference Trastuzumab light chain |
| 19 | Peptide | Reference Nivolumab heavy chain |
| 20 | Peptide | Reference Nivolumab light chain |
| 21 | Peptide | Reference Infliximab heavy chain |
| 22 | Peptide | Reference Infliximab light chain |
| 23 | Peptide | Reference Adalimumab heavy chain |
| 24 | Peptide | Reference Adalimumab light chain |
| 25 | Peptide | Reference Certolizumab heavy chain |
| 26 | Peptide | Reference Certolizumab light chain |
| 27 | Peptide | Reference Golimumab heavy chain |
| 28 | Peptide | Reference Golimumab light chain |
| 29 | Peptide | Reference Rituximab heavy chain |
| 30 | Peptide | Reference Rituximab light chain |
| 31 | Peptide | Reference Secukinumab heavy chain |
| 32 | Peptide | Reference Secukinumab light chain |
| 33 | Peptide | Reference Ipilimumab heavy chain |
| 34 | Peptide | Reference Ipilimumab light chain |
| 35 | Peptide | Tryptic peptide with H-CDR1 from Cetuximab (ERB) |

-continued

| SEQUENCE LISTING | | |
|---|---|---|
| SEQ | Type | Description |
| 36 | Peptide | Tryptic peptide with H-CDR2 from Cetuximab (ERB) |
| 37 | Peptide | Tryptic peptide with H-CDR3 from Cetuximab (ERB) |
| 38 | Peptide | Tryptic peptide with L-CDR1 from Cetuximab (ERB) |
| 39 | Peptide | Tryptic peptide with L-CDR2 from Cetuximab (ERB) |
| 40 | Peptide | Tryptic peptide with L-CDR3 from Cetuximab (ERB) |
| 41 | Peptide | Tryptic peptide with H-CDR1 from Bevacizumab |
| 42 | Peptide | Tryptic peptide with H-CDR2 from Bevacizumab - Fragment 1 |
| 43 | Peptide | Tryptic peptide with H-CDR2 from Bevacizumab - Fragment 2 |
| 44 | Peptide | Tryptic peptide with H-CDR3 from Bevacizumab - Fragment 1 |
| 45 | Peptide | Tryptic peptide with H-CDR3 from Bevacizumab - Fragment 2 |
| 46 | Peptide | Tryptic peptide with L-CDR1 from Bevacizumab |
| 47 | Peptide | Tryptic peptide with L-CDR2 from Bevacizumab |
| 48 | Peptide | Tryptic peptide with L-CDR3 from Bevacizumab |
| 49 | Peptide | Tryptic peptide with H-CDR1 from Nivolumab |
| 50 | Peptide | Tryptic peptide with H-CDR2 from Nivolumab |
| 51 | Peptide | Tryptic peptide with H-CDR3 from Nivolumab |
| 52 | Peptide | Tryptic peptide with L-CDR1 from Nivolumab |
| 53 | Peptide | Tryptic peptide with L-CDR2 from Nivolumab |
| 54 | Peptide | Tryptic peptide with L-CDR3 from Nivolumab |
| 55 | Peptide | Tryptic peptide with H-CDR1 from Rituximab |
| 56 | Peptide | Tryptic peptide with H-CDR2 from Rituximab - Fragment 1 |
| 57 | Peptide | Tryptic peptide with H-CDR2 from Rituximab - Fragment 2 |
| 58 | Peptide | Tryptic peptide with H-CDR3 from Rituximab - Fragment 1 |
| 59 | Peptide | Tryptic peptide with H-CDR3 from Rituximab - Fragment 2 |
| 60 | Peptide | Tryptic peptide with L-CDR1 from Rituximab |
| 61 | Peptide | Tryptic peptide with L-CDR2 from Rituximab |
| 62 | Peptide | Tryptic peptide with L-CDR3 from Rituximab |
| 63 | Peptide | Tryptic peptide with H-CDR1 from Secukinumab |
| 64 | Peptide | Tryptic peptide with H-CDR2 from Secukinumab |
| 65 | Peptide | Tryptic peptide with H-CDR3 from Secukinumab - Fragment 1 |
| 66 | Peptide | Tryptic peptide with H-CDR3 from Secukinumab - Fragment 2 |
| 67 | Peptide | Tryptic peptide with L-CDR1 from Secukinumab |
| 68 | Peptide | Tryptic peptide with L-CDR2 from Secukinumab |
| 69 | Peptide | Tryptic peptide with L-CDR3 from Secukinumab |
| 70 | Peptide | Tryptic peptide with H-CDR1 from Ipilimumab |
| 71 | Peptide | Tryptic peptide with H-CDR2 from Ipilimumab |
| 72 | Peptide | Tryptic peptide with H-CDR3 from Ipilimumab - Fragment 1 |
| 73 | Peptide | Tryptic peptide with H-CDR3 from Ipilimumab - Fragment 2 |

-continued

| SEQ | Type | Description |
|---|---|---|
| 74 | Peptide | Tryptic peptide with L-CDR1 from Ipilimumab |
| 75 | Peptide | Tryptic peptide with L-CDR2 from Ipilimumab |
| 76 | Peptide | Tryptic peptide with L-CDR3 from Ipilimumab |
| 77 | Peptide | H-CDR1 from Nivolumab |
| 78 | Peptide | H-CDR2 from Nivolumab |
| 79 | Peptide | H-CDR3 from Nivolumab |
| 80 | Peptide | L-CDR1 from Nivolumab |
| 81 | Peptide | L-CDR2 from Nivolumab |
| 82 | Peptide | L-CDR3 from Nivolumab |
| 83 | Peptide | H-CDR1 from Cetuximab |
| 84 | Peptide | H-CDR2 from Cetuximab |
| 85 | Peptide | H-CDR3 from Cetuximab |
| 86 | Peptide | L-CDR1 from Cetuximab |
| 87 | Peptide | L-CDR2 from Cetuximab |
| 88 | Peptide | L-CDR3 from Cetuximab |
| 89 | Peptide | H-CDR1 from Bevacizumab |
| 90 | Peptide | H-CDR2 from Bevacizumab |
| 91 | Peptide | H-CDR3 from Bevacizumab |
| 92 | Peptide | L-CDR1 from Bevacizumab |
| 93 | Peptide | L-CDR2 from Bevacizumab |
| 94 | Peptide | L-CDR3 from Bevacizumab |
| 95 | Peptide | H-CDR1 from Rituximab |
| 96 | Peptide | H-CDR2 from Rituximab |
| 97 | Peptide | H-CDR3 from Rituximab |
| 98 | Peptide | L-CDR1 from Rituximab |
| 99 | Peptide | L-CDR2 from Rituximab |
| 100 | Peptide | L-CDR3 from Rituximab |
| 101 | Peptide | H-CDR1 from Secukinumab |
| 102 | Peptide | H-CDR2 from Secukinumab |
| 103 | Peptide | H-CDR3 from Secukinumab |
| 104 | Peptide | L-CDR1 from Secukinumab |
| 105 | Peptide | L-CDR2 from Secukinumab |
| 106 | Peptide | L-CDR3 from Secukinumab |
| 107 | Peptide | H-CDR1 from Ipilimumab |
| 108 | Peptide | H-CDR2 from Ipilimumab |
| 109 | Peptide | H-CDR3 from Ipilimumab |
| 110 | Peptide | L-CDR1 from Ipilimumab |

SEQUENCE LISTING

| SEQ | Type | Description |
|---|---|---|
| 111 | Peptide | L-CDR2 from Ipilimumab |
| 112 | Peptide | L-CDR3 from Ipilimumab |
| 113 | Peptide | Antibody-like protein constitutive fragment Heavy chain enabling to perform the multiplex quantification of Nivolumab and Cetuximab |
| 114 | Peptide | Antibody-like protein constitutive fragment Light chain enabling to perform the multiplex quantification of Nivolumab and Cetuximab |
| 115 | Peptide | Antibody-like protein constitutive fragment Heavy Chain A (Nivolumab) |
| 116 | Peptide | Antibody-like protein constitutive fragment Heavy Chain B (Cetuximab) |
| 117 | Peptide | Antibody-like protein constitutive fragment Light Chain A (Nivolumab) |
| 118 | Peptide | Antibody-like protein constitutive fragment Light Chain B (Cetuximab) |
| 119 | Peptide | Antibody-like protein constitutive fragment $V_H$ Cetuximab including H-CDR2 from Bevacizumab |

SEQ ID No 1
EVQLVESGGGLVQPGGSLRLSCAASGFNIKDTYIHWVRQAPGKGLEWLGVIWSGG
NTDYNTPFTSRLSINKDNSKTAYLQMNSLRAEDTAVYYCSRWGGDGFYAMDY
WGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVE

SEQ ID No 2
EVQLVESGGGLVQPGGSLRLSCAASGFNIKDTYIHWVRQAPGKGLEWVGWINTY
TGEPTYAADFKRRFTFSLDTSKSTAYLQMNSLRAEDTAVYYCSRWGGDGFYAMD
YWGQGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVE

SEQ ID No 3
KVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKE
YKCKVSNKALPAPIEKTISKAKGQPREPQVYTLPPCREEMTKNQVSLWCLVKGFY
PSDIAVEWESNGQPENNYKTTPPVLDSDGSFFLYSKLTVDKSRWQQGNVFSCSVM
HEALHNHYTQKSLSLSPGK

SEQ ID No 4
KVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKE
YKCKVSNKALPAPIEKTISKAKGQPREPQVCTLPPSREEMTKNQVSLSCAVKGFYP
SDIAVEWESNGQPENNYKTTPPVLDSDGSFFLVSKLTVDKSRWQQGNVFSCSVMH
EALHNHYTQKSLSLSPGK

SEQ ID No 5
DIQMTQSPSSLSASVGDRVTITCRASQDVNTAVAWYQQKPGKAPKLLIYSASFLYS
GVPSRFSGSRSGTDFTLTISSLQPEDFATYYCQQHYTTPPTFGQGTKVEIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No 6
EVQLVESGGGLVQPGGSLRLSCAASGFNIKDTYIHWVRQAPGKGLEWLGVIWSGG
NTDYNTPFTSRLSINKDNSKTAYLQMNSLRAEDTAVYYCSRWGGDGFYAMDY
WGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKA
LPAPIEKTISKAKGQPREPQVYTLPPCREEMTKNQVSLWCLVKGFYPSDIAVEWES
NGQPENNYKTTPPVLDSDGSFFLYSKLTVDKSRWQQGNVFSCSVMHEALHNHYT
QKSLSLSPGK

SEQ ID No 7
EVQLVESGGGLVQPGGSLRLSCAASGFNIKDTYIHWVRQAPGKGLEWVGWINTY
TGEPTYAADFKRRFTFSLDTSKSTAYLQMNSLRAEDTAVYYCSRWGGDGFYAMD
YWGQGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVE

| SEQ Type | Description |
|---|---|

PKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNK
ALPAPIEKTISKAKGQPREPQVCTLPPSREEMTKNQVSLSCAVKGFYPSDIAVEWES
NGQPENNYKTTPPVLDSDGSFFLVSKLTVDKSRWQQGNVFSCSVMHEALHNHYT
QKSLSLSPGK

SEQ ID No 8
QVQLVESGGGLVQPGGSLRLSCAASGFNIKDTYIHWVRQAPGKGLEWVARVIWY
DGSKRYYADSVKGRFTISRDNSKNTLFLQMNSLRAEDTAVYYCSRWGGDGFYAM
DYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNH
YTQKSLSLSPG

SEQ ID No 9
DIQMTQSPSSLSASVGDRVTITCRASQDVNTAVAWYQQKPGKAPKLLIYDASNRA
TGIPARFSGSGSGTDFTLTISSLQPEDFATYYCQQHYTTPPTFGQGTKVEIKRTVAA
PSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No 10
QVQLKQSGPGLVQPSQSLSITCTVSGFSLTNYGVHWVRQAPGKGLEWVGWINTYT
GEPTYAADFKRRFTESLDTSKSTAYLKMNSLQSNDTAIYYCARALTYYDYEFAW
GQGTLVTVSAASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQ
KSLSLSPGK

SEQ ID No 11
QVQLVESGGGLVQPGGSLRLSCAASGFNIKDTYIHWVRQAPGKGLEWVGWINTY
TGEPTYAADFKRRFTFSLDTSKSTAYLQMNSLRAEDTAVYYCSRWGGDGFYAMD
YWGQGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYT
QKSLSLSPG

SEQ ID No 12
DIQMTQSPSSLSASVGDRVTITCRASQDVNTAVAWYQQKPGKAPKLLIYDASNRA
TGIPARFSGSGSGTDFTLTISSLQPEDFATYYCQQHYTTPPTFGQGTKVEIKRTVAA
PSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No 13
QVQLKQSGPGLVQPSQSLSITCTVSGFSLTNYGVHWVRQSPGKGLEWLGVIWSGG
NTDYNTPFTSRLSINKDNSKSQVFFKMNSLQSNDTAIYYCARALTYYDYEFAYWG
QGTLVTVSAASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQK
SLSLSPGK

SEQ ID No 14
DILLTQSPVILSVSPGERVSFSCRASQSIGTNIHWYQQRTNGSPRLLIKYASESISGIP
SRFSGSGSGTDFTLSINSVESEDIADYYCQQNNNWPTTFGAGTKLELKRTVAAPSV
FIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

SEQ ID No 15
EVQLVESGGGLVQPGGSLRLSCAASGYTFTNYGMNWVRQAPGKGLEWVGWINT
YTGEPTYAADFKRRFTFSLDTSKSTAYLQMNSLRAEDTAVYYCAKYPHYYGSSH
WYFDVWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVD
KKVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCK

SEQUENCE LISTING

VSNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMHEALH
NHYTQKSLSLSPGK

SEQ ID No 16
DIQMTQSPSSLSASVGDRVTITCSASQDISNYLNWYQQKPGKAPKVLIYFTSSLHSG
VPSRFSGSGSGTDFTLTISSLQPEDFATYYCQQYSTVPWTFGQGTKVEIKRTVAAPS
VFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

SEQ ID No 17
EVQLVESGGGLVQPGGSLRLSCAASGFNIKDTYIHWVRQAPGKGLEWVARIYPTN
GYTRYADSVKGRFTISADTSKNTAYLQMNSLRAEDTAVYYCSRWGGDGFYAMD
YWGQGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYT
QKSLSLSPG

SEQ ID No 18
DIQMTQSPSSLSASVGDRVTITCRASQDVNTAVAWYQQKPGKAPKLLIYSASFLYS
GVPSRFSGSRSGTDFTLTISSLQPEDFATYYCQQHYTTPPTFGQGTKVEIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No 19
QVQLVESGGGVVQPGRSLRLDCKASGITFSNSGMHWVRQAPGKGLEWVAVIWY
DGSKRYYADSVKGRFTISRDNSKNTLFLQMNSLRAEDTAVYYCATNDDWGQGT
LVTVSSASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVESKYGPPC
PPCPAPEFLGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSIEKTIS
KAKGQPREPQVYTLPPSQEEMTKNQVSLTCLVKGFYPSDIAVEWESNGQPENNYK
TTPPVLDSDGSFFLYSRLTVDKSRWQEGNVFSCSVMHEALHNHYTQKSLSLSLGK

SEQ ID No 20
EIVLTQSPATLSLSPGERATLSCRASQSVSSYLAWYQQKPGQAPRLLIYDASNRAT
GIPARFSGSGSGTDFTLTISSLEPEDFAVYYCQQSSNWPRTFGQGTKVEIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No 21
EVKLEESGGGLVQPGGSMKLSCVASGFIFSNHWMNWVRQSPEKGLEWVAEIRSK
SINSATHYAESVKGRFTISRDDSKSAVYLQMTDLRTEDTGVYYCSRNYYGSTYDY
WGQGTTLTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQ
KSLSLSPGK

SEQ ID No 22
DILLTQSPAILSVSPGERVSFSCRASQFVGSSIHWYQQRTNGSPRLLIKYASESMSGI
PSRFSGSGSGTDFTLSINTVESEDIADYYCQQSHSWPFTFGSGTNLEVKRTVAAPSV
FIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

SEQ ID No 23
EVQLVESGGGLVQPGRSLRLSCAASGFTFDDYAMHWVRQAPGKGLEWVSAITWN
SGHIDYADSVEGRFTISRDNAKNSLYLQMNSLRAEDTAVYYCAKVSYLSTASSLD
YWGQGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYT
QKSLSLSPGK

SEQUENCE LISTING

| SEQ Type | Description |
|---|---|

SEQ ID No 24
DIQMTQSPSSLSASVGDRVTITCRASQGIRNYLAWYQQKPGKAPKLLIYAASTLQS
GVPSRFSGSGSGTDFTLTISSLQPEDVATYYCQRYNRAPYTFGQGTKVEIKRTVAA
PSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No 25
EVQLVESGGGLVQPGGSLRLSCAASGYVFTDYGMNWVRQAPGKGLEWMGWINT
YIGEPIYADSVKGRFTFSLDTSKSTAYLQMNSLRAEDTAVYYCARGYRSYAMDY
WGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEP
KSCDKTHTCAA

SEQ ID No 26
DIQMTQSPSSLSASVGDRVTITCKASQNVGTNVAWYQQKPGKAPKALIYSASFLY
SGVPYRFSGSGSGTDFTLTISSLQPEDFATYYCQQYNIYPLTFGQGTKVEIKRTVAA
PSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No 27
QVQLVESGGGVVQPGRSLRLSCAASGFIFSSYAMHWVRQAPGNGLEWVAFMSYD
GSNKKYADSVKGRFTISRDNSKNTLYLQMNSLRAEDTAVYYCARDRGIAAGGNY
YYYGMDVISSQGTTVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTK
VDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHE
ALHNHYTQKSLSLSPGK

SEQ ID No 28
EIVLTQSPATLSLSPGERATLSCRASQSVYSYLAWYQQKPGQAPRLLIYDASNRAT
GIPARFSGSGSGTDFTLTISSLEPEDFAVYYCQQRSNWPPFTFGPGTKVDIKRTVAA
PSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No 29
QVQLQQPGAELVKPGASVKMSCKASGYTFTSYNMHWVKQTPGRGLEWIGAIYPG
NGDTSYNQKFKGKATLTADKSSSTAYMQLSSLTSEDSAVYYCARSTYYGGDWYF
NVWGAGTTVTVSAASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHY
TQKSLSLSPGK

SEQ ID No 30
QIVLSQSPAILSASPGEKVTMTCRASSSVSYIHWFQQKPGSSPKPWIYATSNLASGV
PVRFSGSGSGTSYSLTISRVEAEDAATYYCQQWTSNPPTFGRGTKLEIKRTVAAPS
VFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

SEQ ID No 31
EVQLVESGGGLVQPGGSLRLSCAASGFTFSNYWMNWVRQAPGKGLEWVAAINQ
DGSEKYYVGSVKGRFTISRDNAKNSLYLQMNSLRVEDTAVYYCVRDYYDILTDY
YIHYWYFDLWGRGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNT
KVDKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCSVMH
EALHNHYTQKSLSLSPGK

SEQ ID No 32
EIVLTQSPGTLSLSPGERATLSCRASQSVSSSYLAWYQQKPGQAPRLLIYGASSRAT
GIPDRFSGSGSGTDFTLTISRLEPEDFAVYYCQQYGSSPCTFGQGTRLEIKRTVAAPS
VFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

SEQ ID No 33
QVQLVESGGGVVQPGRSLRLSCAASGFTFSSYTMHWVRQAPGKGLEWVTFISYD
GNNKYYADSVKGRFTISRDNSKNTLYLQMNSLRAEDTAIYYCARTGWLGPFDYW
GQGTLVTVSSASTKGPSVFPLAPSSKSTSGGTAALGCLVKDYFPEPVTVSWNSGAL

SEQUENCE LISTING

```
SEQ Type    Description

TSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQK
SLSLSPGK

SEQ ID No 34
EIVLTQSPGTLSLSPGERATLSCRASQSVGSSYLAWYQQKPGQAPRLLIYGAFSRAT
GIPDRFSGSGSGTDFTLTISRLEPEDFAVYYCQQYGSSPWTFGQGTKVEIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No 35
QSGPGLVQPSQSLSITCTVSGFSLTNYGVHWVR

SEQ ID No 36
GLEWLGVIWSGGNTDYNTPFTSR

SEQ ID No 37
ARALTYYDYEFAYWGQGTLVTVSAASTK

SEQ ID No 38
ASQSIGTNIHWYQQR

SEQ ID No 39
YASESISGIPSR

SEQ ID No 40
FSGSGSGTDFTLSINSVESEDIADYYCQQNNNWPTTFGAGTK

SEQ ID No 41
LSCAASGYTFTNYGMNWVR

SEQ ID No 42
GLEWVGWINTYTGEPTYAADFK

SEQ ID No 43
FTFSLDTSK

SEQ ID No 44
AEDTAVYYCAK

SEQ ID No 45
AKYPHYYGSSHWYFDVWGQGTLVTVSSASTK

SEQ ID No 46
VTITCSASQDISNYLNWYQQK

SEQ ID No 47
VLIYFTSSLHSGVPSR

SEQ ID No 48
FSGSGSGTDFTLTISSLQPEDFATYYCQQYSTVPWTFGQGTK

SEQ ID No 49
ASGITFSNSGMHWVR

SEQ ID No 50
GLEWVAVIWYDGSK

SEQ ID No 51
AEDTAVYYCATNDDYWGQGTLVTVSSASTK

SEQ ID No 52
ASQSVSSYLAWYQQK

SEQ ID No 53
LLIYDASNR

SEQ ID No 54
FSGSGSGTDFTLTISSLEPEDFAVYYCQQSSNWPRT

SEQ ID No 55
ASGYTFTSYNMHWVK
```

SEQUENCE LISTING

| SEQ Type | Description |
|---|---|
| SEQ ID No 56 | GLEWIGAIYPGNGDTSYNQK |
| SEQ ID No 57 | ATLTADK |
| SEQ ID No 58 | SSSTAYMQLSSLTSEDSAVYYCAR |
| SEQ ID No 59 | ARSTYYGGDWYFNVWGAGTTVTVSAASTK |
| SEQ ID No 60 | ASSSVSYIHWFQQK |
| SEQ ID No 61 | PWIYATSNLASGVPVR |
| SEQ ID No 62 | VEAEDAATYYCQQWTSNPPTFGGGTK |
| SEQ ID No 63 | LSCAASGFTFSNYWMNWVR |
| SEQ ID No 64 | GLEWVAAINQDGSEK |
| SEQ ID No 65 | VEDTAVYYCVR |
| SEQ ID No 66 | RDYYDILTDYYIHYWYFDLWGR |
| SEQ ID No 67 | ASQSVSSSYLAWYQQK |
| SEQ ID No 68 | LLIYGASSR |
| SEQ ID No 69 | LEPEDFAVYYCQQYGSSPCTFGQGTR |
| SEQ ID No 70 | LSCAASGFTFSSYTMHWVR |
| SEQ ID No 71 | GLEWVTFISYDGNNK |
| SEQ ID No 72 | AEDTAIYYCAR |
| SEQ ID No 73 | ARTGWLGPFDYWGQGTLVTVSSASTK |
| SEQ ID No 74 | ASQSVGSSYLAWYQQK |
| SEQ ID No 75 | LLIYGAFSR |
| SEQ ID No 76 | LEPEDFAVYYCQQYGSSPWTFGQGTK |
| SEQ ID No 77 | GITFSNSG |
| SEQ ID No 78 | VIWYDGSKRYYADSVKG |
| SEQ ID No 79 | ATNDDY |
| SEQ ID No 80 | QSVSSY |

-continued

SEQUENCE LISTING

| SEQ Type | Description |
|---|---|

SEQ ID No 81
DAS

SEQ ID No 82
QQSSNWPRT

SEQ ID No 83
GFSLTNYG

SEQ ID No 84
IWSGGNT

SEQ ID No 85
ARALTYYDYEFAY

SEQ ID No 86
QSIGTN

SEQ ID No 87
YAS

SEQ ID No 88
QQNNNWPTT

SEQ ID No 89
GYTFTNYG

SEQ ID No 90
GWINTYTGEPT

SEQ ID No 91
AKYPHYYGSSHWYFDVW

SEQ ID No 92
QDISNY

SEQ ID No 93
FTS

SEQ ID No 94
QQYSTVPW

SEQ ID No 95
GYTFTSYN

SEQ ID No 96
IYPGNGDTS

SEQ ID No 97
ARSTYYGGDWYFNV

SEQ ID No 98
SSVSY

SEQ ID No 99
ATS

SEQ ID No 100
QQWTSNPPT

SEQ ID No 101
GFTFSNYW

SEQ ID No 102
AINQDGSEK

SEQ ID No 103
RDYYDILTDYYIHYWYFDL

SEQ ID No 104
QSVSSSY

SEQ ID No 105
GAS

```
                          SEQUENCE LISTING

SEQ Type    Description

SEQ ID No 106
QQYGSSPC

SEQ ID No 107
GFTFSSYT

SEQ ID No 108
TFISYDGNNK

SEQ ID No 109
ARTGWLGPFDY

SEQ ID No 110
QSVGSSY

SEQ ID No 111
GAF

SEQ ID No 112
QQYGSSPWT

SEQ ID No 113
EVQLVESGGGLVQPGGSLRLSCKASGITFSNSGMHWVRQAPGKGLEWLGVIWSG
GNTDYNTPFTSRFTISADTSKNTAYLQMNSLRAEDTAVYYCSRWGGDGFYAMDY
WGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQ
KSLSLSPG

SEQ ID No 114
DIQMTQSPSSLSASVGDRVTITCRASQSVSSYLAWYQQKPGKAPKLLIKYASESISG
IPSRFSGSRSGTDFTLTISSLQPEDFATYYCQQHYTTPPTFGQGTKVEIKRTVAAPSV
FIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

SEQ ID No 115
EVQLVESGGGLVQPGGSLRLSCAASGFNIKDTYIHWVRQAPGKGLEWVAVIWYD
GSKRYYADSVKGRFTISADTSKNTAYLQMNSLRAEDTAVYYCSRWGGDGFYAM
DYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNH
YTQKSLSLSPGK

SEQ ID No 116
EVQLVESGGGLVQPGGSLRLSCAASGFNIKDTYIHWVRQAPGKPGKGLEWLGVIW
SGGNTDYNTPFTSRLSINKDNSKNTAYLQMNSLRAEDTAVYYCSRWGGDGFYAM
DYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNH
YTQKSLSLSPG

SEQ ID No 117
DIQMTQSPSSLSASVGDRVTLSCRASQSVSSYLAWYQQKPGKAPRLLIYDASNRAT
GVPSRFSGSRSGTDFTLTISSLQPEDFATYYCQQHYTTPPTFGQGTKVEIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No 118
DIQMTQSPSSLSASVGDRVTITCRASQSIGTNIHWYQQRTNGSPRLLIKYASESISGI
PSRFSGSRSGTDFTLTISSLQPEDFATYYCQQHYTTPPTFGQGTKVEIKRTVAAPSV
FIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC
```

SEQUENCE LISTING

| SEQ Type | Description |
|---|---|

SEQ ID No 119
EVQLVESGGGLVQPGGSLRLSCAASGFNIKDTYIHWVRQAPGKGLEWVGWINTY
TGEPTYAADFKRRFTFSLDTSKSTAYLQMNSLRAEDTAVYYCSRWGGDGFYAMD
YWGQGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYT
QKSLSLSPGK

The invention claimed is:

1. A process for quantifying one or more therapeutic antibodies in a sample of an individual comprising the steps of:
   a) adding to a test sample which contains therapeutic antibodies a known amount of one or more labeled forms of a labeled chimeric non-therapeutic antibody-like protein, whereby a pre-proteolysis sample is provided,
   b) subjecting the pre-proteolysis sample to an enzyme proteolysis, so as to provide a proteolysis sample comprising (i) proteolysis labeled peptides derived from the labeled antibody-like proteins and (ii) proteolysis peptides derived from the therapeutic antibody contained in the test sample,
   c) determining by mass spectrometric analysis the ratio between (i) one or more selected proteolysis labeled peptides and (ii) one or more corresponding proteolysis peptides derived from said therapeutic antibody,
   d) calculating from the ratio determined at step c) the amount of said therapeutic antibody in the test sample;
characterized in that the labeled chimeric non-therapeutic antibody-like protein is structurally similar to a plurality of reference therapeutic antibodies, and comprises an enzyme cleavable peptide sequence of a hypervariable region derived from each one of said plurality of reference therapeutic antibodies.

2. A process for quantifying one or more therapeutic antibodies in a sample of an individual comprising the steps of:
   a) adding to a test sample which contains therapeutic antibodies a known amount of a composition comprising a labeled chimeric non-therapeutic antibody-like protein, whereby a pre-proteolysis sample is provided,
   b) subjecting the pre-proteolysis sample to an enzyme proteolysis, so as to provide a proteolysis sample comprising (i) proteolysis labeled peptides derived from the labeled antibody-like proteins and (ii) proteolysis peptides derived from the therapeutic antibody contained in the test sample,
   c) determining by mass spectrometric analysis the ratio between (i) one or more selected proteolysis labeled peptides and (ii) one or more corresponding proteolysis peptides derived from said therapeutic antibody,
   d) calculating from the ratio determined at step c) the amount of said therapeutic antibody in the test sample;

characterized in that the labeled chimeric non-therapeutic antibody-like protein is structurally similar to a plurality of reference therapeutic antibodies, and comprises an enzyme cleavable peptide sequence of a hypervariable region derived from each one of said plurality of reference therapeutic antibodies.

3. The process according to claim 1, wherein the chimeric antibody-like protein is labelled with a stable isotope.

4. The process according to claim 1, wherein the reference therapeutic antibodies are selected from the group consisting of:
human antibodies, humanized antibodies, bispecific antibodies, chimeric antibodies, Fab, and single domain antibodies.

5. The process according to claim 1, wherein the peptide sequence(s) derived from reference therapeutic antibodies are:
in the hypervariable region of a heavy chain of said antibody-like protein; and/or
in the hypervariable region of a light chain of said antibody-like protein.

6. The process according to claim 1, wherein a hypervariable region of said antibody-like protein comprises more than one polypeptide sequence of a hypervariable region derived from said reference therapeutic antibodies.

7. The process according to claim 1, wherein the reference antibodies are selected from the group consisting of: lnfliximab, Adalimumab, Rituximab, Golimumab, Vedolizumab, Certolizumab, Etanercept, Secukinumab, Cetuximab, Bevacizumab, Nivolumab, Ipilimumab, Atezolizumab, Durvalumab, Avelumab, Trastuzumab, Pertuzumab, Panitumumab, Natalizumab, Pembrolizumab.

8. The process according to claim 1, wherein the labeled chimeric non-therapeutic antibody-like protein comprises:
   a) a heavy chain in which a variable region comprises at least one sequence selected from the group consisting of: SEQ ID NO 13, 15, 17, 19, 21, 23, 25, 27, 29, 31, and 33; and/or
   b) a light chain in which a variable region comprises at least one sequence selected from the group consisting of: SEQ ID NO 14, 16, 18, 20, 22, 24, 26, 28, 30, 32, and 34.

9. The process according to claim 1, wherein the labeled chimeric non-therapeutic antibody-like protein has at least one variable region and at least one constant region.

10. The process according to claim 1, wherein the labeled chimeric non-therapeutic antibody-like protein is structurally similar to an antibody selected from the group consisting of: a IgG, a IgM, a IgE, a IgA, and a IgD antibody.

11. The process according to claim 1, wherein the labeled chimeric non-therapeutic antibody-like protein is structurally similar to a IgG antibody.

12. The process according to claim 1, wherein the labeled chimeric non-therapeutic antibody-like protein is structurally similar to a IgG1 or a IgG4 antibody.

13. The process according to claim 1, wherein the reference antibodies are selected from the group consisting of: Ipilimumab, Nivolumab, Atezolimumab, Durvalumab, Pembrolizumab, or Avelumab.

14. The process according to claim 2, wherein the reference antibodies are selected from the group consisting of: Ipilimumab, Nivolumab, Atezolimumab, Durvalumab, Pembrolizumab, or Avelumab.

15. The process according to claim 1, wherein the reference antibodies are selected from the group consisting of: Ipilimumab, Nivolumab, or Pembrolizumab.

* * * * *

SEQUENCE LISTING

<160> NUMBER OF SEQ ID NOS: 119

<210> SEQ ID NO 1
<211> LENGTH: 218
<212> TYPE: PRT
<213> ORGANISM: Artificial Sequence
<220> FEATURE:
<223> OTHER INFORMATION: Antibody-like protein constitutive fragment

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Thr Ala Tyr Leu
65                  70                  75                  80

Gln Met Asn Ser Leu Arg Ala Glu Asp Thr Ala Val Tyr Tyr Cys Ser
                85                  90                  95

Arg Trp Gly Gly Asp Gly Phe Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu
    210                 215
```

<210> SEQ ID NO 2
<211> LENGTH: 219
<212> TYPE: PRT

<213> ORGANISM: Artificial Sequence
<220> FEATURE:
<223> OTHER INFORMATION: Antibody-like protein constitutive fragment

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu
    210                 215
```

<210> SEQ ID NO 3
<211> LENGTH: 238
<212> TYPE: PRT
<213> ORGANISM: Artificial Sequence
<220> FEATURE:
<223> OTHER INFORMATION: Antibody-like protein constitutive fragment

<400> SEQUENCE: 3

```
Lys Val Asp Lys Lys Val Glu Pro Lys Ser Cys Asp Lys Thr His Thr
1               5                   10                  15

Cys Pro Pro Cys Pro Ala Pro Glu Leu Leu Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110
```

```
Lys Val Ser Asn Lys Ala Leu Pro Ala Pro Ile Glu Lys Thr Ile Ser
            115                 120                 125

Lys Ala Lys Gly Gln Pro Arg Glu Pro Gln Val Tyr Thr Leu Pro Pro
        130                 135                 140

Cys Arg Glu Glu Met Thr Lys Asn Gln Val Ser Leu Trp Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235

<210> SEQ ID NO 4
<211> LENGTH: 238
<212> TYPE: PRT
<213> ORGANISM: Artificial Sequence
<220> FEATURE:
<223> OTHER INFORMATION: Antibody-like protein constitutive fragment

<400> SEQUENCE: 4

Lys Val Asp Lys Lys Val Glu Pro Lys Ser Cys Asp Lys Thr His Thr
1               5                   10                  15

Cys Pro Pro Cys Pro Ala Pro Glu Leu Leu Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Cys Thr Leu Pro Pro
    130                 135                 140

Ser Arg Glu Glu Met Thr Lys Asn Gln Val Ser Leu Ser Cys Ala Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Val Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

```
<210> SEQ ID NO 5
<211> LENGTH: 214
<212> TYPE: PRT
<213> ORGANISM: Artificial Sequence
<220> FEATURE:
<223> OTHER INFORMATION: Antibody-like protein constitutive fragment

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 449
<212> TYPE: PRT
<213> ORGANISM: Artificial Sequence
<220> FEATURE:
<223> OTHER INFORMATION: Antibody-like protein constitutive fragment

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Thr Ala Tyr Leu
65                  70                  75                  80

Gln Met Asn Ser Leu Arg Ala Glu Asp Thr Ala Val Tyr Tyr Cys Ser
                85                  90                  95
```

Arg Trp Gly Gly Asp Gly Phe Tyr Ala Met Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 7
<211> LENGTH: 450
<212> TYPE: PRT
<213> ORGANISM: Artificial Sequence
<220> FEATURE:
<223> OTHER INFORMATION: Antibody-like protein constitutive fragment

<400> SEQUENCE: 7

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
             35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Cys
            340                 345                 350

Thr Leu Pro Pro Ser Arg Glu Glu Met Thr Lys Asn Gln Val Ser Leu
            355                 360                 365

Ser Cys Ala Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
```

```
                420             425             430
Glu Ala Leu His Asn His Tyr Thr Gln Lys Ser Leu Ser Leu Ser Pro
            435                 440                 445

Gly Lys
    450

<210> SEQ ID NO 8
<211> LENGTH: 450
<212> TYPE: PRT
<213> ORGANISM: Artificial Sequence
<220> FEATURE:
<223> OTHER INFORMATION: Antibody-like protein constitutive fragment

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Val Ile Trp Tyr Asp Gly Ser Lys Arg Tyr Tyr Ala Asp Ser
    50                  55                  60

Val Lys Gly Arg Phe Thr Ile Ser Arg Asp Asn Ser Lys Asn Thr Leu
65                  70                  75                  80

Phe Leu Gln Met Asn Ser Leu Arg Ala Glu Asp Thr Ala Val Tyr Tyr
                85                  90                  95

Cys Ser Arg Trp Gly Gly Asp Gly Phe Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                        325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
            405                 410                 415
Asp Lys Ser Arg Trp Gln Gln Gly Asn Val Phe Ser Cys Ser Val Met
        420                 425                 430
His Glu Ala Leu His Asn His Tyr Thr Gln Lys Ser Leu Ser Leu Ser
    435                 440                 445
Pro Gly
    450

<210> SEQ ID NO 9
<211> LENGTH: 214
<212> TYPE: PRT
<213> ORGANISM: Artificial Sequence
<220> FEATURE:
<223> OTHER INFORMATION: Antibody-like protein constitutive fragment

<400> SEQUENCE: 9

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
            85                  90                  95
Thr Phe Gly Gln Gly Thr Lys Val Glu Ile Lys Arg Thr Val Ala Ala
        100                 105                 110
Pro Ser Val Phe Ile Phe Pro Pro Ser Asp Glu Gln Leu Lys Ser Gly
    115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
            165                 170                 175
Ser Thr Leu Thr Leu Ser Lys Ala Asp Tyr Glu Lys His Lys Val Tyr
        180                 185                 190
Ala Cys Glu Val Thr His Gln Gly Leu Ser Ser Pro Val Thr Lys Ser
    195                 200                 205
Phe Asn Arg Gly Glu Cys
    210
```

-continued

<210> SEQ ID NO 10
<211> LENGTH: 450
<212> TYPE: PRT
<213> ORGANISM: Artificial Sequence
<220> FEATURE:
<223> OTHER INFORMATION: Antibody-like protein constitutive fragment

<400> SEQUENCE: 10

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Lys Met Asn Ser Leu Gln Ser Asn Asp Thr Ala Ile Tyr Tyr Cys
                85                  90                  95

Ala Arg Ala Leu Thr Tyr Tyr Asp Tyr Glu Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
```

```
                370                 375                 380
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 11
<211> LENGTH: 449
<212> TYPE: PRT
<213> ORGANISM: Artificial Sequence
<220> FEATURE:
<223> OTHER INFORMATION: Antibody-like protein constitutive fragment

<400> SEQUENCE: 11

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
```

```
                275                 280                 285
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 12
<211> LENGTH: 214
<212> TYPE: PRT
<213> ORGANISM: Artificial Sequence
<220> FEATURE:
<223> OTHER INFORMATION: Antibody-like protein constitutive fragment

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

Ala Cys Glu Val Thr His Gln Gly Leu Ser Ser Pro Val Thr Lys Ser
            195                 200                 205

Phe Asn Arg Gly Glu Cys
    210

<210> SEQ ID NO 13
<211> LENGTH: 449
<212> TYPE: PRT
<213> ORGANISM: Artificial Sequence
<220> FEATURE:
<223> OTHER INFORMATION: Reference Cetuximab heavy chain

<400> SEQUENCE: 13

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 14
<211> LENGTH: 214
<212> TYPE: PRT
<213> ORGANISM: Artificial Sequence
<220> FEATURE:
<223> OTHER INFORMATION: Reference Cetuximab light chain

<400> SEQUENCE: 14

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
                35                  40                  45

Lys Tyr Ala Ser Glu Ser Ile Ser Gly Ile Pro Ser Arg Phe Ser Gly
                50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 15
<211> LENGTH: 453

```
<212> TYPE: PRT
<213> ORGANISM: Artificial Sequence
<220> FEATURE:
<223> OTHER INFORMATION: Reference Bevacizumab heavy chain

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380
```

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 16
<211> LENGTH: 214
<212> TYPE: PRT
<213> ORGANISM: Artificial Sequence
<220> FEATURE:
<223> OTHER INFORMATION: Reference Bevacizumab light chain

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 449
<212> TYPE: PRT
<213> ORGANISM: Artificial Sequence
<220> FEATURE:
<223> OTHER INFORMATION: Reference Trastuzumab heavy chain

<400> SEQUENCE: 17

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
            435                 440                 445

Gly

<210> SEQ ID NO 18
<211> LENGTH: 214
<212> TYPE: PRT
<213> ORGANISM: Artificial Sequence
<220> FEATURE:
<223> OTHER INFORMATION: Reference Trastuzumab light chain

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 440
<212> TYPE: PRT
<213> ORGANISM: Artificial Sequence
<220> FEATURE:
<223> OTHER INFORMATION: Reference Nivolumab heavy chain

<400> SEQUENCE: 19

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
50                  55                  60
```

```
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
             85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 20
<211> LENGTH: 214
<212> TYPE: PRT
<213> ORGANISM: Artificial Sequence
<220> FEATURE:
<223> OTHER INFORMATION: Reference Nivolumab light chain
```

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 21
<211> LENGTH: 450
<212> TYPE: PRT
<213> ORGANISM: Artificial Sequence
<220> FEATURE:
<223> OTHER INFORMATION: Reference Infliximab heavy chain
```

<400> SEQUENCE: 21

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125
```

-continued

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 22
<211> LENGTH: 214
<212> TYPE: PRT
<213> ORGANISM: Artificial Sequence
<220> FEATURE:
<223> OTHER INFORMATION: Reference Infliximab light chain

<400> SEQUENCE: 22

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30
```

Ile His Trp Tyr Gln Gln Arg Thr Asn Gly Ser Pro Arg Leu Leu Ile
                35                  40                  45

Lys Tyr Ala Ser Glu Ser Met Ser Gly Ile Pro Ser Arg Phe Ser Gly
 50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 23
<211> LENGTH: 451
<212> TYPE: PRT
<213> ORGANISM: Artificial Sequence
<220> FEATURE:
<223> OTHER INFORMATION: Reference Adalimumab heavy chain

<400> SEQUENCE: 23

Glu Val Gln Leu Val Glu Ser Gly Gly Gly Leu Val Gln Pro Gly Arg
1                5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
                 35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

-continued

```
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 24
<211> LENGTH: 214
<212> TYPE: PRT
<213> ORGANISM: Artificial Sequence
<220> FEATURE:
<223> OTHER INFORMATION: Reference Adalimumab light chain

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 229
<212> TYPE: PRT
<213> ORGANISM: Artificial Sequence
<220> FEATURE:
<223> OTHER INFORMATION: Reference Certolizumab heavy chain

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

-continued

```
His Thr Cys Ala Ala
225

<210> SEQ ID NO 26
<211> LENGTH: 214
<212> TYPE: PRT
<213> ORGANISM: Artificial Sequence
<220> FEATURE:
<223> OTHER INFORMATION: Reference Certolizumab light chain

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 457
<212> TYPE: PRT
<213> ORGANISM: Artificial Sequence
<220> FEATURE:
<223> OTHER INFORMATION: Reference Golimumab heavy chain

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Asp Arg Gly Ile Ala Ala Gly Gly Asn Tyr Tyr Tyr Tyr Gly
            100                 105                 110

Met Asp Val Ile Ser Ser Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 28
<211> LENGTH: 215
<212> TYPE: PRT
<213> ORGANISM: Artificial Sequence
<220> FEATURE:
```

<223> OTHER INFORMATION: Reference Golimumab light chain

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 29
<211> LENGTH: 451
<212> TYPE: PRT
<213> ORGANISM: Artificial Sequence
<220> FEATURE:
<223> OTHER INFORMATION: Reference Rituximab heavy chain

<400> SEQUENCE: 29

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 30
<211> LENGTH: 213
<212> TYPE: PRT
<213> ORGANISM: Artificial Sequence
<220> FEATURE:
<223> OTHER INFORMATION: Reference Rituximab light chain

<400> SEQUENCE: 30

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30
```

```
His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 31
<211> LENGTH: 457
<212> TYPE: PRT
<213> ORGANISM: Artificial Sequence
<220> FEATURE:
<223> OTHER INFORMATION: Reference Secukinumab heavy chain

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser Ala
            115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175
```

```
Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Arg
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 32
<211> LENGTH: 215
<212> TYPE: PRT
<213> ORGANISM: Artificial Sequence
<220> FEATURE:
<223> OTHER INFORMATION: Reference Secukinumab light chain

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 33
<211> LENGTH: 448
<212> TYPE: PRT
<213> ORGANISM: Artificial Sequence
<220> FEATURE:
<223> OTHER INFORMATION: Reference Ipilimumab heavy chain

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 34
<211> LENGTH: 215
<212> TYPE: PRT
<213> ORGANISM: Artificial Sequence
<220> FEATURE:
<223> OTHER INFORMATION: Reference Ipilimumab light chain

<400> SEQUENCE: 34

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 35
<211> LENGTH: 33
<212> TYPE: PRT
<213> ORGANISM: Artificial Sequence
<220> FEATURE:
<223> OTHER INFORMATION: Tryptic peptide with H-CDR1 from Cetuximab
      (ERB)

<400> SEQUENCE: 35

Gln Ser Gly Pro Gly Leu Val Gln Pro Ser Gln Ser Leu Ser Ile Thr
1               5                   10                  15

Cys Thr Val Ser Gly Phe Ser Leu Thr Asn Tyr Gly Val His Trp Val
            20                  25                  30

Arg

<210> SEQ ID NO 36
<211> LENGTH: 23
<212> TYPE: PRT
<213> ORGANISM: Artificial Sequence
<220> FEATURE:
<223> OTHER INFORMATION: Tryptic peptide with H-CDR2 from Cetuximab
      (ERB)

<400> SEQUENCE: 36

Gly Leu Glu Trp Leu Gly Val Ile Trp Ser Gly Gly Asn Thr Asp Tyr
1               5                   10                  15

Asn Thr Pro Phe Thr Ser Arg
            20

<210> SEQ ID NO 37
<211> LENGTH: 28
<212> TYPE: PRT
<213> ORGANISM: Artificial Sequence
<220> FEATURE:
<223> OTHER INFORMATION: Tryptic peptide with H-CDR3 from Cetuximab
      (ERB)

<400> SEQUENCE: 37

Ala Arg Ala Leu Thr Tyr Tyr Asp Tyr Glu Phe Ala Tyr Trp Gly Gln
1               5                   10                  15

Gly Thr Leu Val Thr Val Ser Ala Ala Ser Thr Lys
            20                  25

<210> SEQ ID NO 38
<211> LENGTH: 15
<212> TYPE: PRT
<213> ORGANISM: Artificial Sequence
<220> FEATURE:
<223> OTHER INFORMATION: Tryptic peptide with L-CDR1 from Cetuximab
      (ERB)

<400> SEQUENCE: 38
```

```
Ala Ser Gln Ser Ile Gly Thr Asn Ile His Trp Tyr Gln Gln Arg
1               5                   10                  15

<210> SEQ ID NO 39
<211> LENGTH: 12
<212> TYPE: PRT
<213> ORGANISM: Artificial Sequence
<220> FEATURE:
<223> OTHER INFORMATION: Tryptic peptide with L-CDR2 from Cetuximab
      (ERB)

<400> SEQUENCE: 39

Tyr Ala Ser Glu Ser Ile Ser Gly Ile Pro Ser Arg
1               5                   10

<210> SEQ ID NO 40
<211> LENGTH: 42
<212> TYPE: PRT
<213> ORGANISM: Artificial Sequence
<220> FEATURE:
<223> OTHER INFORMATION: Tryptic peptide with L-CDR3 from Cetuximab
      (ERB)

<400> SEQUENCE: 40

Phe Ser Gly Ser Gly Ser Gly Thr Asp Phe Thr Leu Ser Ile Asn Ser
1               5                   10                  15

Val Glu Ser Glu Asp Ile Ala Asp Tyr Tyr Cys Gln Gln Asn Asn Asn
            20                  25                  30

Trp Pro Thr Thr Phe Gly Ala Gly Thr Lys
        35                  40

<210> SEQ ID NO 41
<211> LENGTH: 19
<212> TYPE: PRT
<213> ORGANISM: Artificial Sequence
<220> FEATURE:
<223> OTHER INFORMATION: Tryptic peptide with H-CDR1 from Bevacizumab

<400> SEQUENCE: 41

Leu Ser Cys Ala Ala Ser Gly Tyr Thr Phe Thr Asn Tyr Gly Met Asn
1               5                   10                  15

Trp Val Arg

<210> SEQ ID NO 42
<211> LENGTH: 22
<212> TYPE: PRT
<213> ORGANISM: Artificial Sequence
<220> FEATURE:
<223> OTHER INFORMATION: Tryptic peptide with H-CDR2 from Bevacizumab -
      Fragment 1

<400> SEQUENCE: 42

Gly Leu Glu Trp Val Gly Trp Ile Asn Thr Tyr Thr Gly Glu Pro Thr
1               5                   10                  15

Tyr Ala Ala Asp Phe Lys
            20

<210> SEQ ID NO 43
<211> LENGTH: 9
<212> TYPE: PRT
<213> ORGANISM: Artificial Sequence
<220> FEATURE:
<223> OTHER INFORMATION: Tryptic peptide with H-CDR2 from Bevacizumab -
      Fragment 2
```

```
<400> SEQUENCE: 43

Phe Thr Phe Ser Leu Asp Thr Ser Lys
1               5

<210> SEQ ID NO 44
<211> LENGTH: 11
<212> TYPE: PRT
<213> ORGANISM: Artificial Sequence
<220> FEATURE:
<223> OTHER INFORMATION: Tryptic peptide with H-CDR3 from Bevacizumab -
      Fragment 1

<400> SEQUENCE: 44

Ala Glu Asp Thr Ala Val Tyr Tyr Cys Ala Lys
1               5                   10

<210> SEQ ID NO 45
<211> LENGTH: 31
<212> TYPE: PRT
<213> ORGANISM: Artificial Sequence
<220> FEATURE:
<223> OTHER INFORMATION: Tryptic peptide with H-CDR3 from Bevacizumab -
      Fragment 2

<400> SEQUENCE: 45

Ala Lys Tyr Pro His Tyr Tyr Gly Ser Ser His Trp Tyr Phe Asp Val
1               5                   10                  15

Trp Gly Gln Gly Thr Leu Val Thr Val Ser Ser Ala Ser Thr Lys
            20                  25                  30

<210> SEQ ID NO 46
<211> LENGTH: 21
<212> TYPE: PRT
<213> ORGANISM: Artificial Sequence
<220> FEATURE:
<223> OTHER INFORMATION: Tryptic peptide with L-CDR1 from Bevacizumab

<400> SEQUENCE: 46

Val Thr Ile Thr Cys Ser Ala Ser Gln Asp Ile Ser Asn Tyr Leu Asn
1               5                   10                  15

Trp Tyr Gln Gln Lys
            20

<210> SEQ ID NO 47
<211> LENGTH: 16
<212> TYPE: PRT
<213> ORGANISM: Artificial Sequence
<220> FEATURE:
<223> OTHER INFORMATION: Tryptic peptide with L-CDR2 from Bevacizumab

<400> SEQUENCE: 47

Val Leu Ile Tyr Phe Thr Ser Ser Leu His Ser Gly Val Pro Ser Arg
1               5                   10                  15

<210> SEQ ID NO 48
<211> LENGTH: 42
<212> TYPE: PRT
<213> ORGANISM: Artificial Sequence
<220> FEATURE:
<223> OTHER INFORMATION: Tryptic peptide with L-CDR3 from Bevacizumab

<400> SEQUENCE: 48

Phe Ser Gly Ser Gly Ser Gly Thr Asp Phe Thr Leu Thr Ile Ser Ser
1               5                   10                  15

Leu Gln Pro Glu Asp Phe Ala Thr Tyr Tyr Cys Gln Gln Tyr Ser Thr
```

```
              20                  25                  30

Val Pro Trp Thr Phe Gly Gln Gly Thr Lys
        35                  40

<210> SEQ ID NO 49
<211> LENGTH: 15
<212> TYPE: PRT
<213> ORGANISM: Artificial Sequence
<220> FEATURE:
<223> OTHER INFORMATION: Tryptic peptide with H-CDR1 from Nivolumab

<400> SEQUENCE: 49

Ala Ser Gly Ile Thr Phe Ser Asn Ser Gly Met His Trp Val Arg
1               5                  10                  15

<210> SEQ ID NO 50
<211> LENGTH: 14
<212> TYPE: PRT
<213> ORGANISM: Artificial Sequence
<220> FEATURE:
<223> OTHER INFORMATION: Tryptic peptide with H-CDR2 from Nivolumab

<400> SEQUENCE: 50

Gly Leu Glu Trp Val Ala Val Ile Trp Tyr Asp Gly Ser Lys
1               5                  10

<210> SEQ ID NO 51
<211> LENGTH: 30
<212> TYPE: PRT
<213> ORGANISM: Artificial Sequence
<220> FEATURE:
<223> OTHER INFORMATION: Tryptic peptide with H-CDR3 from Nivolumab

<400> SEQUENCE: 51

Ala Glu Asp Thr Ala Val Tyr Tyr Cys Ala Thr Asn Asp Asp Tyr Trp
1               5                  10                  15

Gly Gln Gly Thr Leu Val Thr Val Ser Ser Ala Ser Thr Lys
            20                  25                  30

<210> SEQ ID NO 52
<211> LENGTH: 15
<212> TYPE: PRT
<213> ORGANISM: Artificial Sequence
<220> FEATURE:
<223> OTHER INFORMATION: Tryptic peptide with L-CDR1 from Nivolumab

<400> SEQUENCE: 52

Ala Ser Gln Ser Val Ser Ser Tyr Leu Ala Trp Tyr Gln Gln Lys
1               5                  10                  15

<210> SEQ ID NO 53
<211> LENGTH: 9
<212> TYPE: PRT
<213> ORGANISM: Artificial Sequence
<220> FEATURE:
<223> OTHER INFORMATION: Tryptic peptide with L-CDR2 from Nivolumab

<400> SEQUENCE: 53

Leu Leu Ile Tyr Asp Ala Ser Asn Arg
1               5

<210> SEQ ID NO 54
<211> LENGTH: 36
<212> TYPE: PRT
<213> ORGANISM: Artificial Sequence
<220> FEATURE:
```

<223> OTHER INFORMATION: Tryptic peptide with L-CDR3 from Nivolumab

<400> SEQUENCE: 54

Phe Ser Gly Ser Gly Ser Gly Thr Asp Phe Thr Leu Thr Ile Ser Ser
1               5                   10                  15

Leu Glu Pro Glu Asp Phe Ala Val Tyr Tyr Cys Gln Gln Ser Ser Asn
            20                  25                  30

Trp Pro Arg Thr
        35

<210> SEQ ID NO 55
<211> LENGTH: 15
<212> TYPE: PRT
<213> ORGANISM: Artificial Sequence
<220> FEATURE:
<223> OTHER INFORMATION: Tryptic peptide with H-CDR1 from Rituximab

<400> SEQUENCE: 55

Ala Ser Gly Tyr Thr Phe Thr Ser Tyr Asn Met His Trp Val Lys
1               5                   10                  15

<210> SEQ ID NO 56
<211> LENGTH: 20
<212> TYPE: PRT
<213> ORGANISM: Artificial Sequence
<220> FEATURE:
<223> OTHER INFORMATION: Tryptic peptide with H-CDR2 from Rituximab -
      Fragment 1

<400> SEQUENCE: 56

Gly Leu Glu Trp Ile Gly Ala Ile Tyr Pro Gly Asn Gly Asp Thr Ser
1               5                   10                  15

Tyr Asn Gln Lys
            20

<210> SEQ ID NO 57
<211> LENGTH: 7
<212> TYPE: PRT
<213> ORGANISM: Artificial Sequence
<220> FEATURE:
<223> OTHER INFORMATION: Tryptic peptide with H-CDR2 from Rituximab -
      Fragment 2

<400> SEQUENCE: 57

Ala Thr Leu Thr Ala Asp Lys
1               5

<210> SEQ ID NO 58
<211> LENGTH: 24
<212> TYPE: PRT
<213> ORGANISM: Artificial Sequence
<220> FEATURE:
<223> OTHER INFORMATION: Tryptic peptide with H-CDR3 from Rituximab -
      Fragment 1

<400> SEQUENCE: 58

Ser Ser Ser Thr Ala Tyr Met Gln Leu Ser Ser Leu Thr Ser Glu Asp
1               5                   10                  15

Ser Ala Val Tyr Tyr Cys Ala Arg
            20

<210> SEQ ID NO 59
<211> LENGTH: 29
<212> TYPE: PRT
<213> ORGANISM: Artificial Sequence

```
<220> FEATURE:
<223> OTHER INFORMATION: Tryptic peptide with H-CDR3 from Rituximab -
      Fragment 2

<400> SEQUENCE: 59

Ala Arg Ser Thr Tyr Tyr Gly Gly Asp Trp Tyr Phe Asn Val Trp Gly
1               5                   10                  15

Ala Gly Thr Thr Val Thr Val Ser Ala Ala Ser Thr Lys
            20                  25

<210> SEQ ID NO 60
<211> LENGTH: 14
<212> TYPE: PRT
<213> ORGANISM: Artificial Sequence
<220> FEATURE:
<223> OTHER INFORMATION: Tryptic peptide with L-CDR1 from Rituximab

<400> SEQUENCE: 60

Ala Ser Ser Ser Val Ser Tyr Ile His Trp Phe Gln Gln Lys
1               5                   10

<210> SEQ ID NO 61
<211> LENGTH: 16
<212> TYPE: PRT
<213> ORGANISM: Artificial Sequence
<220> FEATURE:
<223> OTHER INFORMATION: Tryptic peptide with L-CDR2 from Rituximab

<400> SEQUENCE: 61

Pro Trp Ile Tyr Ala Thr Ser Asn Leu Ala Ser Gly Val Pro Val Arg
1               5                   10                  15

<210> SEQ ID NO 62
<211> LENGTH: 26
<212> TYPE: PRT
<213> ORGANISM: Artificial Sequence
<220> FEATURE:
<223> OTHER INFORMATION: Tryptic peptide with L-CDR3 from Rituximab

<400> SEQUENCE: 62

Val Glu Ala Glu Asp Ala Ala Thr Tyr Tyr Cys Gln Gln Trp Thr Ser
1               5                   10                  15

Asn Pro Pro Thr Phe Gly Gly Gly Thr Lys
            20                  25

<210> SEQ ID NO 63
<211> LENGTH: 19
<212> TYPE: PRT
<213> ORGANISM: Artificial Sequence
<220> FEATURE:
<223> OTHER INFORMATION: Tryptic peptide with H-CDR1 from Secukinumab

<400> SEQUENCE: 63

Leu Ser Cys Ala Ala Ser Gly Phe Thr Phe Ser Asn Tyr Trp Met Asn
1               5                   10                  15

Trp Val Arg

<210> SEQ ID NO 64
<211> LENGTH: 15
<212> TYPE: PRT
<213> ORGANISM: Artificial Sequence
<220> FEATURE:
<223> OTHER INFORMATION: Tryptic peptide with H-CDR2 from Secukinumab

<400> SEQUENCE: 64
```

Gly Leu Glu Trp Val Ala Ala Ile Asn Gln Asp Gly Ser Glu Lys
1               5                   10                  15

<210> SEQ ID NO 65
<211> LENGTH: 11
<212> TYPE: PRT
<213> ORGANISM: Artificial Sequence
<220> FEATURE:
<223> OTHER INFORMATION: Tryptic peptide with H-CDR3 from Secukinumab -
      Fragment 1

<400> SEQUENCE: 65

Val Glu Asp Thr Ala Val Tyr Tyr Cys Val Arg
1               5                   10

<210> SEQ ID NO 66
<211> LENGTH: 22
<212> TYPE: PRT
<213> ORGANISM: Artificial Sequence
<220> FEATURE:
<223> OTHER INFORMATION: Tryptic peptide with H-CDR3 from Secukinumab -
      Fragment 2

<400> SEQUENCE: 66

Arg Asp Tyr Tyr Asp Ile Leu Thr Asp Tyr Tyr Ile His Tyr Trp Tyr
1               5                   10                  15
Phe Asp Leu Trp Gly Arg
            20

<210> SEQ ID NO 67
<211> LENGTH: 16
<212> TYPE: PRT
<213> ORGANISM: Artificial Sequence
<220> FEATURE:
<223> OTHER INFORMATION: Tryptic peptide with L-CDR1 from Secukinumab

<400> SEQUENCE: 67

Ala Ser Gln Ser Val Ser Ser Ser Tyr Leu Ala Trp Tyr Gln Gln Lys
1               5                   10                  15

<210> SEQ ID NO 68
<211> LENGTH: 9
<212> TYPE: PRT
<213> ORGANISM: Artificial Sequence
<220> FEATURE:
<223> OTHER INFORMATION: Tryptic peptide with L-CDR2 from Secukinumab

<400> SEQUENCE: 68

Leu Leu Ile Tyr Gly Ala Ser Ser Arg
1               5

<210> SEQ ID NO 69
<211> LENGTH: 26
<212> TYPE: PRT
<213> ORGANISM: Artificial Sequence
<220> FEATURE:
<223> OTHER INFORMATION: Tryptic peptide with L-CDR3 from Secukinumab

<400> SEQUENCE: 69

Leu Glu Pro Glu Asp Phe Ala Val Tyr Tyr Cys Gln Gln Tyr Gly Ser
1               5                   10                  15
Ser Pro Cys Thr Phe Gly Gln Gly Thr Arg
            20                  25

<210> SEQ ID NO 70
<211> LENGTH: 19

```
<212> TYPE: PRT
<213> ORGANISM: Artificial Sequence
<220> FEATURE:
<223> OTHER INFORMATION: Tryptic peptide with H-CDR1 from Ipilimumab

<400> SEQUENCE: 70

Leu Ser Cys Ala Ala Ser Gly Phe Thr Phe Ser Ser Tyr Thr Met His
1               5                   10                  15

Trp Val Arg

<210> SEQ ID NO 71
<211> LENGTH: 15
<212> TYPE: PRT
<213> ORGANISM: Artificial Sequence
<220> FEATURE:
<223> OTHER INFORMATION: Tryptic peptide with H-CDR2 from Ipilimumab

<400> SEQUENCE: 71

Gly Leu Glu Trp Val Thr Phe Ile Ser Tyr Asp Gly Asn Asn Lys
1               5                   10                  15

<210> SEQ ID NO 72
<211> LENGTH: 11
<212> TYPE: PRT
<213> ORGANISM: Artificial Sequence
<220> FEATURE:
<223> OTHER INFORMATION: Tryptic peptide with H-CDR3 from Ipilimumab b -
      Fragment 1

<400> SEQUENCE: 72

Ala Glu Asp Thr Ala Ile Tyr Tyr Cys Ala Arg
1               5                   10

<210> SEQ ID NO 73
<211> LENGTH: 26
<212> TYPE: PRT
<213> ORGANISM: Artificial Sequence
<220> FEATURE:
<223> OTHER INFORMATION: Tryptic peptide with H-CDR3 from Ipilimumab -
      Fragment 2

<400> SEQUENCE: 73

Ala Arg Thr Gly Trp Leu Gly Pro Phe Asp Tyr Trp Gly Gln Gly Thr
1               5                   10                  15

Leu Val Thr Val Ser Ser Ala Ser Thr Lys
            20                  25

<210> SEQ ID NO 74
<211> LENGTH: 16
<212> TYPE: PRT
<213> ORGANISM: Artificial Sequence
<220> FEATURE:
<223> OTHER INFORMATION: Tryptic peptide with L-CDR1 from Ipilimumab

<400> SEQUENCE: 74

Ala Ser Gln Ser Val Gly Ser Ser Tyr Leu Ala Trp Tyr Gln Gln Lys
1               5                   10                  15

<210> SEQ ID NO 75
<211> LENGTH: 9
<212> TYPE: PRT
<213> ORGANISM: Artificial Sequence
<220> FEATURE:
<223> OTHER INFORMATION: Tryptic peptide with L-CDR2 from Ipilimumab

<400> SEQUENCE: 75
```

Leu Leu Ile Tyr Gly Ala Phe Ser Arg
1               5

<210> SEQ ID NO 76
<211> LENGTH: 26
<212> TYPE: PRT
<213> ORGANISM: Artificial Sequence
<220> FEATURE:
<223> OTHER INFORMATION: Tryptic peptide with L-CDR3 from Ipilimumab

<400> SEQUENCE: 76

Leu Glu Pro Glu Asp Phe Ala Val Tyr Tyr Cys Gln Gln Tyr Gly Ser
1               5                   10                  15

Ser Pro Trp Thr Phe Gly Gln Gly Thr Lys
            20                  25

<210> SEQ ID NO 77
<211> LENGTH: 8
<212> TYPE: PRT
<213> ORGANISM: Artificial Sequence
<220> FEATURE:
<223> OTHER INFORMATION: H-CDR1 from Nivolumab

<400> SEQUENCE: 77

Gly Ile Thr Phe Ser Asn Ser Gly
1               5

<210> SEQ ID NO 78
<211> LENGTH: 17
<212> TYPE: PRT
<213> ORGANISM: Artificial Sequence
<220> FEATURE:
<223> OTHER INFORMATION: H-CDR2 from Nivolumab

<400> SEQUENCE: 78

Val Ile Trp Tyr Asp Gly Ser Lys Arg Tyr Tyr Ala Asp Ser Val Lys
1               5                   10                  15

Gly

<210> SEQ ID NO 79
<211> LENGTH: 6
<212> TYPE: PRT
<213> ORGANISM: Artificial Sequence
<220> FEATURE:
<223> OTHER INFORMATION: H-CDR3 from Nivolumab

<400> SEQUENCE: 79

Ala Thr Asn Asp Asp Tyr
1               5

<210> SEQ ID NO 80
<211> LENGTH: 6
<212> TYPE: PRT
<213> ORGANISM: Artificial Sequence
<220> FEATURE:
<223> OTHER INFORMATION: L-CDR1 from Nivolumab

<400> SEQUENCE: 80

Gln Ser Val Ser Ser Tyr
1               5

<210> SEQ ID NO 81

<400> SEQUENCE: 81

000

<210> SEQ ID NO 82
<211> LENGTH: 9
<212> TYPE: PRT
<213> ORGANISM: Artificial Sequence
<220> FEATURE:
<223> OTHER INFORMATION: L-CDR3 from Nivolumab

<400> SEQUENCE: 82

Gln Gln Ser Ser Asn Trp Pro Arg Thr
1               5

<210> SEQ ID NO 83
<211> LENGTH: 8
<212> TYPE: PRT
<213> ORGANISM: Artificial Sequence
<220> FEATURE:
<223> OTHER INFORMATION: H-CDR1 from Cetuximab

<400> SEQUENCE: 83

Gly Phe Ser Leu Thr Asn Tyr Gly
1               5

<210> SEQ ID NO 84
<211> LENGTH: 7
<212> TYPE: PRT
<213> ORGANISM: Artificial Sequence
<220> FEATURE:
<223> OTHER INFORMATION: H-CDR2 from Cetuximab

<400> SEQUENCE: 84

Ile Trp Ser Gly Gly Asn Thr
1               5

<210> SEQ ID NO 85
<211> LENGTH: 13
<212> TYPE: PRT
<213> ORGANISM: Artificial Sequence
<220> FEATURE:
<223> OTHER INFORMATION: H-CDR3 from Cetuximab

<400> SEQUENCE: 85

Ala Arg Ala Leu Thr Tyr Tyr Asp Tyr Glu Phe Ala Tyr
1               5                   10

<210> SEQ ID NO 86
<211> LENGTH: 6
<212> TYPE: PRT
<213> ORGANISM: Artificial Sequence
<220> FEATURE:
<223> OTHER INFORMATION: L-CDR1 from Cetuximab

<400> SEQUENCE: 86

Gln Ser Ile Gly Thr Asn
1               5

<210> SEQ ID NO 87

<400> SEQUENCE: 87

000

<210> SEQ ID NO 88
<211> LENGTH: 9
<212> TYPE: PRT
<213> ORGANISM: Artificial Sequence
<220> FEATURE:

```
<223> OTHER INFORMATION: L-CDR3 from Cetuximab

<400> SEQUENCE: 88

Gln Gln Asn Asn Asn Trp Pro Thr Thr
1               5

<210> SEQ ID NO 89
<211> LENGTH: 8
<212> TYPE: PRT
<213> ORGANISM: Artificial Sequence
<220> FEATURE:
<223> OTHER INFORMATION: H-CDR1 from Bevacizumab

<400> SEQUENCE: 89

Gly Tyr Thr Phe Thr Asn Tyr Gly
1               5

<210> SEQ ID NO 90
<211> LENGTH: 11
<212> TYPE: PRT
<213> ORGANISM: Artificial Sequence
<220> FEATURE:
<223> OTHER INFORMATION: H-CDR2 from Bevacizumab

<400> SEQUENCE: 90

Gly Trp Ile Asn Thr Tyr Thr Gly Glu Pro Thr
1               5                   10

<210> SEQ ID NO 91
<211> LENGTH: 17
<212> TYPE: PRT
<213> ORGANISM: Artificial Sequence
<220> FEATURE:
<223> OTHER INFORMATION: H-CDR3 from Bevacizumab

<400> SEQUENCE: 91

Ala Lys Tyr Pro His Tyr Tyr Gly Ser Ser His Trp Tyr Phe Asp Val
1               5                   10                  15

Trp

<210> SEQ ID NO 92
<211> LENGTH: 6
<212> TYPE: PRT
<213> ORGANISM: Artificial Sequence
<220> FEATURE:
<223> OTHER INFORMATION: L-CDR1 from Bevacizumab

<400> SEQUENCE: 92

Gln Asp Ile Ser Asn Tyr
1               5

<210> SEQ ID NO 93

<400> SEQUENCE: 93

000

<210> SEQ ID NO 94
<211> LENGTH: 8
<212> TYPE: PRT
<213> ORGANISM: Artificial Sequence
<220> FEATURE:
<223> OTHER INFORMATION: L-CDR3 from Bevacizumab

<400> SEQUENCE: 94

Gln Gln Tyr Ser Thr Val Pro Trp
```

```
<210> SEQ ID NO 95
<211> LENGTH: 8
<212> TYPE: PRT
<213> ORGANISM: Artificial Sequence
<220> FEATURE:
<223> OTHER INFORMATION: H-CDR1 from Rituximab

<400> SEQUENCE: 95

Gly Tyr Thr Phe Thr Ser Tyr Asn
1               5

<210> SEQ ID NO 96
<211> LENGTH: 9
<212> TYPE: PRT
<213> ORGANISM: Artificial Sequence
<220> FEATURE:
<223> OTHER INFORMATION: H-CDR2 from Rituximab

<400> SEQUENCE: 96

Ile Tyr Pro Gly Asn Gly Asp Thr Ser
1               5

<210> SEQ ID NO 97
<211> LENGTH: 14
<212> TYPE: PRT
<213> ORGANISM: Artificial Sequence
<220> FEATURE:
<223> OTHER INFORMATION: H-CDR3 from Rituximab

<400> SEQUENCE: 97

Ala Arg Ser Thr Tyr Tyr Gly Gly Asp Trp Tyr Phe Asn Val
1               5                   10

<210> SEQ ID NO 98
<211> LENGTH: 5
<212> TYPE: PRT
<213> ORGANISM: Artificial Sequence
<220> FEATURE:
<223> OTHER INFORMATION: L-CDR1 from Rituximab

<400> SEQUENCE: 98

Ser Ser Val Ser Tyr
1               5

<210> SEQ ID NO 99

<400> SEQUENCE: 99

000

<210> SEQ ID NO 100
<211> LENGTH: 9
<212> TYPE: PRT
<213> ORGANISM: Artificial Sequence
<220> FEATURE:
<223> OTHER INFORMATION: L-CDR3 from Rituximab

<400> SEQUENCE: 100

Gln Gln Trp Thr Ser Asn Pro Pro Thr
1               5

<210> SEQ ID NO 101
<211> LENGTH: 8
<212> TYPE: PRT
<213> ORGANISM: Artificial Sequence
```

```
<220> FEATURE:
<223> OTHER INFORMATION: H-CDR1 from Secukinumab

<400> SEQUENCE: 101

Gly Phe Thr Phe Ser Asn Tyr Trp
1               5

<210> SEQ ID NO 102
<211> LENGTH: 9
<212> TYPE: PRT
<213> ORGANISM: Artificial Sequence
<220> FEATURE:
<223> OTHER INFORMATION: H-CDR2 from Secukinumab

<400> SEQUENCE: 102

Ala Ile Asn Gln Asp Gly Ser Glu Lys
1               5

<210> SEQ ID NO 103
<211> LENGTH: 19
<212> TYPE: PRT
<213> ORGANISM: Artificial Sequence
<220> FEATURE:
<223> OTHER INFORMATION: H-CDR3 from Secukinumab

<400> SEQUENCE: 103

Arg Asp Tyr Tyr Asp Ile Leu Thr Asp Tyr Tyr Ile His Tyr Trp Tyr
1               5                   10                  15

Phe Asp Leu

<210> SEQ ID NO 104
<211> LENGTH: 7
<212> TYPE: PRT
<213> ORGANISM: Artificial Sequence
<220> FEATURE:
<223> OTHER INFORMATION: L-CDR1 from Secukinumab

<400> SEQUENCE: 104

Gln Ser Val Ser Ser Ser Tyr
1               5

<210> SEQ ID NO 105

<400> SEQUENCE: 105

000

<210> SEQ ID NO 106
<211> LENGTH: 8
<212> TYPE: PRT
<213> ORGANISM: Artificial Sequence
<220> FEATURE:
<223> OTHER INFORMATION: L-CDR3 from Secukinumab

<400> SEQUENCE: 106

Gln Gln Tyr Gly Ser Ser Pro Cys
1               5

<210> SEQ ID NO 107
<211> LENGTH: 8
<212> TYPE: PRT
<213> ORGANISM: Artificial Sequence
<220> FEATURE:
<223> OTHER INFORMATION: H-CDR1 from Ipilimumab

<400> SEQUENCE: 107
```

Gly Phe Thr Phe Ser Ser Tyr Thr
1               5

<210> SEQ ID NO 108
<211> LENGTH: 10
<212> TYPE: PRT
<213> ORGANISM: Artificial Sequence
<220> FEATURE:
<223> OTHER INFORMATION: H-CDR2 from Ipilimumab

<400> SEQUENCE: 108

Thr Phe Ile Ser Tyr Asp Gly Asn Asn Lys
1               5                   10

<210> SEQ ID NO 109
<211> LENGTH: 11
<212> TYPE: PRT
<213> ORGANISM: Artificial Sequence
<220> FEATURE:
<223> OTHER INFORMATION: H-CDR3 from Ipilimumab

<400> SEQUENCE: 109

Ala Arg Thr Gly Trp Leu Gly Pro Phe Asp Tyr
1               5                   10

<210> SEQ ID NO 110
<211> LENGTH: 7
<212> TYPE: PRT
<213> ORGANISM: Artificial Sequence
<220> FEATURE:
<223> OTHER INFORMATION: L-CDR1 from Ipilimumab

<400> SEQUENCE: 110

Gln Ser Val Gly Ser Ser Tyr
1               5

<210> SEQ ID NO 111

<400> SEQUENCE: 111

000

<210> SEQ ID NO 112
<211> LENGTH: 9
<212> TYPE: PRT
<213> ORGANISM: Artificial Sequence
<220> FEATURE:
<223> OTHER INFORMATION: L-CDR3 from Ipilimumab

<400> SEQUENCE: 112

Gln Gln Tyr Gly Ser Ser Pro Trp Thr
1               5

<210> SEQ ID NO 113
<211> LENGTH: 448
<212> TYPE: PRT
<213> ORGANISM: Artificial Sequence
<220> FEATURE:
<223> OTHER INFORMATION: Antibody-like protein constitutive fragment

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Thr Phe Ser Asn Ser
            20                  25                  30

Gly Met His Trp Val Arg Gln Ala Pro Gly Lys Gly Leu Glu Trp Leu 35                  40                  45
Gly Val Ile Trp Ser Gly Gly Asn Thr Asp Tyr Asn Thr Pro Phe Thr
 50                  55                  60

Ser Arg Phe Thr Ile Ser Ala Asp Thr Ser Lys Asn Thr Ala Tyr Leu
 65                  70                  75                  80

Gln Met Asn Ser Leu Arg Ala Glu Asp Thr Ala Val Tyr Tyr Cys Ser
                 85                  90                  95

Arg Trp Gly Asp Gly Phe Tyr Ala Met Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 114

```
<211> LENGTH: 214
<212> TYPE: PRT
<213> ORGANISM: Artificial Sequence
<220> FEATURE:
<223> OTHER INFORMATION: Antibody-like protein constitutive fragment

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Lys Tyr Ala Ser Glu Ser Ile Ser Gly Ile Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 115
<211> LENGTH: 450
<212> TYPE: PRT
<213> ORGANISM: Artificial Sequence
<220> FEATURE:
<223> OTHER INFORMATION: Antibody-like protein constitutive fragment

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
```

```
            100                 105                 110
Gly Thr Leu Val Thr Val Ser Ser Ala Ser Thr Lys Gly Pro Ser Val
        115                 120                 125

Phe Pro Leu Ala Pro Ser Ser Lys Ser Thr Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 116
<211> LENGTH: 451
<212> TYPE: PRT
<213> ORGANISM: Artificial Sequence
<220> FEATURE:
<223> OTHER INFORMATION: Antibody-like protein constitutive fragment

<400> SEQUENCE: 116

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Pro Gly Lys Gly Leu
            35                  40                  45

Glu Trp Leu Gly Val Ile Trp Ser Gly Gly Asn Thr Asp Tyr Asn Thr
            50                  55                  60

Pro Phe Thr Ser Arg Leu Ser Ile Asn Lys Asp Asn Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Ser Arg Trp Gly Gly Asp Gly Phe Tyr Ala Met Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430
```

```
Met His Glu Ala Leu His Asn His Tyr Thr Gln Lys Ser Leu Ser Leu
        435                 440                 445

Ser Pro Gly
    450

<210> SEQ ID NO 117
<211> LENGTH: 214
<212> TYPE: PRT
<213> ORGANISM: Artificial Sequence
<220> FEATURE:
<223> OTHER INFORMATION: Antibody-like protein constitutive fragment

<400> SEQUENCE: 117

Asp Ile Gln Met Thr Gln Ser Pro Ser Ser Leu Ser Ala Ser Val Gly
1               5                   10                  15

Asp Arg Val Thr Leu Ser Cys Arg Ala Ser Gln Ser Val Ser Ser Tyr
            20                  25                  30

Leu Ala Trp Tyr Gln Gln Lys Pro Gly Lys Ala Pro Arg Leu Leu Ile
        35                  40                  45

Tyr Asp Ala Ser Asn Arg Ala Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 118
<211> LENGTH: 214
<212> TYPE: PRT
<213> ORGANISM: Artificial Sequence
<220> FEATURE:
<223> OTHER INFORMATION: Antibody-like protein constitutive fragment

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
```

```
                 50                  55                  60
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                     85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 119
<211> LENGTH: 450
<212> TYPE: PRT
<213> ORGANISM: Artificial Sequence
<220> FEATURE:
<223> OTHER INFORMATION: Antibody-like protein constitutive fragment

<400> SEQUENCE: 119

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
                195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
450
```